US006958392B2

(12) United States Patent
Fomovskaia et al.

(10) Patent No.: US 6,958,392 B2
(45) Date of Patent: Oct. 25, 2005

(54) METHODS FOR THE ISOLATION OF NUCLEIC ACIDS AND FOR QUANTITATIVE DNA EXTRACTION AND DETECTION FOR LEUKOCYTE EVALUATION IN BLOOD PRODUCTS

(75) Inventors: Galina N. Fomovskaia, Boston, MA (US); Martin A. Smith, Brookline, MA (US); Mikhail A. Fomovsky, Boston, MA (US); Neil J. Butt, Cambridge (GB)

(73) Assignee: Whatman, Inc., Florham Park, NJ (US)

( * ) Notice: Subject to any disclaimer, the term of this patent is extended or adjusted under 35 U.S.C. 154(b) by 158 days.

(21) Appl. No.: 09/908,452

(22) Filed: Jul. 18, 2001

(65) Prior Publication Data

US 2002/0150907 A1 Oct. 17, 2002

Related U.S. Application Data

(63) Continuation-in-part of application No. 09/736,659, filed on Dec. 14, 2000, now Pat. No. 6,746,841, which is a continuation-in-part of application No. PCT/US00/10230, filed on Apr. 14, 2000, which is a continuation-in-part of application No. 09/414,533, filed on Oct. 8, 1999.
(60) Provisional application No. 60/226,650, filed on Aug. 21, 2000, provisional application No. 60/193,556, filed on Mar. 31, 2000, provisional application No. 60/180,353, filed on Feb. 4, 2000, and provisional application No. 60/129,191, filed on Apr. 14, 1999.

(30) Foreign Application Priority Data

Oct. 9, 1998 (GB) .............................................. 9822141
Aug. 2, 1999 (GB) .............................................. 9918193

(51) Int. Cl.⁷ .............................................. C07H 21/02
(52) U.S. Cl. ................................ 536/25.42; 536/25.41; 536/25.4
(58) Field of Search .......................... 536/25.42, 25.41, 536/25.4

(56) References Cited

U.S. PATENT DOCUMENTS

| | | | | |
|---|---|---|---|---|
| 5,070,009 A | * | 12/1991 | Crepin et al. ................... | 435/6 |
| 5,187,083 A | | 2/1993 | Mullis .......................... | 435/91 |
| 5,234,809 A | | 8/1993 | Boom et al. ................... | 435/91 |
| 5,234,824 A | | 8/1993 | Mullis .......................... | 435/91 |
| 5,496,562 A | * | 3/1996 | Burgoyne .................... | 424/488 |
| 5,652,141 A | | 7/1997 | Henco et al. ................. | 435/270 |
| 5,756,126 A | * | 5/1998 | Burgoyne .................... | 424/488 |
| 5,807,527 A | * | 9/1998 | Burgoyne .................... | 424/488 |
| 5,958,677 A | * | 9/1999 | Lee et al. ...................... | 435/5 |
| 6,020,186 A | | 2/2000 | Henco et al. ............. | 435/287.2 |
| 6,645,717 B1 | * | 11/2003 | Smith et al. ................... | 435/6 |
| 6,746,841 B1 | * | 6/2004 | Fomovskaia et al. .......... | 435/6 |
| 2001/0000149 A1 | * | 4/2001 | Smith et al. ................... | 435/6 |
| 2001/0007746 A1 | * | 7/2001 | Smith et al. ................... | 435/6 |
| 2002/0010323 A1 | * | 1/2002 | Mitchell et al. ............ | 536/23.1 |
| 2002/0150907 A1 | * | 10/2002 | Fomovskaia et al. .......... | 435/6 |

FOREIGN PATENT DOCUMENTS

| | | | |
|---|---|---|---|
| DE | WO 92/07863 | 5/1992 | |
| EP | 0389063 A2 | * 9/1990 | |
| EP | 0 725 149 A1 | 8/1996 | ............ C12Q/1/68 |
| EP | 0389063 B1 | 8/1997 | |
| EP | 814 156 A2 | 12/1997 | |
| EP | 0 814 156 A2 | 12/1997 | |
| US | WO 99/13976 | 3/1999 | |
| WO | WO 90/03959 | 4/1990 | ........... C07B/63/00 |
| WO | WO 96/00348 | 1/1996 | |
| WO | WO 96/41810 | 12/1996 | |
| WO | WO 98/11989 | 3/1998 | |
| WO | WO 00/04195 | 1/2000 | |
| WO | WO 00/21973 | 4/2000 | |
| WO | WO00/49031 A2 | * 8/2000 | |
| WO | WO 00/53807 | 9/2000 | |
| WO | WO00/53807 A1 | * 9/2000 | |
| WO | WO 00/62023 | 10/2000 | |
| WO | WO00/73412 A2 | * 12/2000 | |

OTHER PUBLICATIONS

Nelson et al., "Purification of Cloned and Genomic DNA by Guanidine Isothiocyanate/Isobutyl Alcohol Fractionation," *Analytical Biochemistry*, 207(1), 197–201 (Nov. 15, 1992).*

(Continued)

*Primary Examiner*—L. E. Crane
*Assistant Examiner*—Thomas C. McKenzie
(74) *Attorney, Agent, or Firm*—Edwards & Angell, LLP; David G. Conlin; Kathryn A. Piffat

(57) ABSTRACT

A method for isolating nucleic acid which comprises:
(a) applying a sample comprising cells containing nucleic acid to a filter, whereby the cells are retained as a retentate and contaminants are removed;
(b) lysing the retentate from step (a) while the retentate is retained by the filter to form a cell lysate containing the nucleic acid;
(c) filtering the cell lysate with the filter to retain the nucleic acid and remove remaining cell lysate;
(d) optionally washing the nucleic acid retained by the filter; and
(e) eluting the nucleic acid, wherein the filter composition and dimensions are selected so that the filter is capable of retaining the cells and the nucleic acid.

Additionally, there is provided a substrate for lysing cells and purifying nucleic acid having a matrix and a coating and an integrity maintainer for maintaining the purified nucleic acid. Also provided is a method of purifying nucleic acid by applying a nucleic acid sample to a substrate having an anionic detergent affixed to a matrix, the substrate physically capturing the nucleic acid, bonding the nucleic acid to a substrate and generating a signal when the nucleic acid bonds to the substrate indicating the presence of the nucleic acid. A kit for purifying nucleic acid containing a coated matrix and an integrity maintenance provider for preserving the matrix and purifying nucleic acid is also provided. Further, there is provided a method for quantifying DNA, such as double-stranded or genomic DNA, isolated from cells, such as leukocytes to determine the numbers of leukocytes in a sample of leukoreduced blood.

63 Claims, 24 Drawing Sheets

OTHER PUBLICATIONS

Ramírez-Solis et al., "Genomic DNA Microextraction: A Method to Screen Numerous Samples," *Analytical Biochemistry*, 201(2), 331–335 (Mar. 1992).*

Douglas et al., "Purification of Human Leucocyte DNA: Proteinase K Is Not Necessary," *Analytical Biochemistry*, 201(2), 362–365 (Mar., 1992).*

Miller et al., "A Simple Salting Out Procedure for Extracting DNA From Human Nucleated Cells," *Nucleic Acids Research*, 16(3), 1215 (Feb. 11, 1988).*

Vogelstein et al., "Preparative and Analytical Purification of DNA from Agarose," *Proc. National Academy of Science USA*, 76(2), 615–619 (Feb., 1979).*

Lehninger, *Biochemistry, Second Edition*, Worth Publishers, New York, NY, Jul., 1978, only p. 309 supplied.*

Mucenski et al., "Evaluation of a Synthetic Oligonucleotide Probe for Diagnosis of Plasmodium Falciparum Infections," *American J. Tropical Medicine & Hygiene*, 35(5), 912–920 (1986); *Chemical Abstracts*, 106(3), p. 315, Abstract No. 15358d (Jan. 19, 1987); only Abstract supplied.*

Panteleeff et al., "Rapid Method for Screening Dried Blood Samples on Filter Paper for Human Immunodeficiency Virus Type 1 DNA," *Journal of Clinical Microbiology*, 37(2), 350–353 (Feb., 1999).*

Nelson et al., "Purification of Cloned and Genomic DNA by Guanidine Thiocyanate/Isobutyl Alcoh Fractionation," *Analytical Biochemistry*, vol. 207, pp. 197–201, 1992.

Ramírez-Solis et al., "Genomic DNA Microextraction: A Method to Screen Numerous Samples," *Analytical Biochemistry*, vol. 201, pp. 331–335, 1991.

Douglas et al., "Purification of Human Leucocyte DNA: Proteinase K is not necessary," *Analytical Biochemistry*, vol. 201, pp. 362–365, 1991.

Miller et al., et al., A simple salting out procedure for extracting DNA from human nucleated cells *Nucleic Acids Research*, vol. 16, No. 3, p. 1215, (1988).

Yang, et al., "DNA ligands that bind tightly and selectively to cellobiose," *Proc. Natl. Acad. Sci. USA*, vol. 95, pp. 5462–5467, May 1998.

Rogers, et al., "Reverse transcription of an RNA genome from databasing paper (FTA®)," Biotechnol. Appl. Biochem. (2000) vol. 31, pp. 219–224.

Eisenberg, et al., "High throughput automated DNA sample analysis for both RFLP and PCR using FTA<® paper and the Rosys robotic microplate processor," http://www.bio.flinders.edu.au/eisenb.html, Date of print–out: Feb. 24, 1999.

Both, et al., "FTA Paper, DNA, Time and the Profiler," http://www.bio.flinders.edu.au/vidocq.html, Date of print-out: Feb. 22, 1999.

Renz, et al., "A colorimetric method for DNA hybridization," Nucleic Acids Research, vol. 12, No. 8, 1984, pp. 3435–3444.

Del Rio, et al., "Reusing the Same Blood–stained Punch for Sequential DNA Amplifications and Typing," BioTechniques, vol. 20, No. 6, (1996), pp. 970–974 (pp. 971 & 973 are blank pages).

Matsuhisa, et al., "A Simple Staining Method for DNA and RNA Blotted on a Membrane Using a Polyethyleneimine–Enzyme Conjugate," J. Biochem., vol. 116, pp. 478–481, (1994).

Vogelstein et al. *Preparative and Analytical Purification of DNA from Agarose.* Proceedings of the National Academy of Science USA., Feb., 1979. vol. 76, No. 2, pp. 615–619, see entire document.

Lehninger, A.L., *Nucleotides and the Covalent Structure of Nucleic Acids*, Biochemistry, Second Edition, "The Molecular Basis of Cell Structure and Function", The Johns Hopkins University School of Medicine, Chapter 12, p. 309, see first paragraph. (Jul., 1978).

Rogers et al., Bacterial Typing: Storing and Processing of Stabilized Reference Bacteria for Polymerase Chain Reaction without Preparing DNA—An Example of an Automatable Procedure, Analytical Biochemistry, 247:223–227 (1997).

Biochemicals Organic Compounds, Sigma, Alphabetical list of Compounds pp. 851–852.

Advancing Science, Aldrich, p. 2400 (2005–2006).

Matsuhisa et al. "A simple Staining method for DNS and RNA blotted on a membrane using a polyethyleneimine–Enzyme donjugate", Journal of Biochemistry, 116(3): 478–481 (1994), XP002929739.

(Z) EPO Examination Report for Application No. 00 922 263.9 –1212, Whatman, Inc., Jan. 31, 2005.*

(RA) PCT Search Report for Application No. PCT/US01/25709, mailed Feb. 2, 2005, Whatman, Inc.*

(RB) EPO Lack of Unity and Supplement Search Report for Application No. 01 964 105.9, mailed Nov. 25, 2004, Whatman, Inc.*

Legler et al., "Quantitative PCT for counting residual white blood cells in blood products" Transfusion Science, 20(2)107–111 (1999) (Apr. 1999).

Baker et al., "Isolation of Genomic DNA from Blood Using a Novel Filter–Based DNA Purification Technology", BioTechniques, 31(1) :142–145 (2001) (Jul. , 2001).

Walter H. Dzik, "Leukocyte Counting during Process Control of Leukoreduced Blood Components" Vox Sanguinis, 78 (suppl. 2) :223–226 (2000).

* cited by examiner

METHODS FOR THE ISOLATION OF NUCLEIC ACIDS AND FOR QUANTITATIVE DNA EXTRACTION AND DETECTION FOR LEUKOCYTE EVALUATION IN BLOOD PRODUCTS

CROSS-REFERENCE TO RELATED APPLICATIONS

This application is a Continuation-in-Part of U.S. patent application Ser. No. 09/736,659, filed Dec. 14, 2000, now U.S. Pat. No. 6,746,841 which is a Continuation-in-Part of PCT application No. PCT/US00/10230, filed Apr. 14, 2000, which claims the benefit of priority under 35 USC Section 119(e) of U.S. Provisional Patent Application No. 60/129,191, filed on Apr. 14, 1999; U.S. Provisional Patent Application No. 60/180,353, filed on Feb. 4, 2000; and U.S. Provisional Patent Application No. 60/193,556, filed on Mar. 31, 2000, all of which are incorporated herein by reference; this application is also a Continuation-in-Part of a CPA application filed Mar. 21, 2001, which is a CPA of U.S. patent application Ser. No. 09/414,533, filed Oct. 8, 1999, which claims the benefit of priority of United Kingdom application 9918193.5, filed on Aug. 2, 1999, and United Kingdom application 9822141.9, filed on Oct. 9, 1998, all of which are incorporated herein by reference; and this application also claims priority of U.S. Provisional Patent Application 60/226,650, filed Aug. 21, 2000, which is incorporated herein by reference.

FIELD OF THE INVENTION

The present invention relates to a method for isolating nucleic acid from a sample containing nucleic acid, such as a cell sample or cell lysate, to the quantitative detection of nucleic acid, and, further, to the estimation of leukocytes in blood products, including leukoreduced blood products. It also relates to kits and apparatus for DNA evaluation, such as for the evaluation of leukocytes in leukoreduced blood products. The invention is particularly advantageous for the analysis of blood transfusion products for leukocytes or other nucleotide-containing contaminants.

BACKGROUND OF THE INVENTION

While relatively rapid and convenient procedures for the purification of nucleic acid (such as DNA) from agarose have been developed, it remains a relatively difficult operation to extract nucleic acid directly from more complex starting samples such as cells and cell lysates. On the whole, the procedures currently practiced to purify nucleic acid from nucleic acid-containing samples comprising cells or cell lysates remain time consuming and labor intensive.

One method proposed to minimize the laborious and time-consuming steps of the known method for isolating nucleic acid from these more complex sample is described in EP 0389063. The method disclosed in EP 0389063 involves mixing the cell sample (such as whole blood) with a chaotropic substance and a particulate nucleic acid binding solid phase comprising silica or a derivative thereof. It is known that, in the presence of a chaotropic substance, nucleic acid is released from cells and binds to silica-based nucleic acid binding solid phases. Subsequently, the mixture is centrifuged to pellet the solid phase with the nucleic acid bound thereto and the supernatant is discarded. The pelletized material is subjected to several washing stages with the chaotropic agent and organic solvents. Finally, the DNA is eluted from the solid phase in a low salt buffer.

The method described in EP 0389063 is disadvantageous in that it is a manually intensive, multi-step procedure. In view of the fact that the method involves a number of centrifugation and vessel transfer steps, this method is unsuitable for automation.

U.S. Pat. Nos. 5,187,083 and 5,234,824 each describe a method for rapidly obtaining substantially pure DNA from a biological sample containing cells. The methods involve gently lysing the membranes of the cells to yield a lysate containing genomic DNA in a high molecular weight form. The lysate is moved through a porous filter to trap selectively the high molecular weight DNA on the filter. The DNA is released from the filter using an aqueous solution.

The present invention aims to provide an improved method for isolating nucleic acid from a nucleic acid-containing sample, such as cells or cell lysate, which avoids the use of centrifugation steps and which avoids the requirement of upstream processing of the sample in order to render the nucleic acid amenable to binding to a solid phase.

Genotyping is the discipline of identifying an individual's genome in relation to disease specific alleles and/or mutations that occur as an effect of parental linkage. The rapid purification of human genomic DNA is an essential part of a genotyping process; the genomic DNA of an individual being the structural unit for the entire DNA sequence of every allele expressed.

Human genomic DNA cannot be directly sequenced. In order to carry out sequence analysis on regions of the chromosomes that may contain portions of mutation or disease specific sequences, selected portions are amplified, e.g., via PCR, and the amplified products are sequenced. The selected portions of the chromosomes that are amplified are dictated by the specific sequence of the primers used in the PCR amplification. The primer sets that are used in genotyping studies are commercially available and are representative for the chromosome under examination. If linkage studies identify that a disease-bearing sequence is on a particular chromosome, then many primer sets will be utilized across that chromosome in order to obtain genetic material for sequencing. The resultant PCR products may well represent the entire chromosome under examination. Due to the large length of chromosomes, many PCR reactions are carried out on the genomic DNA template from a single patient.

Human genomic DNA is purified by a variety of methods (Molecular Cloning, Sambrook et al. (1989)). Consequently, many commercial kit manufacturers provide products for such techniques, for example: AmpReady™ (Promega, Madison, Wis.), DNeasy™ (Qiagen, Valencia, Calif.), and Split Second™ (Roche Molecular Biochemicals, Indianapolis, Ind.). These products rely on the use of specialized matrices or buffer systems for the rapid isolation of the genomic DNA molecule.

More recently, microporous filter-based techniques have surfaced as tools for the purification of genomic DNA as well as a whole multitude of nucleic acids. The advantage of filter-based matrices are that they can be fashioned into many formats that include tubes, spin tubes, sheets, and microwell plates. Microporous filter membranes as purification support matrices have other advantages within the art. They provide a compact, easy to manipulate system allowing for the capture of the desired molecule and the removal of unwanted components in a fluid phase at higher throughput and faster processing times than possible with column chromatography. This is due to the fast diffusion rates possible on filter membranes.

Nucleic acid molecules have been captured on filter membranes, generally either through simple adsorption or through a chemical reaction between complementary reactive groups present on the filter membrane or on a filter-bound ligand resulting in the formation of a covalent bond between the ligand and the desired nucleic acid.

Porous filter membrane materials used for non-covalent nucleic acid immobilization have included materials such as nylon, nitrocellulose, hydrophobic polyvinylidinefluoride (PVDF), and glass microfiber. A number of methods and reagents have also been developed to also allow the direct coupling of nucleic acids onto solid supports, such as oligonucleotides and primers (eg. J. M. Coull et al., Tetrahedron Lett. vol. 27, page 3991; B. A. Conolly, Nucleic Acids Res., vol. 15, page 3131, 1987; B. A. Conolly and P. Rider, Nucleic Acids Res., vol. 12, page 4485, 1985; Yang et al., P.N.A.S. vol. 95: 5462–5467). UV cross-linking of DNA (Church et al., PNAS, vol. 81, page 1991, 1984), The Generation Capture Column Kit (Gentra Systems, Minneapolis, Minn.) and RNA (Khandjian et al., Anal. Biochem, vol. 159, pages 227, 1986) to nylon membranes have also been reported.

Many chemical methods have been utilized for the immobilization of molecules such as nucleic acids on filter membranes. For example, activated paper (TransBind™, Schleicher & Schuell Ltd., Keene, N.H.) carbodimidazole-activated hydrogel-coated PVDF membrane (Immobilin-IAV™, Millipore Corp., Bedford, Mass.), MAP paper (Amersham, Littlechalfont Bucks, Wis.), activated nylon (BioDyne™, Pall Corp., (Glen Cove, N.Y.), DVS- and cyanogen bromide-activated nitrocellulose. Membranes bound with specific ligands are also known such as the SAM2™ Biotin Capture Membrane (Promega) which binds biotinylated molecules based on their affinity to streptavidin or MAC affinity membrane system (protein A/G) (Amicon, Bedford, Mass.). Some of the disadvantages of covalent attachment of biomolecules onto activated membranes are:

a) Molecule immobilization is often slow, requiring 20–180 minutes for reaction completion.
b) High ligand and biomolecule concentration is needed for fast immobilization.
c) Constant agitation is needed during the immobilization process, which may result in biomolecule denaturation and deactivation.
d) Once the immobilization process is complete, often a blocking (capping) step is required to remove residual covalent binding capacity.
e) Covalently bound molecules can not be retrieved from the filter membrane.

There is a need in various specific areas, such as forensics, for a nucleic acid immobilization media and procedure that exhibits the high specificity of covalent immobilization onto the filter membrane without the use of harsh chemical reactions and long incubation times, which can also be used at crime scenes, with blood sample archiving and other related uses. In particular there is a need for the capture and separation of nucleic acids from a mixture in a fluid phase onto a filter membrane matrix in forensics.

Of special interest is the ability to store or archive the bound nucleic acids on the filter membrane matrix for various uses. Alternatively, filters that permit elution of nucleic acids have uses in application requiring liquid formats. Embodiments of both types are found in the present invention.

More recently, glass microfiber, has been shown to specifically bind nucleic acids from a variety of nucleic acid containing sources very effectively (for example, see Itoh et al (1997) Simple and rapid preparation of plasmid template by filtration method using microtiter filter plates. NAR, vol. 25, No. 6: 1315–1316; Andersson, B. et al. (1996) Method for 96-well M13 DNA template preparations for large-scale sequencing. BioTechniques vol. 20: 1022–1027). Under the correct salt and buffering conditions, nucleic acids will bind to glass or silica with high specificity.

Based on U.S. Pat. Nos. 5,496,562, 5,756,126, and 5,807,527, it has been demonstrated that nucleic acids or genetic material can be immobilized to a cellulosic-based dry solid support or filter (FTA filter). The solid support described is conditioned with a chemical composition that is capable of carrying out several functions: (i) lyse intact cellular material upon contact, releasing genetic material, (ii) enable and allow for the conditions that facilitate genetic material immobilization to the solid support (probably by a combination of mechanical and chaotrophic), (iii) maintain the immobilized genetic material in a stable state without damage due to degradation, endonuclease activity, UV interference, and microbial attack, and (iv) maintain the genetic material as a support-bound molecule that is not removed from the solid support during any down stream processing (as demonstrated by Del Rio et al (1995) BioTechniques. vol. 20: 970–974).

The usefulness of the so called FTA cellulosic filter material described in U.S. Pat. Nos. 5,496,562, 5,756,126, and 5,807,527 has been illustrated for several nucleic acid techniques such as bacterial ribotyping (Rogers, C. & Burgoyne, L. (1997) Anal. Biochem. vol. 247: 223–227), detection of single base differences in viral and human DNA (Ibrahim et al. (1998) Anal. Chem. vol. 70: 2013–2017), DNA databasing (Ledray et al. (1997) J. Emergency Nursing. vol. 23, No. 2: 156–158), automated processing for STR electrophoresis (Belgrader, B. & Marino, M. (1996) L.R.A. vol. 9: 3–7, Belgrader et al. (1995) BioTechniques. vol. 19, No.3: 427–432), and oligonucleotide ligation assay for diagnostics (Baron et al. (1996) Nature Biotech. vol. 14: 1279–1282).

It has been shown that nucleic acid or genetic material applied to, and immobilized to, FTA filters cannot be simply removed, or eluted from the solid support once bound (Del Rio et al (1995) BioTechniques. vol. 20: 970–974). This is a major disadvantage for applications where several downstream processes are required from the same sample, such a STR profiling and genotyping.

FTA filter media has also been employed for DNA analysis and comparison in other ways. For example, cellular material has been applied to FTA filter media, and generally the cellular material, once applied, forms a spot on the FTA filter. From this spot, small punches can be taken; each small punch will have immobilized to it enough nucleic acid or genetic material to facilitate a single downstream process such as a PCR reaction. As the two primers administered to a PCR reaction are presented in solution, it is of no consequence that the cellular nucleic acid template is immobilized to the filter. All amplicon will be formed in solution. Amplicon can then be readily removed from the reaction by aspirating the liquid phase away from the FTA solid filter punch. Therefore, for multiple processing from a single sample, many punches have to be taken. Multiple punching is very time consuming, and as yet, has not lent itself to simplified automation.

A primary use for the present invention is the analysis of blood transfusion products for leukocytes or other contaminants. Each year in the United States about 14 million transfusions of blood or blood components takes place. There are three major blood products in transfusion medicine:

1. RED CELLS (RBC, typically about 340 ml contained in 1 unit of donor blood)—the remaining red cell mass after most of the plasma is removed.
2. PLATELETS (typically 300 ml/1 unit of donor blood) or platelet concentrates (PCs, typically further concentrated to about 50 ml/1 unit of donor blood)—one platelet concentrate (one unit of random donor platelets) is derived from one unit of donor blood.
3. FRESH FROZEN PLASMA (FFP, 225 ml/1 unit of donor blood)—One unit of FFP can raise coagulation factor levels by 8% and fibrinogen by 13 mg/dl in the average patient.

Despite the increasing need for transfusions and the use of transfusion products, such use involves a number of risks. About 150,000 patients a year experience adverse reactions to such products. Such adverse reactions occur regardless the type of blood transfusion a patient receives. Ninety percent of adverse transfusion reactions are caused by donor leukocytes contained in the transfusion products.

Further problems stem from Human Leukocyte Antigen (HLA) alloimmunization, in which the recipient is sensitized to antibodies contained in the transfusion product which can react, for example, to the recipient's leukocytes (HLA sensitization).

Where the recipient suffers from a non-hemolytic febrile transfusion reaction, the patient most frequently experiences fever, chills, and nausea due to white blood components contained in the transfusion product, to which the patients has antibodies (usually anti-HLA).

Other serious risks of the use of transfusion products include transmission and/or reactivation of cytomegalovirus (CMV), occurrence of graft-versus-host disease (GVHD), and the risk of viral transmissions. (HIV, HCV transmission are the most feared complications of transfusion.)

Certain precautions have been adopted in order to reduce the likelihood and/or severity of adverse reactions to transfusion products. Leukoreduction of blood product before transfusion into a patient is considered the most significant recent improvement in safety and purity of blood transfusion. Leukoreduction is the process of removing >99.9% of the white blood cells (WBC) from cellular blood components (red cells and platelets).

The FDA has announced publicly that it will require that all cellular blood components transfused in the U.S be leukoreduced by the year 2002. Worldwide, ten countries, including Canada, Britain, France, Portugal, and Germany, have mandated universal leukocyte reduction, and 13 more, including Denmark, Italy, Japan, and New Zealand, are moving toward the practice.

As in any essential step of blood processing, the step of leukoreduction is subject to quality control. In order to label a component as leukocyte-reduced (leukoreduced), the American Association of Blood Bank Standards (19th ed) requires that the residual leukocyte content in the component is $<5 \times 10^6$ WBC/unit blood. European guidelines define leukocyte reduction as $<1 \times 10^6$ leukocytes/unit.

FDA guidelines state that quality control testing of leukocyte-reduced units should be performed on at least 1% of products (or 4/month for facilities preparing <400 units/month) and that 100% of tested units should contain $<5 \times 10^6$ residual leukocytes/unit.

During the 1990's numerous methods were developed for testing for residual leukocytes, based on light microscopy, fluorescence labeling, or DNA amplification. In 1998, FDA approved three protocols for QC control of leukoreduced blood products:

1. Manual counting of cells in the fixed volume of transfusion product, using a Nageotte hemacytometer.
2. Flow cytometric methods, which use fluorescent beads or labeled chicken erythrocytes as internal control, and
3. The Imagn 2000 device for analyzing a fixed blood samples in a capillary chamber.

Recent methods have limitations for proposed centralization of testing services for leukoreduced blood products in terms of sample storage time and their integrity. These methods are based on actual cell counts using cell shape, size and brightness to discriminate cell from background. Both manual and automated approaches require fresh blood, because these described parameters change with blood storage, or are sensitive to sample preparation techniques. All traditional methods are very sensitive to blood storage time because cells' deterioration and changing of size and/or shape during storage or the freezing-thawing process.

According to expert opinion, "Wide scale testing has shifted to more automated methods. However, deterioration of samples as a result of prolonged sample shipment remains an obstacle to centralized testing service." (Walter H. Dzick, Von Sang 2000, 78, 223:226). "The requirement of fresh samples for processing is particularly problematic in connection with applications such as Quality control of WBC-reduced blood components by blood centers." (T.-H. Lee, M. P Busch, Transfusion, 1998.38. 262:270; Transfusion, 2001, 41.276: 282.).

Other problems with such conventional methods include timing of the analysis. For example, the time required for one sample analysis using flow cytometry (sampling and analysis of histogram) is too long (3–10 min for a single sample analysis) to permit large scale testing. Further, flow cytometry and especially manual Nageotte methods both require well-trained personnel for consistent and accurate result interpretation.

Problems with traditional methods of analysis have led to implementation of DNA based analysis for quality control of WBC-reduced component has recently been recognized as an alternative of traditional "cell shape, size, and brightness" methods. Typically, DNA analysis is based on the fact that only white blood cells in human blood have genomic DNA. All other blood cellular elements, red cells and platelets are nuclei-free. The majority of all white blood cells (>99%) are not proliferating. Thus they have a known, relatively constant amount of DNA that is equal to about 7 pg per cell. Previous approaches to this technology claimed substantial, but not total, DNA recovery from whole blood samples.

One method has been evaluated with respect to quantitative recovery of WBC-associated DNA when the target cell population is present at very low concentration in test samples, and this method uses the Polymerase Chain Reaction (PCR) to detect and quantify genetic material in frozen whole blood samples. However, a Quantitative PCR protocol takes many hours to process. That is even slower in some ways than flow cytometry.

Further, PCR methods are very expensive. They require unique real time PCR devices and expensive PCR reagent kits. The preparation of calibration standard samples is labor consuming and very sophisticated. The required operator's skills are at the Ph.D. level. Thus there is a clear need for a simple, effective, and rapid method for analyzing blood transfusion products for leukocyte or other nucleotide-containing contaminants.

It is desirable to adapt the present technology and modify it for specific use such as for forensic art or for detection of leukocytes in blood products, including leukoreduced blood. Additionally, it would be advantageous to be able to rapidly qualify and quantify nucleic acid on media, either in correlation with such uses, or independent thereof.

SUMMARY OF THE INVENTION

According to the present invention there is provided a substrate for lysing cells and purifying nucleic acid having a matrix and a coating and an integrity maintainer for maintaining the purified nucleic acid. Also provided is a method of purifying nucleic acid by applying a nucleic acid sample to a substrate, the substrate physically capturing the nucleic acid, bonding the nucleic acid to the substrate and generating a signal when the nucleic acid bonds to the substrate indicating the presence of the nucleic acid. A kit for purifying nucleic acid containing a coated matrix and an integrity maintenance provider for preserving the matrix and purifying nucleic acid is also provided.

According to the present invention, there is provided also a method for isolating nucleic acid which comprises:

(a) applying a sample comprising cells containing nucleic acid to a filter, whereby the cells are retained as a retentate and contaminants are removed;

(b) lysing the retentate from step (a) while the retentate is retained by the filter to form a cell lysate containing the nucleic acid;

(c) filtering the cell lysate with the filter to retain the nucleic acid and remove remaining cell lysate;

(d) optionally washing the nucleic acid retained by the filter, and (e) eluting the nucleic acid, wherein the filter composition and dimensions are selected so that the filter is capable of retaining the cells and the nucleic acid.

Preferably, step (b) comprises lysing the retentate while it is entrapped within the filter.

Preferably, the filter composition and dimensions are selected so that the nucleic acid is retained by the filter in step (c) substantially in the absence of ionic interaction. More preferably, the filter composition and dimensions are selected so that the nucleic acid is retained by the filter by a physical retarding of the movement of the nucleic acid down the filter. Preferably, the filter composition and dimensions are selected so that the nucleic acid is retained by the filter, in step (c) in the form of a web. Preferably, for purposes of quantitative nucleic acid isolation, the filter is compressed prior to addition of the sample, beyond the compression used to construct the filter.

Preferably, the nucleic acid is heated to an elevated temperature while being retained by the filter prior to eluting in step (e). More preferably, heating and subsequent elution are repeated at least once for quantitative purposes.

According to the present invention, there is provided likewise a kit for isolating nucleic acid from a sample comprising cells containing nucleic acid comprising:

(a) an apparatus as defined comprising a filter supported by a support wherein the filter composition and dimensions are selected so that the filter is capable of retaining the cells and the nucleic acid;

(b) one or more solutions selected from a red cell lysis solution, a solution for rupturing intact whole cells to leave condensed nuclear material, a lysis solution for lysing nuclear material and an elution solution.

In addition, the present invention envisages the use of the above kit in a method for isolating nucleic acid from a sample comprising cells containing nucleic acid, in particular in a method according to the present invention.

According to the present invention, there is provided also the use of a filter or an apparatus comprising a filter supported by a support in a method for isolating nucleic acid from a sample comprising cells containing nucleic acid. The filter compositions and dimensions are selected so that the filter is capable of retaining the cells and the nucleic acid. Preferably, the filter is any filter suitable for use in the method according to the present invention.

In addition, the present invention can be utilized for quantitative extraction and detection of DNA from a sample for evaluation of residual leukocytes in blood products, including leukocyte-reduced (or leukoreduced) blood products. In one embodiment, a sample of a blood product is exposed to a filter, matrix, or membrane. Cells are lysed, and the nucleic acid becomes physically or chemically attached to, or within, the filter, matrix, or membrane. The nucleic acid may be washed to remove non-nucleic acid components. The nucleic acid is eluted from the filter and quantitatively analyzed in order to estimate the number of leukocytes remaining in the sample. More particularly, detection methods specific for double-stranded, single-stranded, or genomic DNA may be used. The amount of DNA is then used to calculate the number of residual leukocytes in the sample (approximately 7 pg DNA/leukocyte) in order to evaluate leukoreduction of the blood product from which the sample was taken. Preferably, the resulting determination of the number of white blood cells in the sample is at least 85% of the number of white blood cells measured via standard methods of flow cytometry used in the blood product industry. More preferably, the resulting determination is at least 90% compared to flow cytometry measurements. More preferably still, it is at least 95% compared to flow cytometry measurements, yet more preferably still, it is at least 98% compared to flow cytometry measurements, and most preferably, it is at least 99% compared to flow cytometry measurements.

In another embodiment, the nucleic acid (from the cells in the blood product sample) is not eluted from the filter, matrix, or membrane. Rather, the DNA on or within the filter, matrix, or membrane is quantitatively analyzed without elution. Preferably, the nucleic acid is captured on the filter surface, such as a cellulose nitrate surface on a polymeric filter. Again, detection methods specific for double-stranded or genomic DNA may be used, followed by estimation of the number of residual leukocytes, as described above.

The present invention will now be described in further detail with reference to the accompanying Examples and Experiments and to the attached Figures in which:

BRIEF DESCRIPTION OF THE DRAWINGS

FIG. 22B showing Step 2: Nucleated cell lysis;
FIG. 22C shows Step 3: Wash Step;
and
FIG. 22D depicts Step 4: Elution Step.

Figure 18A:
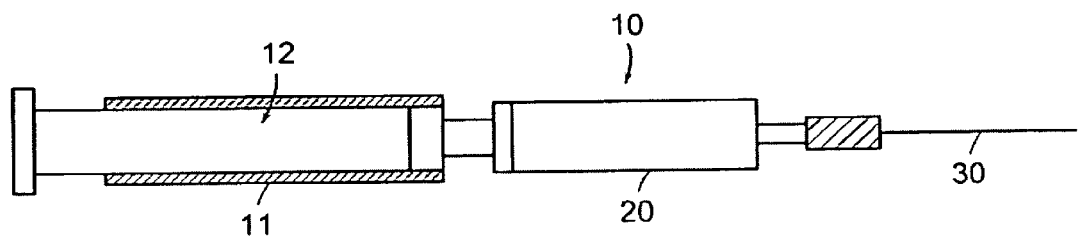
FIG. 18A is a plan view, partially in sections, of a clinical extraction device suitable for use in the present invention.
Figure 18B:
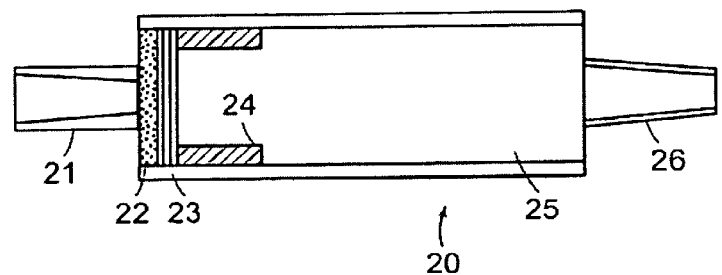
FIG. 18B is a plan view, in section of the extraction cartridge as depicted in FIG. 18A
Figure 19:
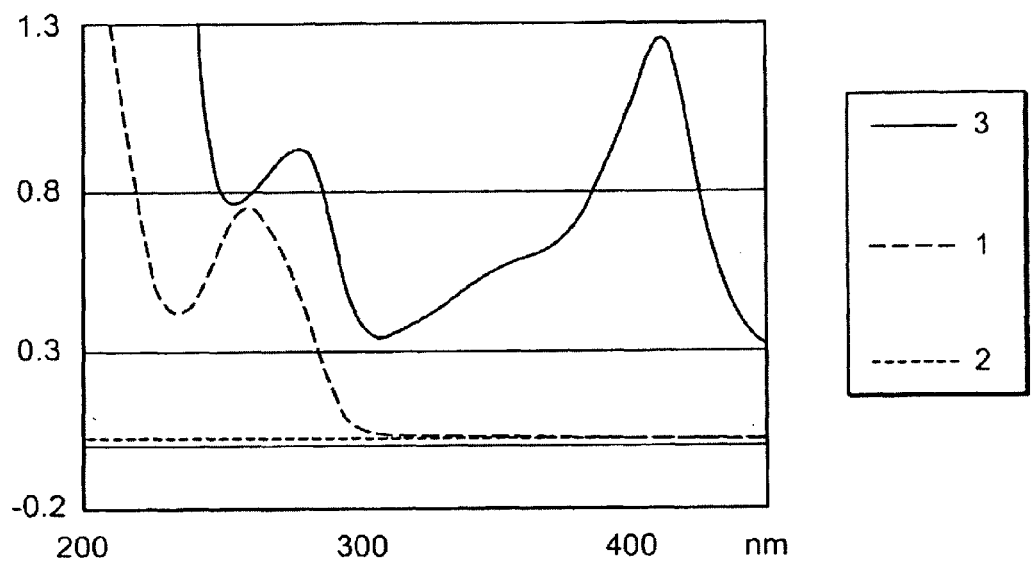
FIG. 19 is a spectroscopic analysis of solutions eluted from the present column (1)=waste eluant after step 3
(2)=waste eluant after step 4
(3)=eluted DNA solution

A device is provided which may, in one aspect, be used in the extraction of samples such as blood according to the method described above. Such a device is depicted in FIGS. 18A and 18B.

The device consists of the cartridge (20), which may be of any desired volume, typically 1 ml, 5 ml, or 10 ml. The cartridge comprises a body (25) which may be coated on its interior surface with a metal chelating agent such as EDTA. The cartridge has an inlet (26) and an outlet (21) disposed between which is a filter (23) which may comprise a plurality of filter layers. The filter or filters are preferably disposed between a filter support or frit (22) and a filter retaining member (24) for retaining the filter or filters in place. The filter retaining member (24) is preferably a ring which may make a friction fit inside the body of the cartridge. The body of the cartridge is preferably a barrel. The metal chelator acts to prevent coagulation of blood taken as a sample once inside the cartridge and other known anticoagulants may be used in its place. The inlet is preferably adapted to receive a needle assembly (30) and may comprise a male lure (26). The outlet, typically arranged adjacent the filter support (22) is preferably adapted to receive a syringe (11) and is typically a female lure (21).

In a preferred arrangement, the filter or filters are as described above and may be used in the isolation of nucleic acid such as DNA as hereinbefore described.

In use, with a syringe (11) and needle (30) attached to the cartridge, the needle is inserted into a vein of a subject or other sample source, and blood drawn into cartridge (20) by drawing back the portion of the syringe (11). Blood enters the cartridge preferably until it is full. The needle and syringe are then detached and the cartridge capped off with a suitable capping member (not shown). The cartridge may then be transported or stored at 4° C., −20° C. or −70° C. until required for processing. Storage conditions will vary depending on the likely length of time until DNA extraction may be performed.

When the DNA is to be extracted, frozen samples will need to be defrosted. The cartridge may be placed in a rack which may hold any number of samples, typically 96. The rack is then placed inside a device which, in sequence, delivers reagents and is heated to perform an extraction in accordance with the method described hereinbefore.

An advantage of this device is that the blood is collected, transported and extracted in a single device. This avoids the need to transfer samples from collection to extraction device and minimizes the potential for sample mix-up.

In a preferred embodiment, the device will bear a unique marking to identify the sample, such as a bar coding.

Traditionally, filters are selected so as to have a pore size and composition which will act as an absolute barrier so as to prevent the material to be filtered from passing through or into the filter material. For example, by selecting a filter material with a particular pore size it is possible to prevent materials with a particle size greater than the pore size from passing through or into the filter material. It has been found by the applicant that an improved method for purifying nucleic acid is obtained when a filter material is selected which does not provide an absolute barrier entry to the cells, but enables the cells to enter into, and be retained by, the filter as a retentate, in particular to pass into the filter material and to become entrapped therein. These steps occur prior to lysing the retentate, while the retentate is retained by the filter to form a cell lysate containing the nucleic acid. Subsequent to in situ lysing of the retentate, the filter is also capable of retaining the nucleic acid but not other cell components. As a consequence, where the sample comprises whole blood which has been treated with a red blood cell lysis solution, the solution containing red cell debris passes through the filter and may be discarded, while the white cells containing the nucleic acid are retained by the filter as a retentate. Red cell lysis is not absolutely necessary as the filter will allow intact red cells to pass through. However, inclusion of the red blood cell lysis solution leads to a cleaner final product.

It has been found that the present method substantially improves the yield and purity of the nucleic acid product. Furthermore, the present method provides a quick, simplified, cost effective method for nucleic acid purification that is not manually intensive or technique-dependent and does not utilize hazardous chemicals. The nucleic acid produced in accordance with one embodiment of the present invention is capable of multiple downstream processing. Optionally, the nucleic acids retained by the filter may be washed with any suitable wash solution. Preferably, the nucleic acid retained by the filter is washed with a buffer having a pH in the range 5.8 to 10, more preferably in the range 7 to 8. In particular, washing with water or a low salt buffer such as $TE^{-1}$ (10 mM Tris HCL (pH 8) with 100 $\mu$m EDTA) is preferred. The washing step may occur prior to or at the same time as elution step (e). Washing increases the yield and purity of the nucleic acid product and ensures that the filter stays damp during incubation. If the filter is allowed to dry the nucleic acid still is recoverable but may be sheared and the yield will be reduced. Where the method is carried out in a column, drying of the filter also may be avoided by using a water vapor retarding or blocking seal such as a rubber bung in the column to reduce evaporation of solution from the filter. The washing step removes any remains of the cell material-lysis solution which may be problematic in downstream processing.

It is preferred that the retentate be lysed while entrapped within the filter. However, it should be understood that the method according to the present invention encompasses also an embodiment where substantially all or some of retentate is lysed while retained by, but not entrapped within, the filter.

In one aspect of the present invention, the retentate comprises condensed nuclear material and cell debris. In this aspect, on application of a sample comprising cells containing nucleic acid to the filter, the cell membrane is ruptured or gently "peeled away" to form condensed nuclear material and cell debris which is retained by the filter. It is thought that the condensed nuclear material may comprise intact nuclei.

In another aspect of the present invention, the retentate comprises intact whole cells as well as, or instead of, condensed nuclear material and cell debris. Advantageously, the intact whole cells may be treated in step (b), while being retained by the filter, by the application of a detergent to the filter. Any detergent may be used, provided that it has the effect of rupturing or "peeling away" the cell membrane to leave condensed nuclear material. The condensed nuclear material is retained by the filter. Preferably the detergent is selected from sodium dodecyl sulfate (particularly 0.5% weight-by-volume SDS), or other commercially available detergents such as TWEEN™ 20 (particularly 1% volume-by-volume TWEEN™ 20), LDS (particularly 1% w/v LDS) or TRITON™ e.g., TRITON™ X-100 (particularly 1% v/v TRITON™). The amount of detergent employed is sufficient to lyse cell membranes, but not so much as to denature DNA. Suitable amounts are generally 0.1% to 2% by weight (w/v) and preferably 0.2% to 1.5% w/v and more preferably 0.5% to 1.05% w/v.

While the addition of detergent to the retentate is preferable, the present method may be carried out without the addition of a detergent by using other known lysing agents. However, applying a detergent to the retentate while the retentate is retained by the filter increases the yield and purity of the DNA product.

In addition to rupturing the intact whole cells to form condensed nuclear material, the detergent also has the function of washing out protein and heme which may have been retained by the filter.

After step (b), lysis, the retentate comprises freed nucleic acids.

Alternatively, the retentate is lysed to form a cell lysate containing nucleic acid in step (b) by the addition of a low salt buffer. Preferably, the low salt buffer is $TE^{-1}$ (10 mM Tris; 0.1 mM EDTA; pH8) or water. Other suitable lysis solutions include any detergent-containing solutions in which the detergent may be cationic, anionic or neutral. Chaotrope-containing solutions, preferably buffers may also be used. The lysis solution lyses or bursts open the condensed nuclear material to release the nucleic acid. It will be understood by the skilled person, however, that lysing the retentate to form a cell lysate containing nucleic acid also can be achieved by other methods, for example, by heating.

The retention or entrapment of the cells and nucleic acid by the filter may arise by virtue of a physical or size-related barrier relating to the dimensions of the filter material including the pore size and depth of the filter, or by other means. Without wishing to be bound by theory, it is thought that the nucleic acid may be physically associated with the filter rather than chemically or otherwise tightly bound thereto. It is postulated that nucleic acid-nucleic acid interactions themselves are important in maintaining a sufficiently high cross-sectional area to retard movement of the nucleic acid through the filter.

Preferably, the filter composition and dimensions are selected so that the nucleic acid is retained by the filter in step (c) in the form of a web. For the purpose of the present invention, the term "web" can be taken to include partly or substantially disordered structures, lattice-type structures, mesh-type structures, complex network-type structures, tangle-type structures or knot-type structures. The web may have a loose or open stringy-type structure and may comprise a plurality of strands. The web structure does not involve substantial direct or intimate binding, for example by ionic interactions, of the nucleic acid directly onto the filter.

Advantageously, the filter comprises a plurality of fibers and has a substantially disordered structure. Preferably, the fiber diameters are selected so that the nucleic acid is retained by the filter in step (c) in the form of a web. In accordance with the definition of the term "web" as described above, the structure of the web is such that there is substantially no direct binding, for example by ionic interactions, of the nucleic acid directly onto the fibers. More preferably the fiber diameters are selected so that they are in the range of from 1 $\mu$m to 30 $\mu$m, even more preferably in the range of from 3 $\mu$m to 15 $\mu$m, most preferably about 5–12 $\mu$m.

Filter materials that are suitable for use in the present invention include any material which enables the cells to be retained by the filter as a retentate and the nucleic acid to be retained by the filter, preferably in the form of a web.

Suitable materials include glass fiber or any silica-based or derived filters and plastic based filters, for example polyester and polypropylene based filters.

Referring to the filter, it is preferred that the composition and dimensions are selected so that the filter is capable of retaining the cells and the nucleic acid substantially in the absence of a chaotrope. It has been surprisingly found by the applicant that with certain filter materials, including glass microfiber, woven or non-woven polyethylene, woven or non-woven polyester, or woven or non-woven polypropylene, it is possible to isolate nucleic acid in the absence of a chaotrope. This goes against the conventional wisdom of those skilled in the art of the invention.

Preferably, the filter material is of a depth that is sufficiently large to entrap the cells and the nucleic acid within the filter without substantial loss. Accordingly, a filter of a suitable depth may comprise a plurality of filter layers arranged in series. The number of filter layers influences the total nucleic acid yield and concentration. Preferably, the plurality of filter layers is stacked one above the other and is supported, e.g., by a frit. The present method is scalable so that any surface area of the filter and thus any filter diameter may be used.

One suitable filter for use in the present method is a Whatman GF/D variant filter. Preferably, the lysate is exposed to a stack of four Whatman GF/D variant filters. The filters may be stacked into a column of 6 mm in diameter and supported, e.g., on a glass frit. Various parameters of the GF/D variant filter are set out in Table 1 below.

TABLE 1

Characteristics of Whatman GF/D Variant Filter.

| Parameter | Units | Typical Values |
|---|---|---|
| Grammage | g/m$^2$ | 115 |
| Thickness C53kPa | $\mu$m | 677 |
| Porosity (5 oz cylinder) | s/300 mls/in$^2$ | 4.7 |
| Tensile (MD) | N/15 mm | 5.8 |
| Water Absorption | mg/cm$^2$ | 137 |
| Pore Sizes | $\mu$m | |
| Minimum | | 4.5 |
| Maximum | | 14.5 |
| Mean | | 7.9 |

It is preferred also that the filter composition and dimensions are selected so that the nucleic acid in step (e) is capable of being eluted at a pH of from pH 5 to 11 or preferably from pH 5.8 to 10. This is advantageous in the present method because elution of the product nucleic acid in a more highly alkaline medium potentially can degrade the product. Accordingly, one preferred pH for elution is from 7 to 9.

Eluting the nucleic acid, in other words releasing the nucleic acid from the filter, may be affected in several ways. The efficiency of elution may be improved by putting energy into the system during an incubation step to release the nucleic acid prior to elution. This may be in the form of physical energy (for example by agitating) or heat energy. The incubation or release time may be shortened by increasing the quantity of energy put into the system.

Preferably, heat energy is put into the system by heating the nucleic acid to an elevated temperature for a predetermined time, while it is retained by the filter, prior to eluting in step (e), but not so hot or for such a time as to be damaged. [However, elution still may be effected when the nucleic acid has not been heated to an elevated temperature or even has been held at a lowered temperature (as low as 4° C.) prior to elution in step (e).] More preferably, the nucleic acid is heated to an elevated temperature in the range of 40° C. to 125° C., even more preferably in the range of from 80° C. to 95° C. Most preferably, the nucleic acid is heated to an elevated temperature of about 90° C., advantageously for about 10 minutes for a filter having a 6 mm diameter. Increasing the filter diameter increases the yield of DNA at any given heating temperature.

It should be noted that predominantly single stranded material will be produced from the present system. However, the ratio of double to single stranded DNA is dependent upon, and can be controlled by, the experimental conditions. Modifying the incubation regime using the parameters of time and temperature will alter this ratio, where a lower elution temperature over a longer time period will produce a high proportion of double stranded DNA. A higher elution temperature over a shorter period of time also will produce a higher proportion of double stranded DNA.

Once the nucleic acid has been heated to an elevated temperature while retained by the filter, it is not necessary to maintain the nucleic acid at the elevated temperature during elution. Elution itself may be at any temperature. For ease of processing, it is preferred that, where the nucleic acid is heated to an elevated temperature while retained by the filter, elution will be at a temperature lower than the elevated temperature. This is because when heating has been stopped, the temperature of the nucleic acid will fall over time and also will fall as a result of the application of any ambient temperature eluting solution to the filter. Any solution at any pH which is suitable for eluting the nucleic acid from the present filter may work. Preferred elution solutions include NaOH 1 mM to 1 M, Na acetate 1 mM to 1M, 10 mM 2-[N-morpholino]-ethanesulfonic acid (MES) (pH 5.6), 10 mM 3-[cyclohexylamino]-1-propanesulfonic acid (CAPS) (pH 10.4), TE (10 mM Tris HCL (p H8)+1 mM EDTA), TE$^{-1}$ (10 mM Tris; 0.1 mM EDTA; pH 8), sodium dodecyl sulfate (SDS) (particularly 0.5% SDS), TWEEN™ 20 (particularly 1% TWEEN™ 20), LDS (particularly 1% lauryl dodecyl sulfate (LDS)) or TRITON™ (particularly 1% TRITON™), water and 10 mM Tris. All yield approximately the same quantity of nucleic acid. Total yields of nucleic acid are higher when eluted in a high volume of elution solution.

In steps (a) to (d) of the present method, the temperature is usually ambient temperature, typically in the range 5° C. to 40° C.

In general, the present method may be applied advantageously to any whole cell suspension. Cells particularly amenable to the present method include bacterial cells, yeast cells and mammalian cells, such as white blood cells, epithelial cells, buccal cells, tissue culture cells and colorectal cells. DNA has been obtained successfully from swabs, saline and sucrose mouthwashes and buffy coat samples.

Where the cells comprise white blood cells, it is preferred that the method further comprises applying whole blood to the solid phase, optionally lysing the red blood cells therefrom, optionally washing the solid phase to remove contaminants and obtaining the cell lysate from the blood cells. The whole blood can be fresh or frozen. Blood containing Na/EDTA, K/EDTA, and citrated blood all give similar yields. A 100 $\mu$l sample of whole blood gives a yield of approximately 2–5 $\mu$g of nucleic acids, a 500 $\mu$l sample gives a yield of approximately 15–40 $\mu$g of nucleic acids and a 10 ml sample gives a yield of approximately 200–400 μg of nucleic acids.

It is preferred that the nucleic acid comprises a polynucleotide.

While the method is applicable to any nucleic acid, it is preferred that that the nucleic acid comprises DNA, especially genomic DNA.

It is preferred that the method be conducted without any centrifugation steps.

It is preferred that the method be conducted substantially in the absence of a chaotrope.

This method is particularly useful for the extraction of genomic DNA from whole blood. This method can be conducted in a single vessel, and does not require any centrifugation steps, therefore making the method suitable for automation. One suitable method for extracting genomic DNA from a whole blood sample involves the following steps:

i) Whole blood is charged into a column containing one or more (preferably 4 standard depth) of GF/D variant filters (Whatman International Ltd, Maidstone, UK). This arrangement of glass fiber filters has been found to be of a sufficient depth to effect separation of the white blood cells from other components of whole blood cells in the downstream processing, separation of the genomic DNA from other material;

ii) A red blood cell-lysis solution is delivered to the column in order to lyse red blood cells;

iii) The red blood cell-lysis solution is drawn through the filters leaving white blood cells entrapped within the filter;

iv) White cell-lysis solution is delivered to the column;

v) The white cell-lysis solution is drawn through the filters. It is believed that DNA from the white blood cells forms an association with the glass fiber filters. It is apparent that ionic interaction is minimal, and accordingly it appears that there is a physical retarding of the movement of the DNA down the filter;

vi) A low salt buffer is delivered to the column and washed through. The DNA remains associated with the glass fiber filter;

vii) Further low salt buffer is delivered into the column. This is then heated at a temperature and for a sufficient time to release the DNA from the filter. Preferably, the column is heated to a temperature within the range 78–90° C. (usually 82° C.) for a time of approximately 50 minutes;

viii) DNA is eluted in the low salt buffer. The DNA is of multiplex PCR quality.

While it is indicated in this preferred method that genomic DNA is the desired target compound, it is possible to use the method of the present invention to isolate RNA from an RNA-containing sample.

It will also be appreciated to those skilled in the art of the invention that whole blood may be subjected to a red blood cell lysis solution in a separate vessel prior to transfer of the mixture to the filter. Typical red blood cell lysis solutions that may be used in the method of the invention include those set out in Table 2.

A kit according to a preferred embodiment of the present invention comprises:

(a) an apparatus comprising a filter supported by a support, wherein the filter composition and dimensions are selected so that the filter is capable of retaining the cells and the nucleic acid;

(b) one or more solutions selected from a red cell lysis solution, a solution for rupturing intact whole cells to leave condensed nuclear material, a lysis solution for lysing nuclear material and an elution solution.

The filter may be supported in or on the support or may form an integral part of the support.

The support may be, for example, any tube or column made from plastics, glass or any other suitable material which does not interfere with the nucleotide separation process. The filter supported on the support may be held in place by a glass frit. This prevents movement of the filter, which may otherwise occur when the sample comprising cells or any other solution is applied to the filter.

TABLE 2

Solutions.

| Reference | Vol Blood | Vol Lysis Solution | Composition | Treatment |
|---|---|---|---|---|
| Millar et al (1988) N.A.R 16:1215 | | 3 ml | 10 mM Tris-HCL pH 8.2 400 mM NaCl 2 mM EDTA | Treat o/n Prot K |
| Nelson & Krawetz (1992) Anal Biochem 207:197–201 | 1 Vol | 5 Vol | 17 mM Tris-HCl pH 7.65 140 mM $NH_4Cl$ | 37° C. for 5 min |
| Ramirez-Solis et al (1992) Anal Biochem 201:331–335 | 1 ml | 3 ml | 155 mM $NH_4Cl$ 10 mM $NaHCO_3$ | 4° C. for 10–15 min |
| Douglas et al (1992) Anal Biochem 201:362–365 | 1 ml | 1 ml of 2× RBC lysis | 1×: 11% sucrose 10 mM $MgCl_2$ 10 mM Tris-HCl pH 7.5 1% Triton X-100 | pellet and wash with 1× |
| Linblom and Holmlund (1988) Gene Anal Techn 5:97–101 | 5 ml | 10 ml | 1% Triton X-100 320 mM sucrose 1 mM Tris-HCl pH 7.5 5 mM $MgCl_2$ | pellet/ urea and phenol |
| | 0.2–2 ml | 20 ml | 20 mM Tris-HCl pH 8.0 5 mM EDTA | Used with Leukosorb type filler |
| Herrmann and Frischauf (1987) in Guide to Molecular Cloning p 180–183 | 10 ml | 30 ml | 155 mM $NH_4Cl$ 10 mM $NH_4CO_3$ 0.1 mM EDTA | ice 15 min, spin |

In another embodiment of the present invention, a technique is utilized which permits, but does not require, elution of the isolated nucleic acid, and most generally provides a medium for storage and subsequent analysis of the genetic material, such as an FTA card. Preferably, the medium includes a matrix for immobilizing a genetic material thereon and allowing subsequent elution of the genetic material therefrom and an integrity maintenance provider for preserving the matrix. A coating is functionally associated with the matrix for enabling cellular lysis and releasing the genetic material from the lysed cells, while stabilizing the immobilized released genetic material. A method is also provided of storing a genetic material most generally including the steps of immobilizing a genetic material on the matrix which allows subsequent elution of the genetic material and lysing cells and releasing the genetic material from the lysed cells while stabilizing the immobilized released genetic material, and an indicator capable of generating a signal when the nucleic acid bonds to the substrate. The genetic material can then be analyzed in solution as opposed to being immobilized on the matrix. The present invention is well suited for various novel uses of the technology. More specifically, the present invention provides a product able to (1) identify the presence of nucleic acid on a substrate and do so rapidly; (2) maintain the integrity of the substrate; and (3) be used in novel embodiments which take advantage of these improvements.

The chemical composition of the substrate facilitates the lysis of whole cells and the subsequent capture of the released nucleic acids. The chemical composition further aids in their long term storage. The composition of the substrate is such that the rapid purification of the captured nucleic acid can be carried out. That is, the substrate itself allows for the release of nucleic acid by an elution step thereby providing a soluble nucleic acid fraction. As discussed in more detail below and exemplified in the following examples, the present invention is most efficient with regard to elution of total DNA from the sample. However, nucleic acid and nucleic acid populations can be specifically eluted.

The substrate, when processed in accordance with the invention to provide a nucleic acid eluting filter material, provides a number of advantages and applications. Thus, use of the substrate of the present invention provides advantages of identification and quantification of nucleic acid-containing biological fluids as well as multiple processing or fluids.

Figure 23:
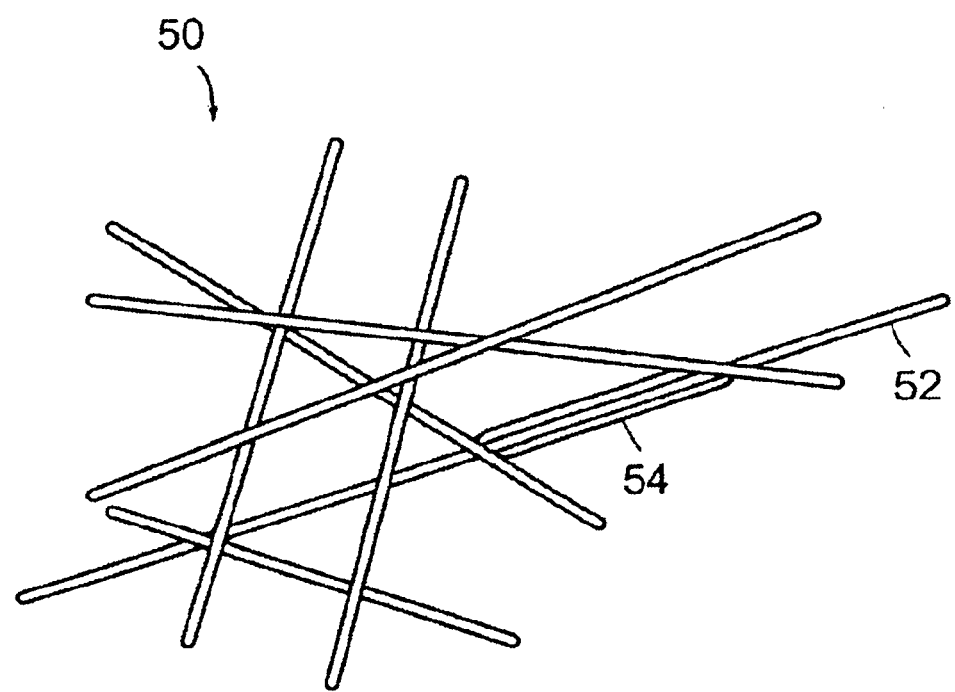
FIG. 23 is a cross-sectional depiction of a filter membrane (50) made in accordance with the present invention.

The filter material preferably utilized in the present invention, is generally shown at 50 in FIG. 23, and includes the following components:

(i) a suitable matrix, preferably a filter membrane 52;
(ii) a chemical coating 54; and
(iii) an integrity maintenance provider.

Contact of the filter media with the chemical coating solution produces the filter membrane of the invention. If the membrane is fibrous, this coating is a coating of the filter fibers, not the filter surface. Alternatively, the coating can impregnate the fibers.

Preferably, the matrix of the present invention is a porous material in the for of a filter membrane.

The term "filter membrane" or "matrix" as used herein means a porous material or filter media formed, either fully or partly from glass, silica or quartz, including their fibers or derivatives thereof, but is not limited to such materials. Other materials from which the filter membrane can be composed also include cellulose-based (nitrocellulose or carboxymethylcellulose papers), hydrophilic polymers including synthetic hydrophilic polymers (e.g. polyester, polyamide, carbohydrate polymers), polytetrafluoroethylene, and porous ceramics.

The media used for the filter membrane of the invention includes any material that does not inhibit the sorption of the chemical coating solution and which does not inhibit the storage, elution and subsequent analysis of nucleic acid-containing material added to it. This includes flat dry matrices or a matrix combined with a binder. It is preferred that the filter membrane of the invention be of a porous nature to facilitate immobilization of nucleic acid. Unlike prior art supports, the support of the present invention allows for elution of the genetic material therefrom in a state that allows for subsequent analysis. Unexpectedly, such elution is a time efficient step thereby providing for almost immediate analysis.

The term "chemical coating solution" as used herein means a chemical composition that is able to sorb to the aforementioned filter membrane. The composition of the chemical coating solution is preferably as described and relates to that outlined in U.S. Pat. Nos. 5,756,126, 5,807,527, and 5,496,562. Adsorption of the chemical coating solution to the selected filter membrane results in the formation of the filter membrane of the invention.

More specifically, the preferred chemical coating solution includes a protein denaturing agent and a free radical trap. The denaturing reagent can be a surfactant that will denature proteins and the majority of any pathogenic organisms in the sample. Anionic detergents are examples of such denaturing reagents. The chemical solution can include a weak base, a chelating agent, and the anionic surfactant or detergent, and optionally uric acid and urate salt as discussed in detail in the above-cited U.S. Pat. No. 5,807,527. More preferably, the weak base can be a Tris, trishydroxymethyl methane, either as a free base or as the carbonate, and the chelating agent can be EDTA, and the anionic detergent can be sodium dodecyl sulfate. Other coatings having similar function can also be utilized in accordance with the present invention.

Alternatively, the substrate consists of a matrix and an anionic detergent affixed thereto. The anionic detergent can be selected from the group including sodium dodecyl sulfate (SDS). SDS can be obtained in various forms, such as the $C_{12}$ form and the lauryl sulfate. Other anionic detergents can be used, such as alky aryl sulphonates, sodium tetradecyl-sulphate long chain (fatty) alcohol sulphates, sodium 2-ethylhexysulphate olefine sulphates, sulphosuccinates or phosphate esters. The anionic detergent, such as the SDS, can be applied to the filter matrix at varying concentrations.

Generally, 5%–10% SDS can be used in accordance with the present invention. For example, increased concentrations of SDS, up to 10%, which cannot be accommodated within an FTA cocktail, as set forth in the prior art patents discussed above, provided greater critical micelle concentration, which generates greater lysing capability and thus greater yield of target nucleic acid, as demonstrated in the example section set forth below. A definite optimum SDS concentration is achieved in the 5–7.5% SDS concentration range for coating particular glass microfiber in order to enrich for and purify different plasmid populations directly from liquid cultures in a multi-well format, such formats being well known in the art.

The term "functionally associated with" means that the coating is disposed, sorbed, or otherwise associated with the support of the present invention such that the support and coating function together to immobilize nucleic acid thereon through an action of cellular lysis of cells presented to the support. That is, the coating can be adsorbed, absorbed, coated over, or otherwise disposed in functional relationship with the media. For example, the support, in the form of a filter membrane, can be disposed in a solution containing the chemical solution. As stated above, the support or the present invention is preferably a porous filter media and can be in the form of a flat, dry media. The media can be combined with a binder, some examples of binders well-known in the art being polyvinylacrylamide, polyvinylacrylate, polyvinylalcohol, and gelatin.

The matrix of the present invention can be capable of releasing the generic material immobilized thereto by a heat elution. Preferably, such a heat elution is accomplished by the exposure of the support having the genetic material stored thereon to heated water, the water being nuclease free. This capacity to allow for elution characterizes the various support materials of the present invention.

The filter membrane of the invention is such that at any point during a storage regime, it allows for the rapid purification of immobilized nucleic acid. The immobilized nucleic acid is collected in the form of a soluble fraction following a simplified elution process, during which immobilized nucleic acid is released from the filter membrane of the invention. The filter membrane of the invention yields nucleic acid of sufficient quality that it does not impair downstream analyses such as polymerase chain reaction (PCR), ligase chain reaction (LCR), transcription mediated amplification (TMA), reverse transcriptase initiated PCR, DNA or RNA hybridization techniques, sequencing, and the like.

Nucleic acid immobilization to a solid support, although a suitable template for singular PCR reactions, cannot be measured or detected by traditional techniques such as optical density or fluorescence. Nucleic acid must be in solution for those techniques. Other post-purification techniques wherein nucleic acid is desired in the soluble form include cloning, hybridization protection assay, bacterial transformation, mammalian transfection, transcription-mediated amplification, and other such methods. The present invention provides nucleic acid in such a soluble form. Additionally, the signal generated by the indicator of the present invention provides positive identification of the presence of nucleic acid on the substrate.

The source of the nucleic acid can be a biological sample containing whole cells. The whole cells can be, but are not restricted to, blood, bacterial culture, bacterial colonies, saliva, urine, drinking water, plasma, stool samples, and sputum. The samples can be collected by various means known in the art, transported to the substrate, and then applied thereto. Alternatively, the substrate can be in the form of a sampling device, such as a swab, sheet material, ball, or the like and the sample can be obtained directly from the source. In other words, the substrate can be in the form of a device which can swipe or otherwise obtain the cell sample from a source. The source can be a sample tube containing a liquid sample; an organ, such as a mouth, ear, or other part of a human or animal; a sample pool, such as a blood sample at a crime scene or the like; whole blood or leukocyte-reduced blood; or other various sources of cells known in the scientific, forensic, and other arts.

Additionally, the fibrous filter matrix of the present invention can be manufactured in various forms. For example, the fibrous filter matrix can be manufactured in a sheet form, which allows for it to be in various formats such as multi-well plates, spin tubes, slides, cartridges, swabs, and pads.

The term "integrity maintainer" or "integrity maintenance means" as used herein means a sealable member that prevents degradation and/or loss of the matrix. Preferably, the integrity maintainer of the present invention creates an air tight seal, thus preventing air, bacteria or other contaminants from coming into contact with the matrix and purified nucleic acid. The integrity maintainer can be in the form of a plastic bag, with or without a seal, cellophane, a sealable container, parafilm and the like.

The integrity maintainer can open to allow application of a sample onto the matrix. It is then closed and sealed thereby containing the substrates. Accordingly, if the substrate ages and becomes brittle, it is contained and not lost. Alternatively, the integrity maintainer can be applied over the substrate after the sample is applied.

The present invention provides a method for isolating and archiving nucleic acid by the general steps of applying a nucleic acid sample to a substrate consisting of the coating fixed to the matrix, the substrate physically capturing the nucleic acid, and then bonding the nucleic acid to the substrate. Then a signal is generated when the nucleic acid bonds to the substrate. The bonding step is achieved by heating the substrate having nucleic acid applied thereto, by the method discussed above.

The applying step can be achieved by applying whole cells to the substrate. The substrate itself actually induces the lysing of the cells thereby releasing the nucleic acid into the substrate. By being a porous substrate, the substrate presents a vast surface area upon which the nucleic acid is bound.

A washing step, such as with various buffers set forth in the example section, but not limited thereto, can be achieved and is done after cell lysis. The substrate then physically captures the nucleic acid within the intrastaces thereof.

The bound nucleic acid can be released from the substrate for further processing and analysis. The release is achieved by washing steps at elevated temperature, as demonstrated in the examples below.

Unexpectedly, enrichment for different populations of nucleic acids from the same cell source can be achieved using incremental temperature regimes. For example, plasma DNA can be isolated and enriched from bacterial colonies using the substrate of the present invention. Populations, such as larger populations of supercoiled plasmid, followed by nicked plasmid and finally by linear plasmid migrating to the top of the isolating gel can be achieved utilizing incremental increases in incubation temperature.

It is known that the FTA coating cocktail of the prior art contains 2% SDS. It is unlikely that this percentage can be increased due to saturation points when in conjunction with other components of the cocktail. This limits the lysing capability of the FTA coating filters of the prior art as a critical micelle concentration of SDS can be easily reached when presented with large numbers of cells, such as with a bacterial colony. Therefore, substrates containing a greater concentration of the lytic agent, the anionic detergent, enable greater lysing capability and in turn, greater nucleic acid recoveries. This is demonstrated in the examples set forth below.

The filter membrane of the invention can possess the same chemical component as FTA that enables the action of cellular lysis and nucleic acid release upon sample application. The chemical component ensures nucleic acid stability via protein denaturants, a free radical trap, and viral/microbial inhibitors. The difference between prior art FTA solid supports and the filter membrane of the invention is that the base solid support, or filter, has been changed compared to that described for FTA products. This change in solid support material, or filter, has enabled, upon a simplified heat elution step, bound nucleic acid to be removed from the filter membrane of the invention whereas it cannot be removed from FTA solid support (see Del Rio et al. (1995) Bio Techniques, vol. 20: 970–974). The nucleic acid released from the filter membrane of the invention is thus presented as a soluble fraction that can be readily aliquoted to multiple downstream processes such as PCR amplification. The eluted soluble nucleic acid can also be entered into techniques where soluble nucleic acid is a necessity, such as optical density analysis, fluorescence detection, cloning, transformation, and the like. This added technique of elution enables high throughput multiple processing regimes, such as genotyping.

The present invention can find utility in many areas of genomics. For example, the present invention provides the capability to elute bound genetic material for the rapid purification of the genetic material to be utilized in any number of forensic applications, such as identification, paternity/maternity identification, and at the scene of a crime.

Prisoners from many countries are required to give a genetic sample (blood or buccal sample) for DNA fingerprinting purposes. The use of the present invention provides a means for the long-term storage of prisoner genetic material. If necessary, the genetic material can be tested as soon as it is taken or many years after storage. The generic material can be obtained as either a soluble or solid phase fraction once isolated on the filter media of the present invention.

The present invention can be utilized for paternity/maternity identification having a particular use for a mother or hospital wherein a newborn has been mislaid in the hospital. The rapid ability of the present invention to provide for a purified genetic sample provides even greater utility in such instances where a speedy identification of a mislaid child would be most propitious.

The present invention is a significant contribution to current methodologies for the preparation of soluble genetic material, which are otherwise time-consuming and often result in inadequate template that is damaged or contaminated. The present invention provides high yield of purified genetic material of superior quality in less than twenty minutes of laboratory time. The rapidly purified genetic material can be utilized for any number of food/agricultural applications such as tracing, breeding, identification, and cloning.

The efficiency with which food manufacturers detect pathogenic outbreak in both their livestock and finished product is the measure of a successful company. The use of the present invention as a swab that can be simply pressed against food or the use of a card onto which carcass blood can be spotted enables uses of the present invention to rapidly isolate and detect for the presence of pathogenic genetic material. Time-consuming prior art assay techniques and involved nucleic acid preparations do not need to be performed if the present invention is utilized. Collected pathogenic nucleic acid can be used as a soluble fraction or solid phase fraction with the choice of an elution step.

Tracing carcass material, whether for legal or health issues, enables manufacturers to keep control of their products. At the point of kill in a slaughterhouse, a card utilizing the present invention can be attached to the carcass onto which its blood has been spotted. At the same time, a second card can be spotted with the same blood and kept as an archive at the slaughterhouse. If an identification issue arises for a certain carcass, genetic records on both the carcass and the slaughterhouse can be utilized. If the carcass card is inadvertently removed, identification can still be carried out by simply pressing a carcass flesh onto such a card.

Identifying the desired genes and characteristics that are required for a subsequent generation of a plant or animal requires the time effective and reliable generation of nucleic acid from potential parents. The present invention can be used for the isolation of either soluble or solid phase genetic material to provide effective and reliable results in such a need. Likewise, the present invention, in the form of microplates, a tube or a chip, can be used for the generation and detection of genetic material. The present invention provides methodology for superior template preparation time (whether soluble or solid) and cost-effective archiving.

Pressing a media, in the form of a swab or otherwise, enables the user to pick up any contaminated microbes on food products of any type. Genetic material isolated from the media can then be utilized for any manner of diagnostic procedure depending on whether soluble or solid phase genetic material is required. This analysis can be done almost effectively immediately, as opposed to prior art techniques.

By the use of genetic manipulation techniques, food stuff has been produced with increased size, flavor, ripening, and sugar content. Many countries prohibit the sale of genetically modified food products and therefore require testing to be carried out. Since one is looking for specific genes that generate these characteristics, genetic material is required. The present invention can be used to provide rapid purification of both soluble and solid phase genetic material.

In view of the above, the present invention finds utility in various areas of genomics.

Initial experiments were performed to demonstrate the possibility of utilizing FTA-coated materials such as membranes for the quantitation and detection of DNA. First experiments illustrated that whole cells can be deposited onto FTA-coated membrane such as cellulose nitrate, with cell lysis and nucleic acid binding readily carried out on contact. Immobilized DNA can be detected (and quantified) by the use of a specific and non-specific DNA probe or other signal generators and one of the versions of immunoassay.

There are many liquids in several industries that should not have any biocontamination at point of sale. Also liquids are monitored for increase in biocontamination over time. Liquids may also include biological samples where the presence of microbes may illustrate disease or infection. A sample of a liquid would be added to an FTA coated substrate, cells within the sample, including unwanted bioload, will lyse on contact with nucleic acid fixing instantly. Direct detection with either a general DNA probe, to show the presence of cellular contamination, can be used, or a species specific probe can be employed, and by hybridization identify the presence of unwanted cells from a multicellular sample. This type of system can be utilized in the food industry, with liquids including milk, wine, beer, and juices. In medicine, urine, blood, and stool extract can all be applied to the system with direct detection of the immobilized nucleic acid carried out with species-specific probes. In the environmental industry, drinking water, seawater, and river water can find utility within the proposed system.

A disease such as lupus is characterized by the presence of double stranded DNA (dsDNA) in the bloodstream. A sufferer of lupus will therefore have in their system antibodies that will have been raised to the presence of the dsDNA antigen. Human dsDNA spotted and fixed to an FTA-coated membrane can therefore be utilized as a platform for carrying out direct ELISA if applied sample contains the lupus antibodies. Lengthy immobilization steps in order to carry out "traditional" ELISA are negated with an FTA approach.

For the use of an FTA coated substrate onto which suspected leukodepleted blood is spotted, the nucleic acid component of the sample is affixed to the substrate and is available for direct measurement with a probe such as PEI. If deflection is below a set lower limit then the sample is deemed leukodepleted. Such a system offers great timesaving for blood banks that currently use microscopy for characterizing depletion efficiencies. With a trend more towards leukodepletion of blood at the source rather than bedside, a simple detection methodology is very useful.

In this invention applicants propose that the extraction system of the present invention has several significant advantages compared to both traditional and quantitative PCR leukocyte counting methods.

The measurement of the sample DNA with Pico green fluorescent dye or specific human DNA probes has sensitivity in the range of DNA concentration from 200 pg to 1000 ng. This sensitivity, in combination with the efficacy of the preferred embodiments of the present invention, may qualify to measure DNA in leukoreduced blood samples according to both AABB and European Standards.

The present invention demonstrates an efficiency comparable to flow cytometry for fresh and frozen samples of leukoreduced whole blood, RBC and platelets.

EXAMPLES

Example 1

Preparation of Purified Product Using an Elution Method

DNA extraction from 200 μl of human whole blood was carried out using the present method. The protocol was as follows:

1) Add 200 μl of whole blood to the column, add 1000 μl of red blood cell lysis solution (RBCL), filter to waste.
2) Add 1000 μl RBCL, filter to waste.
3) Add 1000 μl 0.5% SDS, filter to waste.
4) Add 1000 μl $TE^{-1}$, filter to waste.
5) Add 100 μl $TE^{-1}$, filter to waste.
6) Incubate at 90° C. for ten minutes.
7) Add 100 μl $TE^{-1}$, filter to capture DNA solution.

The mean DNA yield for the present method is 30–40 μg per ml of blood. About 80% of the DNA product is greater than 40 kb. The approximate time per cycle is 20 minutes, i.e. significantly faster than presently known methods.

At various stages of the method, the filter and the retentate were analyzed by scanning electron microscopy (SEM) in order to reveal the mechanism of cell retention, DNA retention and DNA release. Samples were fixed with 3% glutaraldehyde and 1% formaldehyde for 24 hours, washed with PIPES buffer, osmiated and gold treated with 25 nm of gold. The results are shown in FIGS. 1 to 9.

Figure 1:
FIG. 1 is an image obtained by scanning electron microscopy (SEM) of the structure of a filter material suitable for use in the present method.
Figure 2:
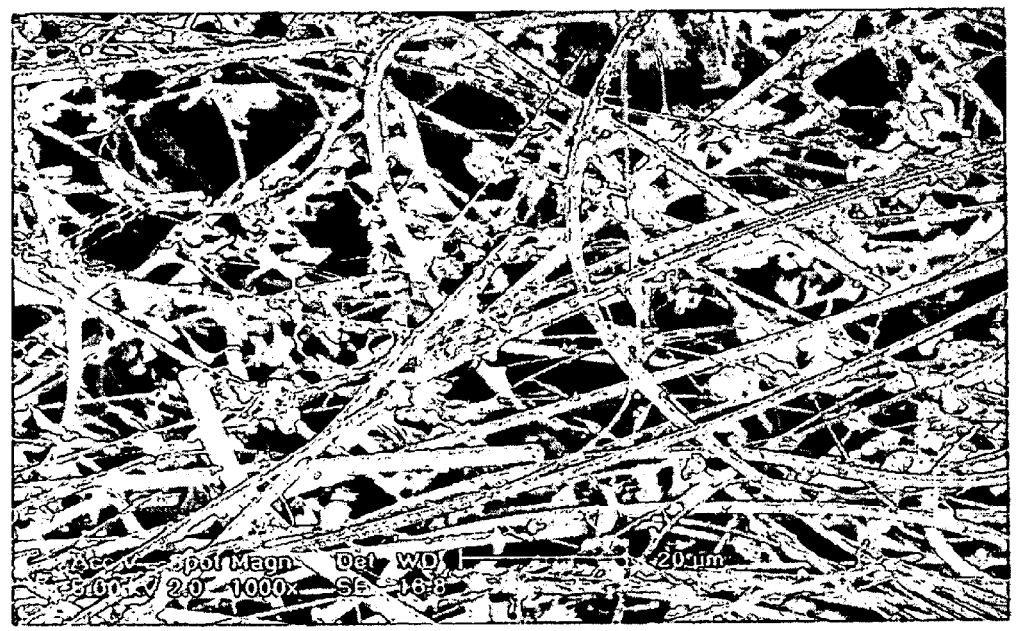
FIG. 2 is an image obtained by SEM of the retained retentate and the filter.
Figure 3:
FIG. 3 is an image obtained by SEM of the retained retentate and a top portion of the filter.
Figure 4:
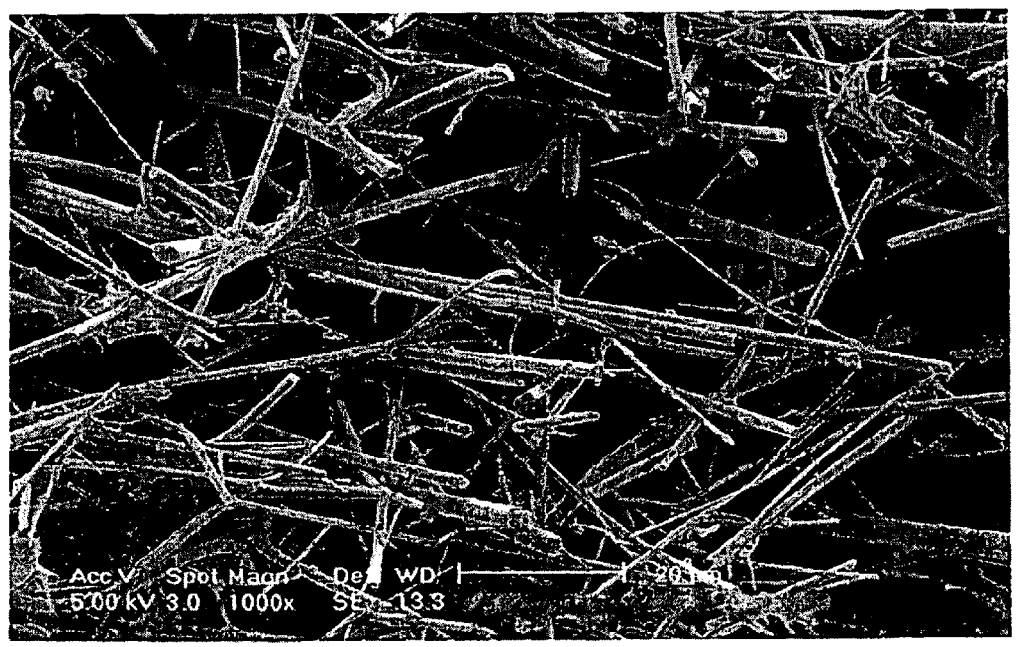
FIG. 4 is an image obtained by SEM of the retained retentate and a lower portion of the filter.
Figure 5:
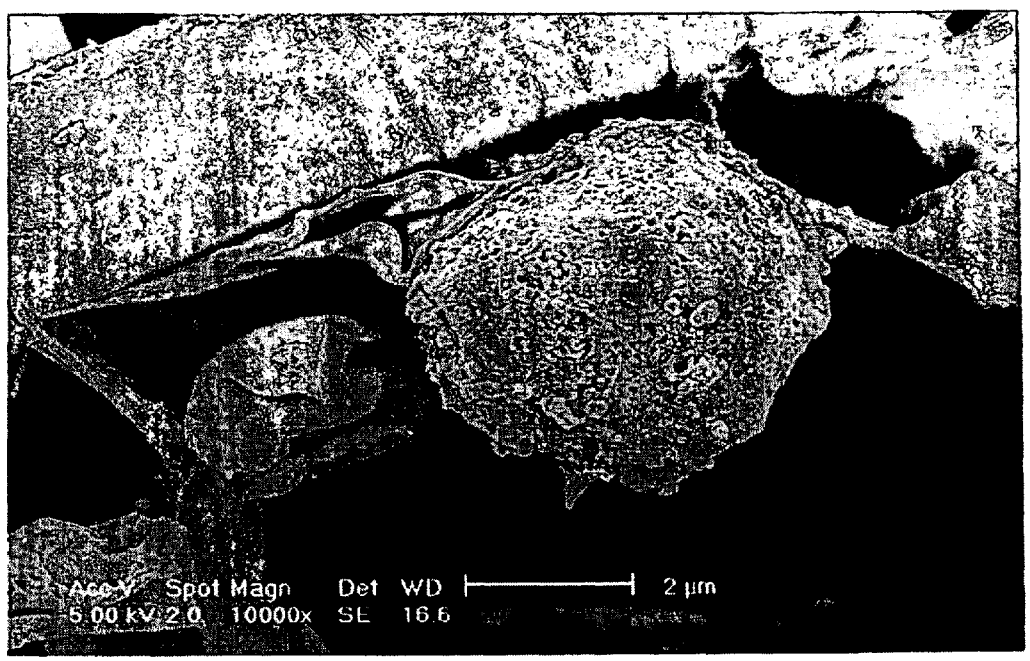
FIG. 5 is an image obtained by SEM of the retentate comprising a damaged white cell which is retained by the filter.
Figure 6:
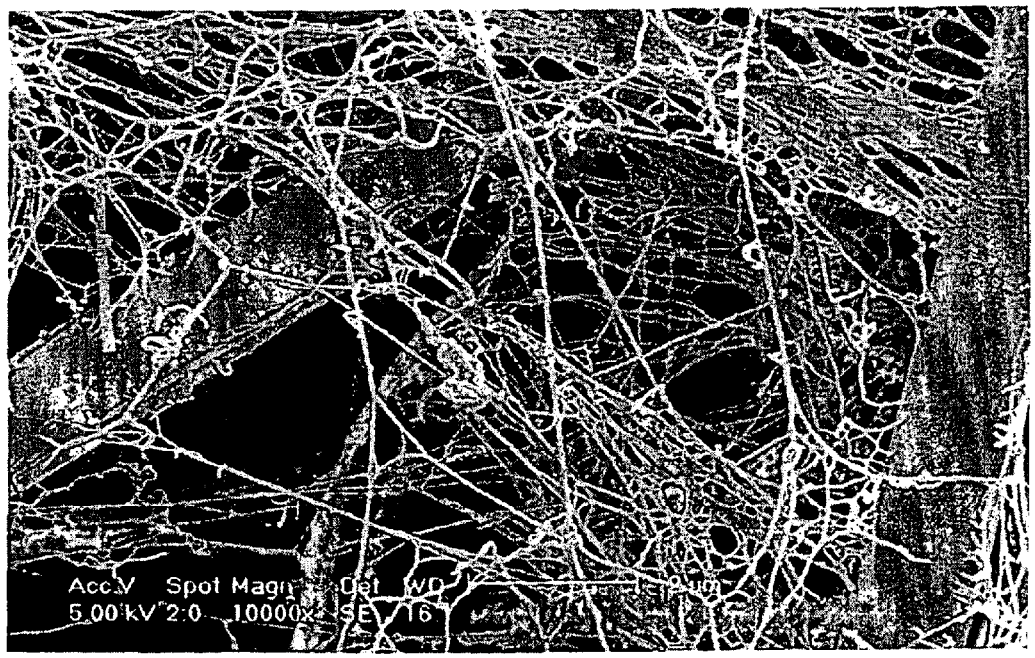
FIG. 6 is an image obtained by SEM of the nucleic acid which is retained by the filter in the form of web.
Figure 7:
FIG. 7 is a close-up image obtained by SEM of the nucleic acid web as it is retained by the filter.

The strands shown by the image in FIG. 7 are approximately 50 nm in diameter. It is thought that each strand is made up of a single DNA strand (less than 1 nm in thickness) and a 25 nm gold coating which encases each DNA strand.

Figure 8:
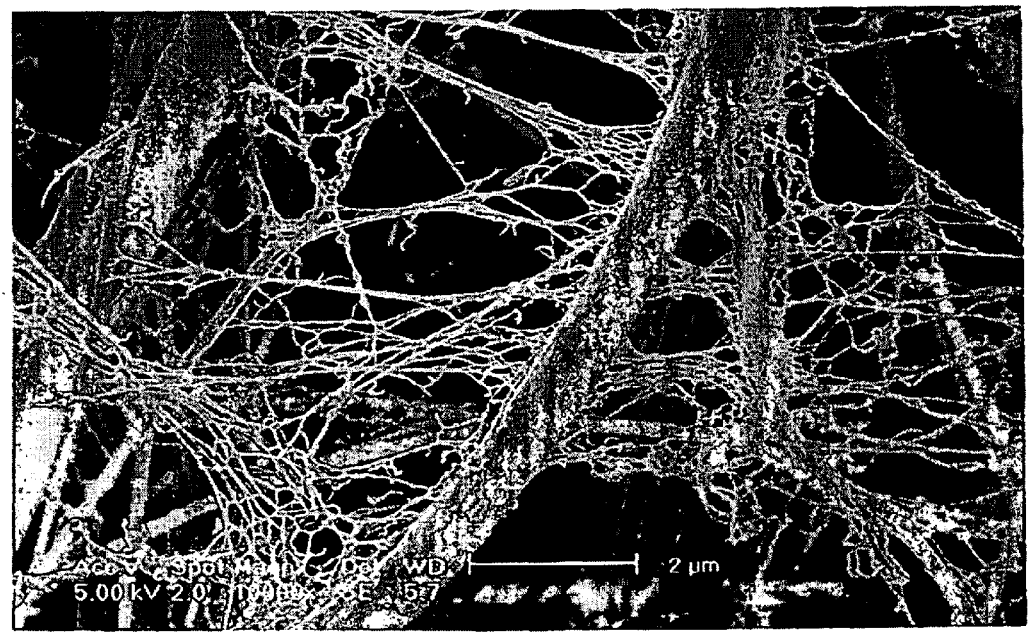
FIG. 8 is an image obtained by SEM of the nucleic acid web and the filter after the optional step of heating and/or incubation prior to elution.

The image in FIG. 8 shows that physically, the nucleic acid web appears to be unchanged after the heating and/or incubation step.

Figure 9:
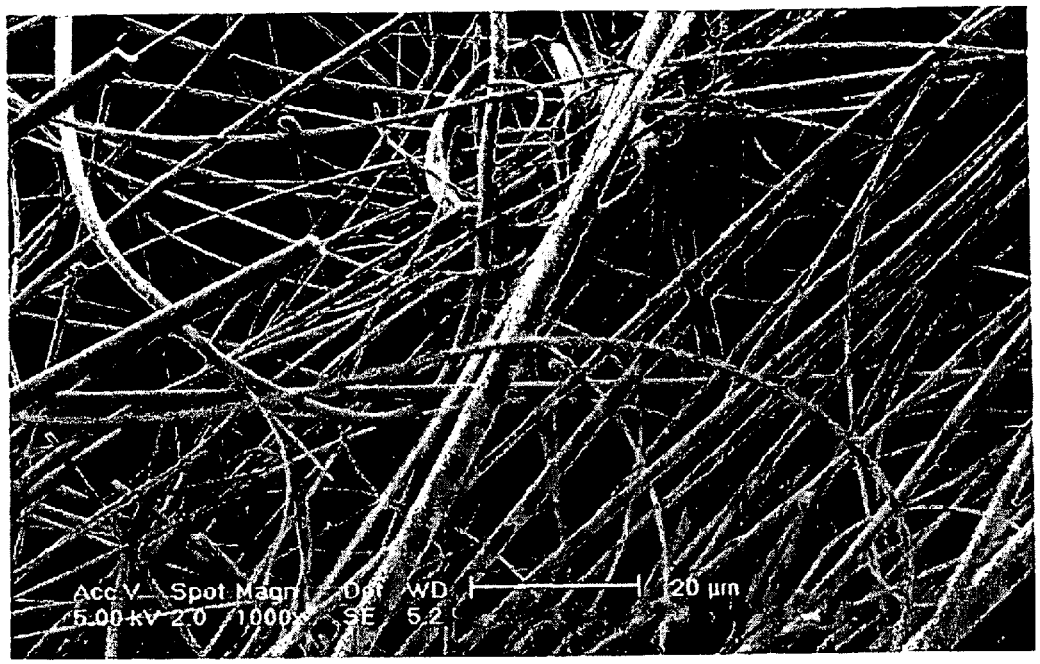
FIG. 9 is an image obtained by SEM of the filter after elution of the nucleic acid.

FIG. 9 shows that the filter is very clean after elution of the nucleic acid.

Scanning spectroscopy analysis of the waste eluant in step 2 (not shown) is a large absorbent peak at 410 μm indicating the presence of heme. At the end of step 2, the retentate is on or in the filter.

Scanning spectroscopy analysis of the waste eluant from step 3 (not shown) shows a large defined absorbance peak at 275 μm indicating the presence of protein. A small peak at 410 μm is visible indicating the presence of heme.

Scanning spectrophotometric analysis of the waste eluant from step 4 (not shown) shows a very small protein peak. No heme peak is observed. No peak is observed at 260 μm indicating that DNA is not present. This is confirmed also by agarose gel analysis.

Scanning spectrophotometric analysis of the final product (not shown) shows a defined absorbance peak at 260 μm indicating that DNA is present. The 260:280 ratio is approximately 1.8. When the DNA is eluted in water, absorbance between 200 and 230 μm is zero indicating that there is no salt present.

Figure 10:
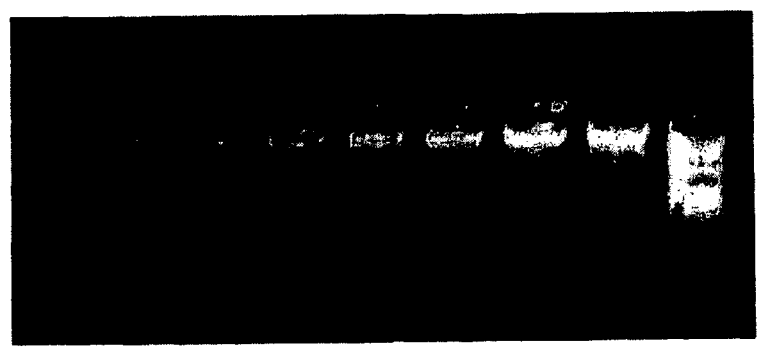
FIG. 10 is an agarose gel analysis of DNA capture from a stack of filters.

Restriction digestion tests suggest that the DNA recovered from this method is predominantly single-stranded (see FIG. 10).

Example 2

Filter Depth for Filter Used in Elution Method

It has hitherto been unknown to use a filter in the dual role of white cell capture and DNA capture. Once the white cells are lysed, it is believed that the filter acts as a depth filter to the DNA. In order to explore this, the following investigation was undertaken.

A number of filters were stacked in an extraction column and DNA was isolated from 500 μl of whole blood in accordance with the following protocol:

1) Add 500 μl of red blood cell lysis solution to the blood and filter to waste.
2) Add 500 μl 0.5% SDS solution and filter to waste.
3) Add 500 μl mM Tris-HCl pH 8.5 and filter to waste.
4) Add 500 μl mM Tris-HCl pH 8.5 and incubate for 50 min at 82° C.
5) Filter and capture DNA eluant.

Prior to the final incubation and elution step the filters were removed and each one eluted and incubated individually. FIG. 10 shows that there seems to be a gradient of DNA capture from the top filter to the bottom one. Lanes 1–8 show the recovery from filters from lowermost to uppermost respectively. This tends to indicate that the filter is physically retarding the DNA rather than binding it.

Figure 11:
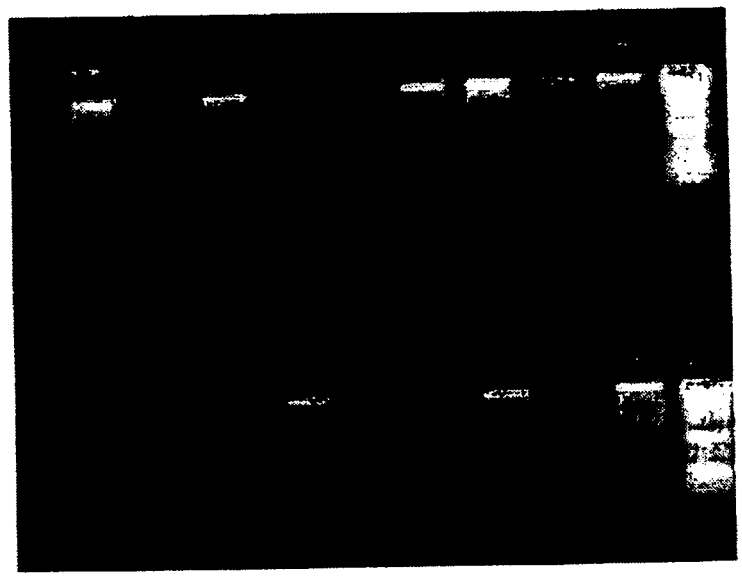
FIG. 11 is an agarose gel analysis of drop-out of DNA levels from various filter arrangements.

The experiment was repeated, but this time small gaps were left at the edges of some of the filters. If the association between the DNA and the filter is entirely chemical then this would have no effect on the gradient of DNA quantity from the top to the bottom filter. FIG. 11 shows that the filter fit should be carefully monitored in the method of the present invention since filters that are not true to the edge of the extraction vessel appear to bind much less DNA. The dropout in DNA levels on these filters had no effect on the capture of DNA filter below. This is further evidence that the method of the present invention involves the physical retardation of DNA rather than a chemical interaction.

Example 3

Filter Depth for Filter Used in Elution Method

Analysis has shown that DNA recovery can be improved within the system by increasing the number of filters within the column. An experiment was performed according to the protocol below to assess the percentage of DNA captured by each subsequent layer of filter by processing whole blood using a 4-layered extraction column.

Protocol

1) Add 200 μl of whole human blood to the 2 ml-extraction vessel.
2) Add 1 ml of RBCL and filter directly to waste.
3) Add a further 1 ml of RBCL and filter directly to waste.
4) Add 1 ml of 0.5% SDS and filter directly to waste.
5) Add 1 ml of $TE^{-1}$ and filter directly to waste.
6) Add 100 μl of $TE^{-1}$ and incubate at 90° C. for 8 minutes.
7) Add 200 μl of $TE^{-1}$ and collect.

The filters were removed prior to the elution step and the DNA collected off each filter separately. The most DNA was recovered from the uppermost filter and the least DNA was recovered from the lowest filter.

Figure 12:
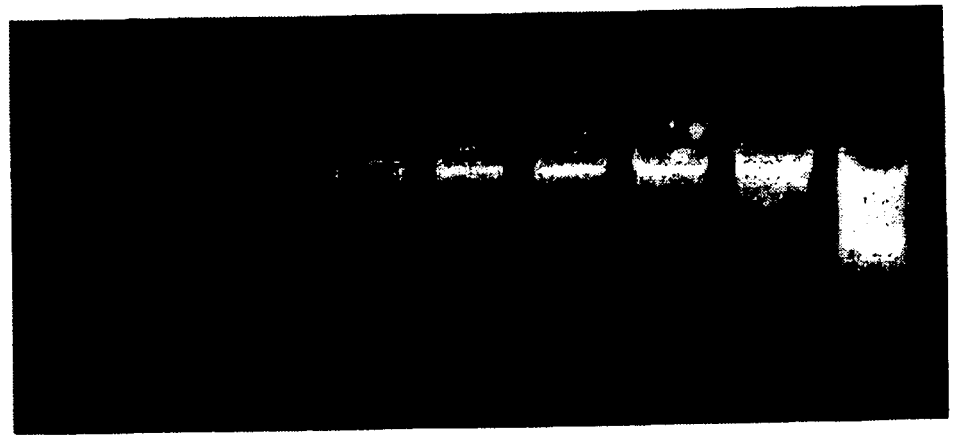
FIG. 12 is an agarose gel photograph showing the proportion of DNA eluted from layers of filters within a system.

FIG. 12 shows an agarose gel photograph showing the results of an experiment to show the proportion of DNA eluted from layers of filters within each system.

Lane
  1 4th filter (Uppermost)
  2 3rd Filter
  3 2nd Filter
  4 1st Filter (Lowest)
  5 Control
  11 1 kb Ladder

Example 4

Salt Environment for Elution Method

Figure 13:
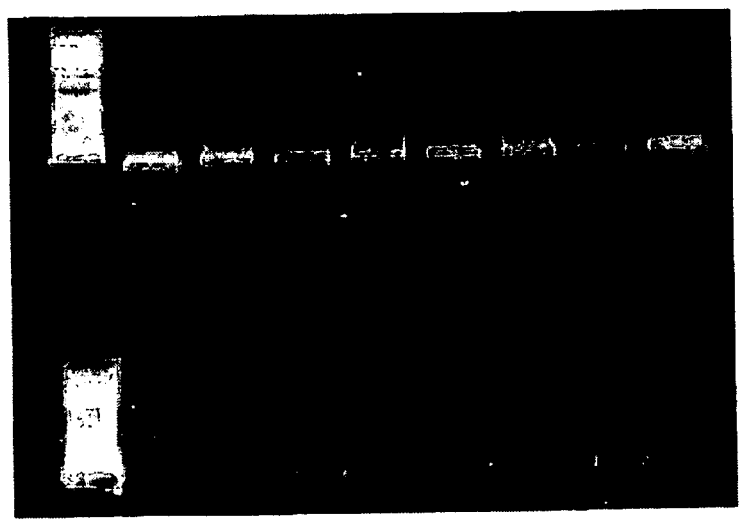
FIG. 13 is an agarose gel analysis of DNA recovery from filters in the presence of 1M TRIS pH 8.5 and 50% ethanol.

In the method according to the present invention, DNA remains bound to the silica during the wash steps in the presence of a 50% ethanol solution. In the method of the present invention DNA remains associated with the filter even in the presence of a low salt buffer. The upper agarose gel in FIG. 13 shows eight 500 µl blood samples recovered by the method of the present invention using 1 mM Tris pH 8.5 in the wash step. The lower gel shows recoveries using 50% ethanol in the wash step. 20 µl of DNA eluant was loaded in each lane.

Figure 14:
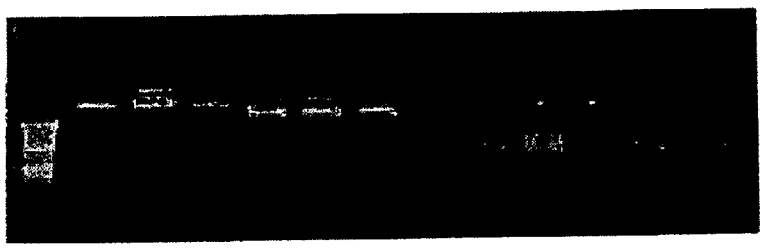
FIG. 14 is an agarose gel analysis of DNA extracted from whole blood and eluted in a range of salt concentrations.

Further experiments using the method of the present invention have shown that DNA can be eluted off the filters in a high salt environment. FIG. 14 shows DNA extracted from 100 µl of whole blood and eluted in a range of salt concentrations. Lanes 1–3 were eluted in 1M KAc, lanes 4–6 in 0.1M, lanes 7–9 in 0.01M, and lanes 10–12 in 1 mM. Each lane was loaded with 3 µl of eluant

Example 5

Incubation Temperature for Elution Method

Figure 15:
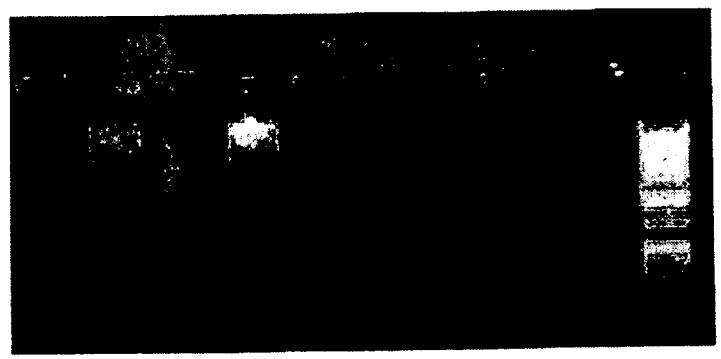
FIG. 15 is an agarose gel analysis of DNA eluted from filters at different elution temperatures.

Temperature and time of incubation prior to elution can be advantageously controlled according to the present invention to enable a high yield of DNA to be obtained. FIG. 15 shows the effect of temperature on DNA yield. Higher temperatures give higher yields and increased DNA shearing. Filters were incubated for 50 mins in water at 90° C. (lanes 1–3), 85° C. (4–6) and 80° C. (79). 20 µl of DNA eluant was loaded in each case.

Example 6

Incubation Temperature and Incubation Time for Elution Method

A number of experiments were carried out to establish the relationship between incubation time, incubation temperature and DNA yield and size. A standard 500 µl extraction was executed according to the protocol of Experiment 2, except that incubation in step 6 was carried out over a range of times and temperatures. The results are shown in Table 3:

TABLE 3

| Incubation temperature/° C. | Time (hrs) | Yield (µg) | Mean size (kb) |
|---|---|---|---|
| 40 | 0.5 | 0 | — |
| 40 | 1.0 | 0 | — |
| 40 | 4.0 | 0.14 | >20 kb |
| 40 | 24.0 | 2.0 | >20 kb |
| 60 | 0.5 | 0.4 | >20 kb |
| 60 | 1.0 | 0.1 | >20 kb |
| 60 | 4.0 | 2.2 | >20 kb |
| 60 | 24.0 | 12.0 | >20 kb |
| 80 | 0.5 | 14.5 | >20 kb |
| 80 | 1.0 | 25.8 | 10 kb |
| 80 | 4.0 | 35.5 | 4 kb |
| 80 | 24.0 | 40.4 | 0.5 kb |
| 100 | 10 | 7.9 | >20 kb |
| 100 | 20 | 14.0 | 5kb |
| 100 | 30 | 12.5 | 5 kb |
| 100 | 40 | 16.5 | 3 kb |
| 100 | 50 | — | — |
| 105 | 10 | 14.0 | >20 kb |
| 105 | 20 | 14.0 | 5 kb |
| 105 | 30 | 6.5 | 2 kb |
| 105 | 40 | 6.0 | 1 kb |
| 105 | 50 | 5.0 | 1 kb |

Figure 20:
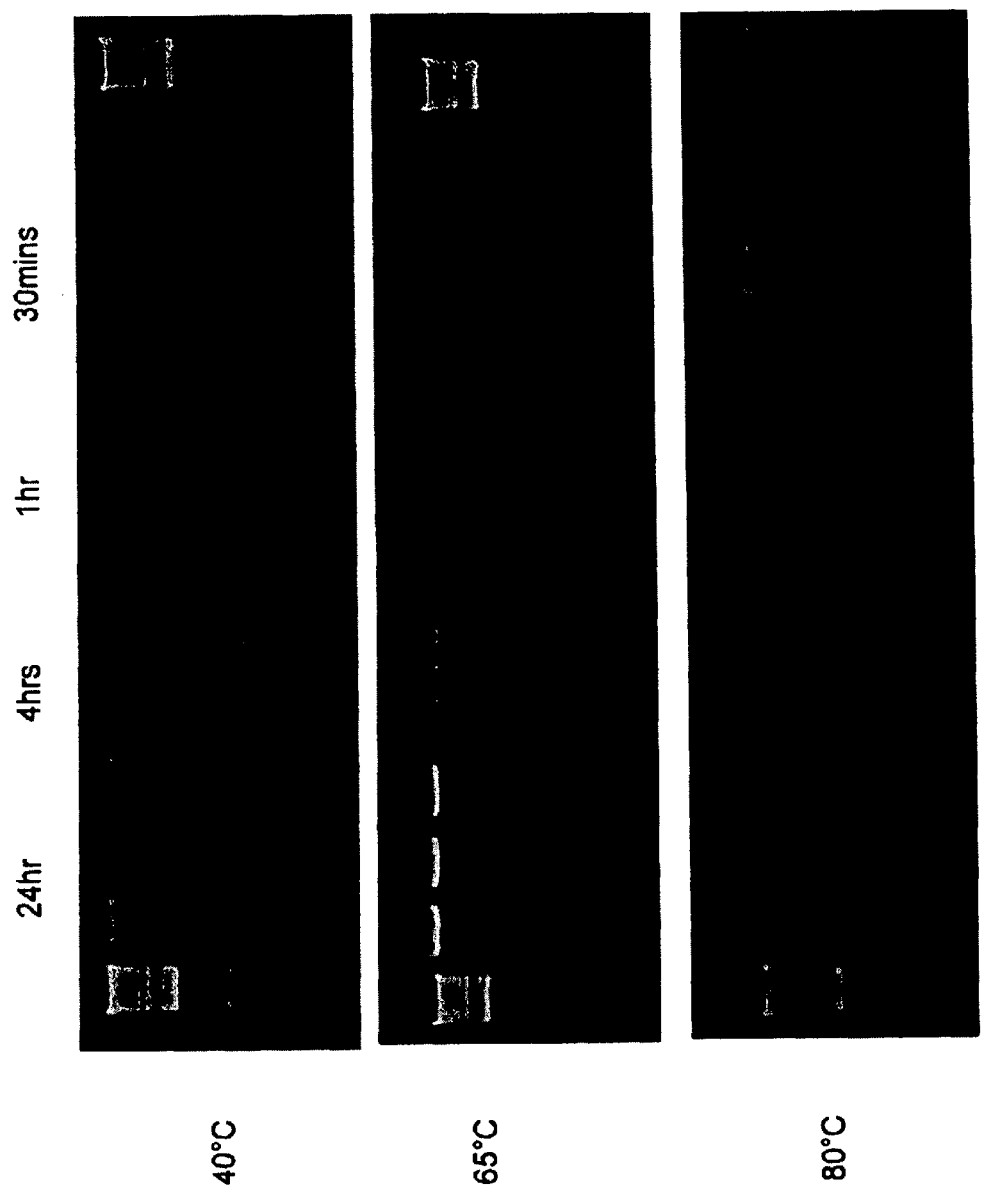
FIG. 20 is an agarose gel photograph showing relationship between incubation time, temperature and DNA yield and size.

A small amount of DNA was obtainable from filters incubated at 40° C. for 24 hours. Agarose gel analysis showed the DNA to be very large. At 60° C. a small amount of very large DNA was obtained after 4 hours. At 80° C. DNA was obtained after 30 minutes. More DNA was yielded over a longer time period however this was progressively more sheared (FIG. 20).

At 105° C. a high yield of DNA comes off the filter in 10 minutes. Any longer than this and the filter becomes visibly dry and the small amount of DNA that is recovered is severely sheared. Incubation at 100° C. gives poor yields over short time periods and sheared DNA when incubated for longer.

Figure 21:
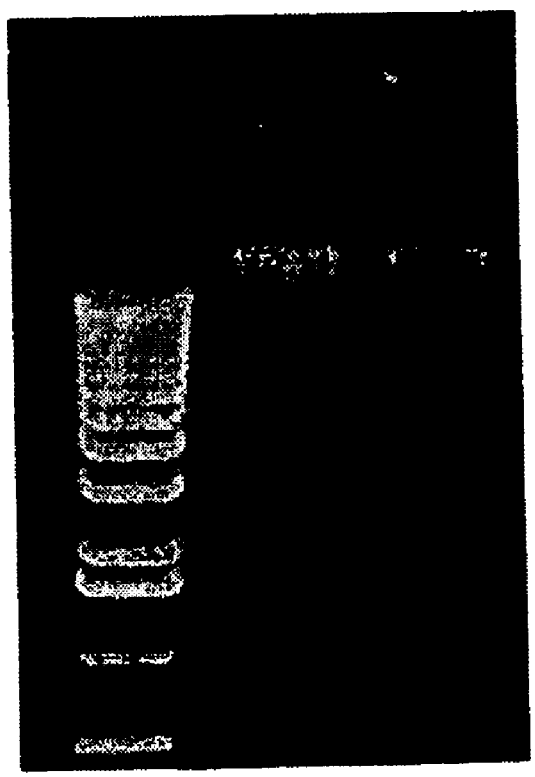
FIG. 21 is an agarose gel photograph showing DNA extracted from 500 μl clinical whole blood samples using the present method.
Figure 22A:
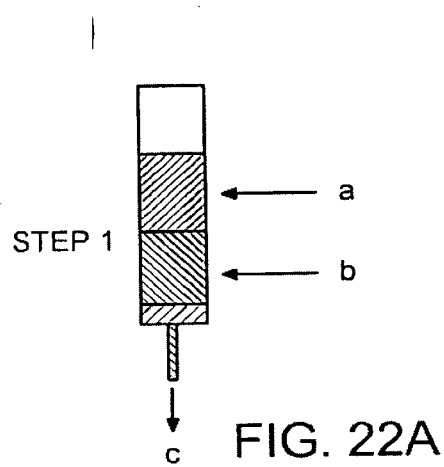
FIGS. 22A–D depict an extraction cartridge during a step-by step diagram of one embodiment of the present method, with FIG. 22A showing Step 1: Nucleated cell lysis.
Figure 22B:
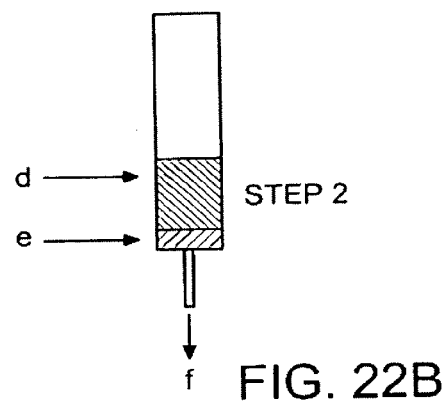
Figure 22C:
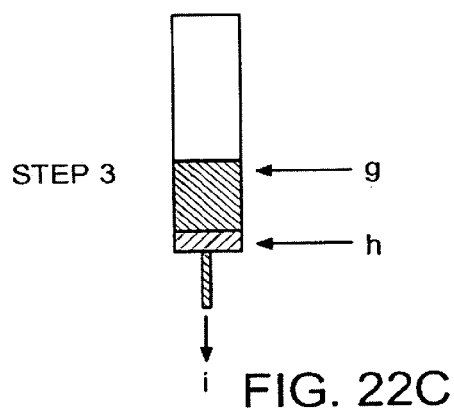
Figure 22D:
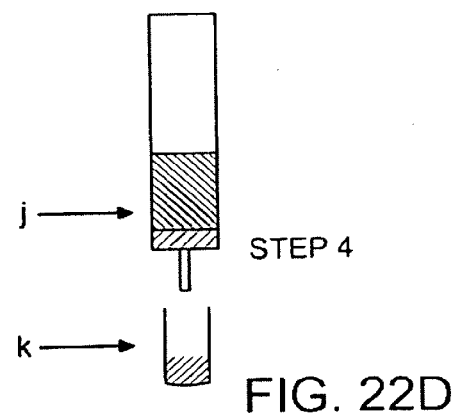

Work with clinical blood samples has shown that incubation at 90° C. for 10 minutes gives a good balance between yield and DNA size giving 30–40 µg of DNA per ml of whole blood. DNA has been shown to be approximately 85%>40 kb in size (FIG. 21). Lane 1 in FIG. 21 shows a 1 kb extended ladder (largest band 40 kb). Lanes 2 and 3 show 10 µl of extracted DNA sample.

Example 7

Heating Step Prior to Elution

An experiment was carried out according to the protocol of Experiment 4 and 7:

Heat was applied to the system to initiate release of the DNA from the filter. The system allowed flexibility with respect to the duration of the heating step, as eluting 18 hours after the heating step resulted in the production of functional genomic DNA with only a small reduction in overall yield being recorded.

Figure 16:
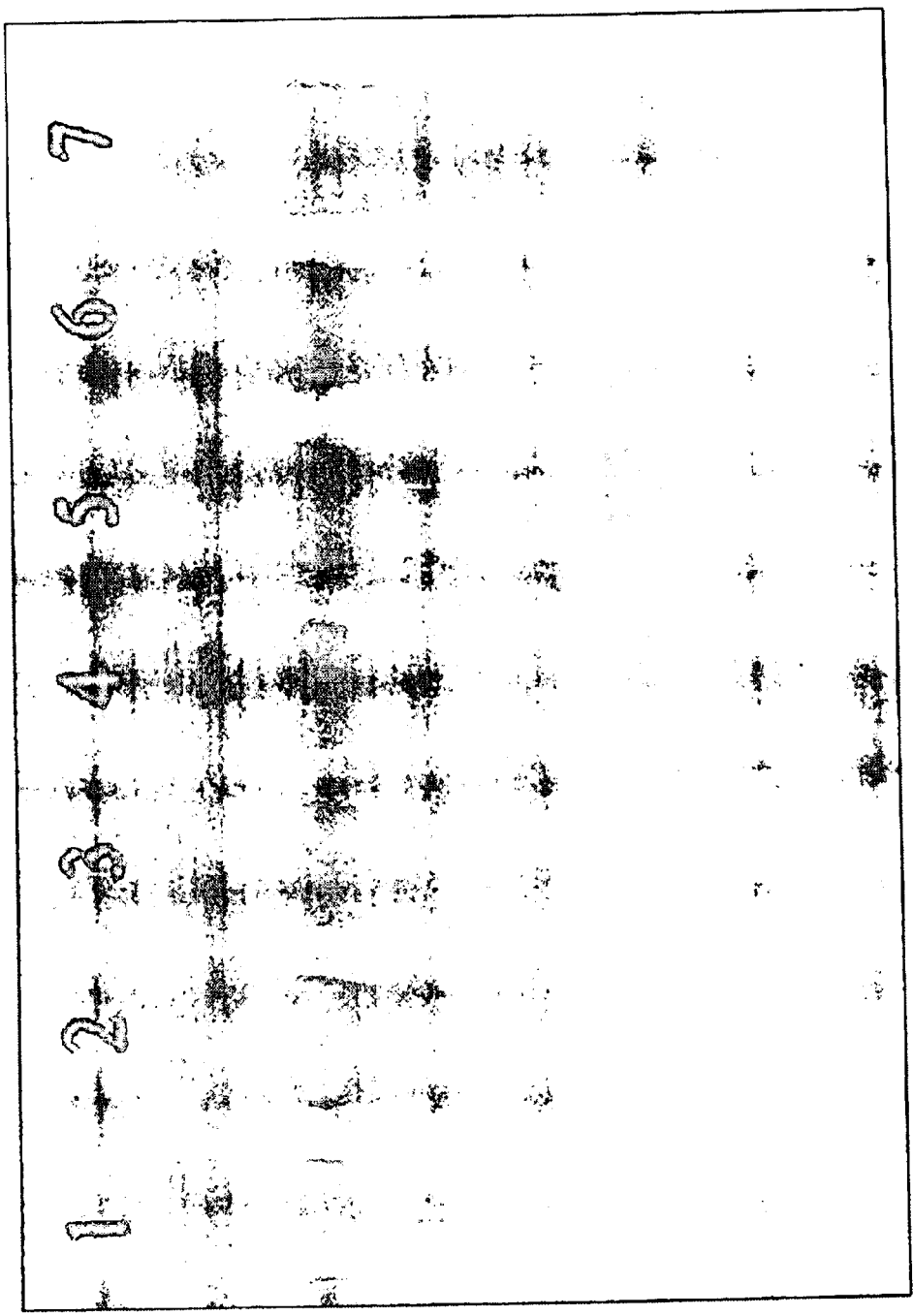
FIG. 16 is an agarose gel photograph showing the results of altering the time of elution post heating.

FIG. 16 shows the comparisons between the time of elution post heating.

Lane 2 heated to 90° C., cooled for 8 hours and eluted at 37° C.

4 heated to 90° C., cooled for 1 hour and eluted.

6 heated to 90° C., eluted at 90° C.

7 1 kb ladder

Example 8

Elution pH

An experiment was set up in accordance with the protocol of Experiments 4, 7 and 8. Ranges of elution buffers with different pH's were used to recover the DNA from the systems. The findings showed that DNA could be eluted over a wide pH range (pH5–pH11), covering both low and high salt buffers, suggesting no direct binding to the matrix.

Figure 17:
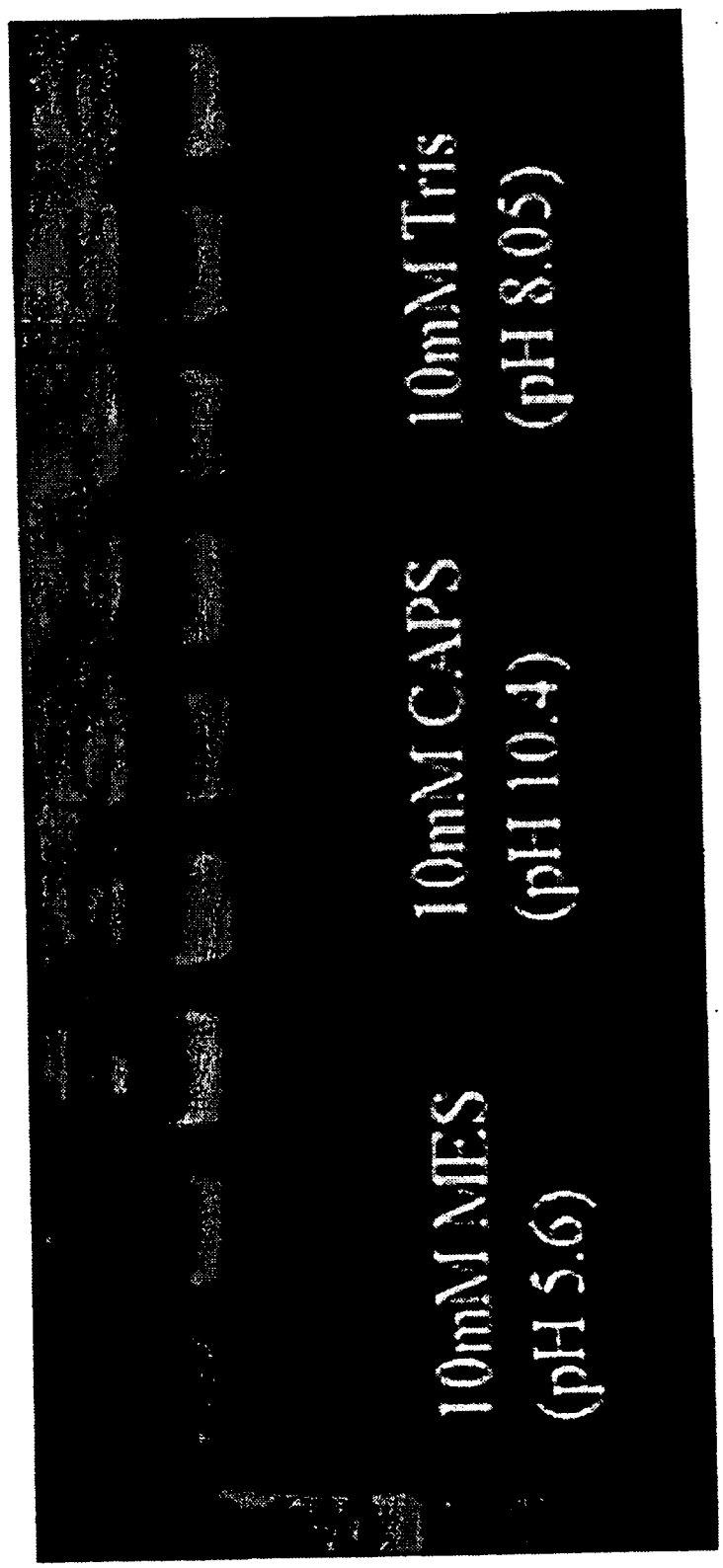
FIG. 17 is an agarose gel photograph showing the results of altering the pH of the elution buffer over the range pH 5.5 to 11.0.

FIG. 17 showing the results of altering the pH of the elution buffer over a range from pH5.5 to pH 11.0.

Lane 1 kb Ladder 2 elution at pH 5.5

4 elution at pH 7.5

6 elution at pH 11.0

Example 9

Elution Volume

An experiment was conducted using the protocol of Experiments 4 and 7 to 10 except that a water eluant was used in step 7 at a volume varying from 10081. The experiment was conducted using one and two filters. The results are shown in Table 4.

TABLE 4

| Number of Filters | Water added (μl) | Mean vol of recovered DNA soln (μl) | Mean DNA conc. (ng/μl) | Mean DNA Yield (μg) |
|---|---|---|---|---|
| 1 | 100 | 168 | 67 | 11.3 |
| 1 | 200 | 254 | 50 | 12.8 |
| 1 | 300 | 358 | 36 | 12.9 |
| 1 | 400 | 455 | 28 | 12.9 |
| 2 | 100 | 170 | 56 | 9.5 |
| 2 | 200 | 252 | 49 | 12.5 |
| 2 | 300 | 356 | 36 | 13.15 |
| 2 | 400 | 469 | 33 | 15.5 |

Optimum yields and concentrations are obtained with the addition of 200 μl of eluant in a single filter column. Very slightly higher DNA yields can be obtained in a two-filter system or with higher volumes of eluant at the expense of DNA concentrations.

Example 10

PCR Analysis of Purified Product After Elution

Analysis of the final solution included repeating the Qiagen PCR assay. This assay amplifies a 1 kb-region using increasing volumes of DNA in a set 50 μl reaction. Although this does not result in equal masses of DNA being added, the aim of this experiment is to determine if any background inhibitors are present. Reactions were set up as shown in Table 5.

TABLE 5

| Reaction | DNA Control | Present DNA Product | Buffer (15 MM Mg) 10 times | dNTPs | Primer 1 | Primer 2 | Taq Polymerase | Water |
|---|---|---|---|---|---|---|---|---|
| 1 | 0 | 0 | 5 | 5 | 0.2 | 0.2 | 0.5 | 39.1 |
| 2 | 0 | 1 | 5 | 5 | 0.2 | 0.2 | 0.5 | 38.1 |
| 3 | 0 | 5 | 5 | 5 | 0.2 | 0.2 | 0.5 | 34.1 |
| 4 | 0 | 10 | 5 | 5 | 0.2 | 0.2 | 0.5 | 29.1 |
| 5 | 0 | 15 | 5 | 5 | 0.2 | 0.2 | 0.5 | 24.1 |
| 6 | 0 | 20 | 5 | 5 | 0.2 | 0.2 | 0.5 | 19.1 |
| 7 | 5 | 0 |   | 5 | 0.2 | 0.2 | 0.5 | 34.1 |

The samples were amplified using the standard service amplification procedure. All the reactions appeared to work in this assay. Therefore, it was concluded that the present DNA product is capable of amplification.

Example 11

SDS Treated Filter (Comparative Experiment) for Elution Method 100 ml of 10% SDS was dried onto Whatman GF/D filters on a hot block. 200 μl whole blood was added to the column, incubated for 1 minute and then eluted to waste. Then, the column was rinsed with 2 ml of water and, again, eluted to waste. In all experiments, there was heme still visible on the filter at the end of the experiment. Redness was visible in all final eluants. All final eluants were frothy indicating the presence of SDS. From these experiments, it was apparent that forcing DNA through SDS treated filters seems to cause extensive DNA shearing. The number of filters (i.e., the depth of the filter) seemed to have no noticeable affect on this.

Experiment 12

Whatman GF/C Filter (Comparative Experiment) for Elution Method

It was found that the composition and dimensions of the Whatman GF/C filters were not suitable for the retention of cells and nucleic acid. The General Protocol set out above was replaced, but this time the stack of 4 GF/D variant filters was replaced with a stack of 4 GF/C filters. 500 μl whole blood was added to the column, followed by 500 μl red blood cell lysis solution. An attempt was made to filter the filtrate to waste, however, the filter became blocked almost immediately. It was apparent that the dimensions of the GF/C filter do not enable the retention cells therein. It is believed that the GF/C filter acts as an absolute barrier to the cells in the absence of a chaotrope.

Example 13

Detection of Fixed DNA on FTA Membranes

Human white blood cells and purified DNA were used as samples to load onto pieces of FTA-treated membrane for an ELISA assay based on the ionic interaction between polyethyleneimine-peroxidase conjugate (PEI-PO) and DNA.

The goal of the experiment was to confirm that DNA could be attached to the FTA membrane for subsequent detection and to confirm that DNA could be released from the cell and attached to a membrane firmly enough for following detection.

Materials and Protocol

Four membranes were utilized; the membranes are as follows:

1. Nitrocellulose membrane, pore size 0.2 μm, Schieicher & Schull; 2. Nylon membrane, pore size 0.2 μm, Osmonics; 3. Nylon membrane, pore size 1.2 μm, Osmonics; and 4. FTA-glass, grade F572-08, Whatman (used for comparison).

The membranes were soaked with the FTA solution for two hours at room temperature with gentle agitation, dried completely at room temperature, and baked at 80° C. for one hour.

DNA Samples of WBC at $5 \times 10^3$ cells/μl, WBC at 5 cells/μl, and DNA at 2 μg/μl were used.

Protocol

All assay steps were performed in one 96 well plate. The circles of each membrane, 0.5 mm in diameter, were put on the bottom of the wells. DNA samples of 3 µl per well were loaded, in duplicate. Then the plate was subsequently blocked with PBS/BSA/Tween-20 solution, incubated with a polyethyleneimine-peroxidase conjugate, washed with PBS/BSA/Tween-20 solution, and finally incubated with different substrates for peroxidase to develop colored soluble or insoluble products.

Results

Figure 24:
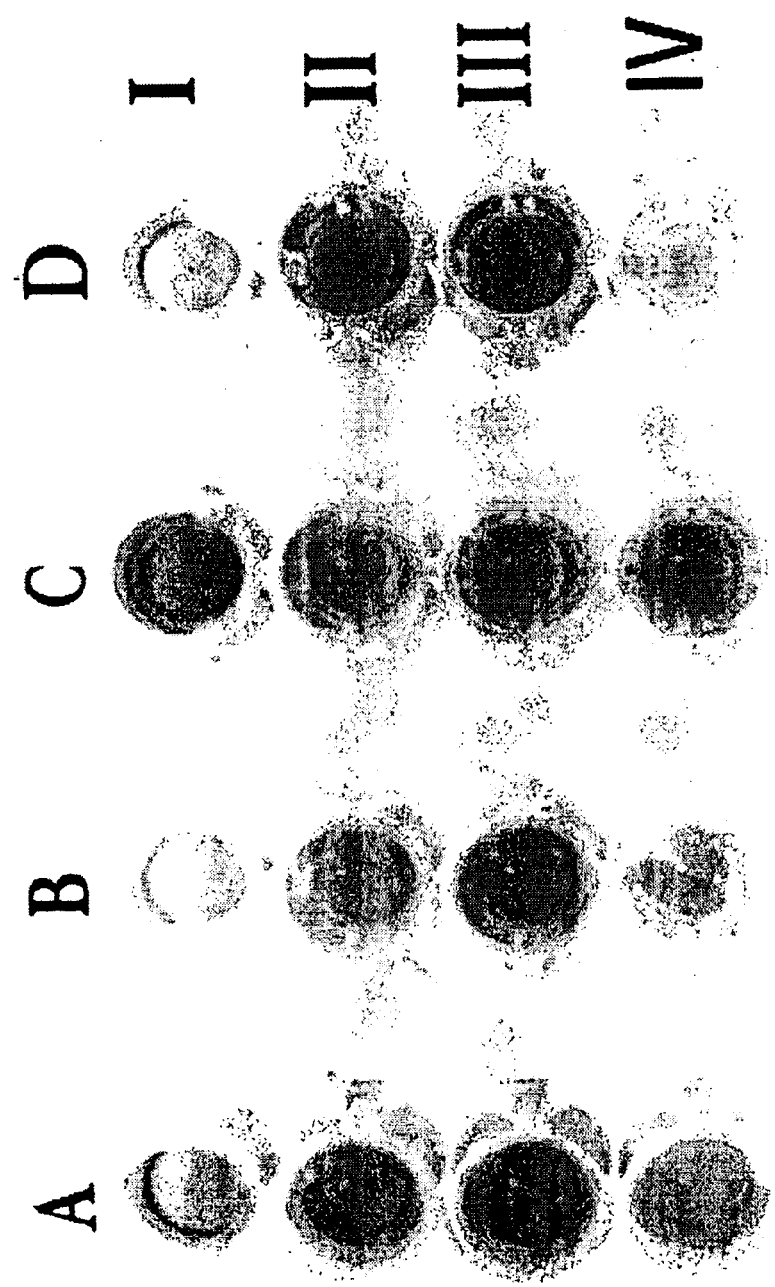
FIG. 24 is a photograph showing the color intensity of the soluble product, developed on the DNA samples loaded on the FTA-membrane by polyethyleneimide-peroxidase (PEI-PO) conjugate assay.

DNA-positive and DNA-negative samples developed different color intensities on the FTA-nylon, and FTA-nitrocellulose membranes, both having a pore size of 0.2 µm, when the result of the enzyme reaction was soluble products (table 6, FIG. 24).

Figure 25:
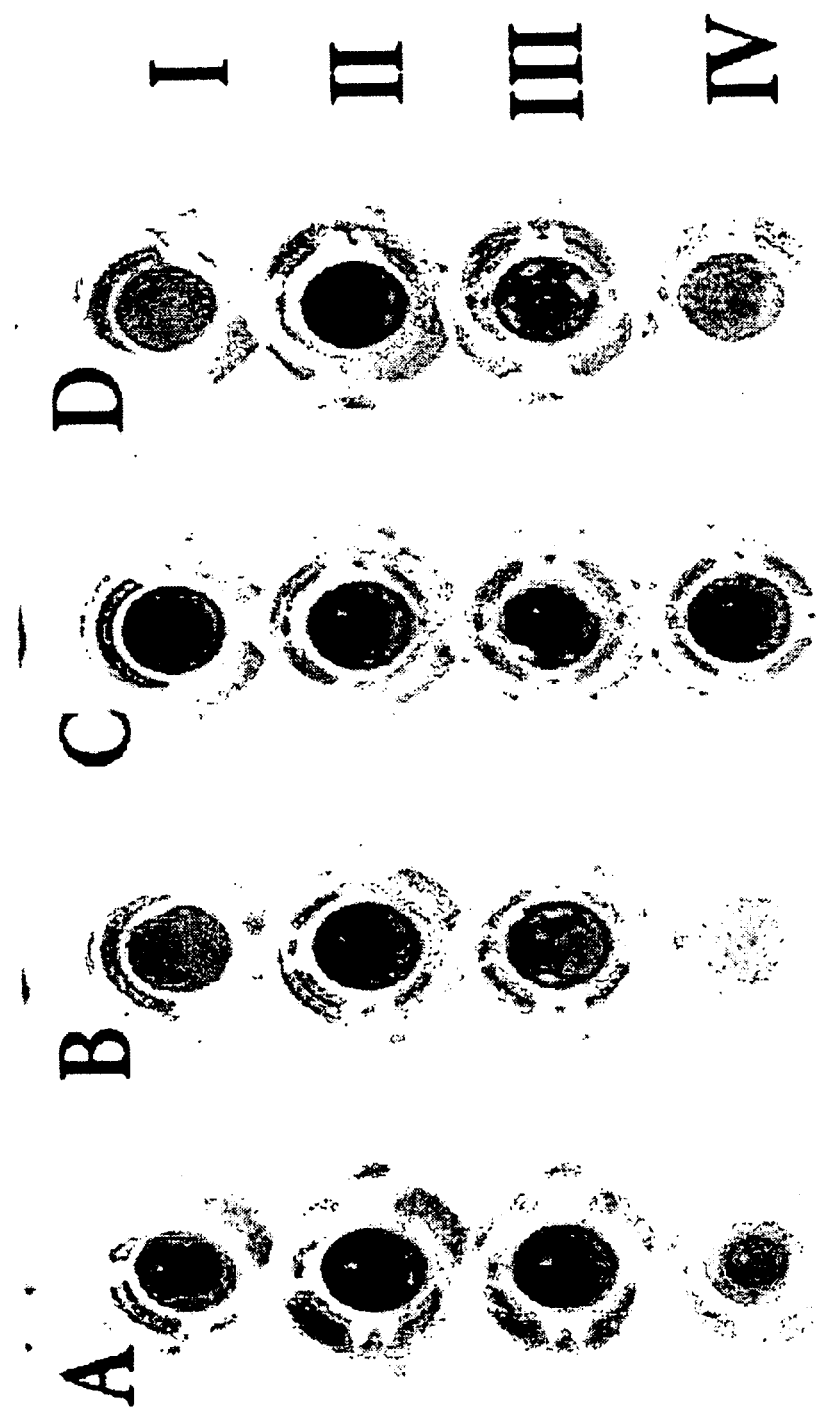
FIG. 25 is a photograph showing the color intensity of the insoluble product, developed ran the DNA samples loading on the FTA-membrane by polyethyleneimide-peroxidase conjugate assay.

DNA-positive and DNA-negative samples only developed different color intensity, on FTA nitocellulose membrane, with a pore size of 0.2 µm, when the result of the enzyme reaction was insoluble product (table 7, FIG. 25).

Advantages Or Unexpected Features

DNA can be loaded on the FTA or SDS treated membrane for later use in an ELISA determination. Additionally, DNA can be released from WBC on FTA treated membrane (0.2 µm pore size) for subsequent analytical determinations.

Physical and chemical properties of the FTA-treated membrane (such as pore size or membrane composition) are critical for their application for DNA evaluation. For example, FTA-nylon membrane, 0.2 µm pore size, showed the best results for measuring a differing amount of DNA and discriminating the DNA-positive and DNA-negative samples.

TABLE 6

Color Intensity Developed On The Samples Loaded On The FTA Materials By PEI-PO Assay With The Soluble Product Of PO, Reading at 490 nm

| | | A<br>5 × 10$^3$<br>WBC/µl | B<br>5 × 10<br>WBC/µl | C<br>2 µg/<br>µl DNA | D<br>0-<br>control |
|---|---|---|---|---|---|
| I | 0.2 µm nylon | 1.131 | 0.58 | over reading | 0.511 |
| II | 1.2 µm nylon | 2.279 | 1.445 | 1.92 | 2.408 |
| III | FTA-glass | over reading | over reading | over reading | over reading |
| IV | 0.2 µm nitrocellulose | 1.034 | 0.506 | 2.208 | 0.327 |

Over-reading occurs when an optical density of the sample is more than 3.000. A 3 µl sample was loaded into each well. Visual Estimation of the Color Development on the Samples Loaded on FTA-Materials by PEI-PO Assay with the Insoluble Product of PO 0.2 µm Nylon A dark brown ring developed in the middle of the membrane when treated with 5×10$^3$ WBC/µl. A light brown background with no ring developed when adding 5×10$^3$ WBC/µl. When 2 µg/µl DNA was added the 0.2 µm Nylon developed a dark brown background. Finally, a light brown background developed in the control situation.

1.2 µm Nylon

For all of the above concentrations, the background of all pieces is the same dark brown. There is no difference in the color of the DNA-positive membranes and the control one.

FTA-glass

As with the 1.2 µm nylon material, the background of all pieces is the same dark brown. There is no difference in the color of the DNA-positive membranes and the control one.

0.2 µm Nitrocellulose

With the addition of 5×10$^3$ WBC/µl a dark brown ring developed in the middle of the membrane with a very light background. A very light brown ring in the middle of the membrane developed when 5×10 WBC/µl was added. A dark brown background developed when 2 µl/µl DNA was added. A very light brown background developed in the control situation.

Example 14

FTA Cellulose Nitrate Membrane Application for DNA Determination

Membranes

Whatman Cellulose Nitrate Membranes having pore sizes of 0.1, 0.2, 0.45, and 0.8 µm were used for the following experiments. The membranes were soaked with the FTA solution for one hour at 80° C. with gentle agitation, dried completely at room temperature, and baked at 80° for one hour.

DNA Samples

Three DNA samples were used for the following experiments. These samples include the following: 1. Single-stranded DNA, 1 µg/µl; 2. Single-stranded DNA, 0.2 µg/µl; and 3. DNA-negative sample-PBS with 3% BSA solution.

Protocol

2 µl of the single stranded DNA solutions having a DNA concentration of 1 µg/µl and 0.2 µg/µl were fixed on the pieces of the membrane in a 96 well plate. The plate was blocked with PBS-BSA-Tween-20 buffer solution, incubated with a polyethyleneimine-peroxidase (PEI-PO) conjugate and washed three times before incubation with substrate solutions.

DNA attached to the FTA membrane; in one set or the wells, was visualized directly on the membrane when the insoluble product of PO was developed subsequent to incubation with 3,3'-dianisidine. A duplicate set of the wells was incubated with 1,2-ortophenylenediamine dihydrochloride (OPD) and color development in supernatant was estimated at 490 nm.

Results

The color intensity that was developed on the FTA membrane directly correlates with the amount of DNA loaded per well. The best resolution between DNA-positive samples with different DNA concentration and DNA-negative samples was achieved on the membrane with 0.8 µm pore size, the reading at 490 nm was: DNA-negative wells, 0.204; 0.2 µg DNA/well, 1.070; 1 µg DNA/well, 1.776.

When the insoluble PO product indicated the amount of DNA, the most distinct differences between DNA-positive samples with different DNA concentrations and DNA-negative samples was achieved on the membrane with 0.1 µm pore size.

Example 15

FTA Nylon and Nitrocellulose Membrane Application for WBC Determination

Membranes

Four membranes were used for the following experiment. These membranes are as follows: Nitrocellulose membrane, pore size 0.2 µm, Schleicher & Schull; Nylon membrane, pore size 0.2 µm, Osmonics; Nylon membrane, pore size 1.2 µm, Osmonics; and FTA-glass, grade F572-08, Whatman (used for comparison).

The Membranes were soaked with the FTA solution for two hours at room temperature with gentle agitation, dried completely at room temperature, and baked at 80° C. for one hour.

WBC Samples

Samples or various concentrations were used in the experiment. These concentrations include: WBC, 5×10$^3$ cell/µl; WBC, 5 cell/µl; DNA-positive control, 2 µg/µl single stranded DNA in water; and WBC-negative control, 3% BSA in PBS.

Protocol

All assay steps were performed in one 96 well plate. The circles of each membrane, 0.5 mm in diameter, were put on the bottom of each well. WBC samples of 3 µl were loaded in each well, in duplicate. Then the plate was subsequently blocked with PBS/BSA/Tween-20 solution, incubated with polyethyleneimine-peroxidase conjugate, washed with PBS/BSA/Tween-20 solution, and finally incubated with different substrates for peroxidase to develop colored soluble or insoluble products.

Results

Figure 31:
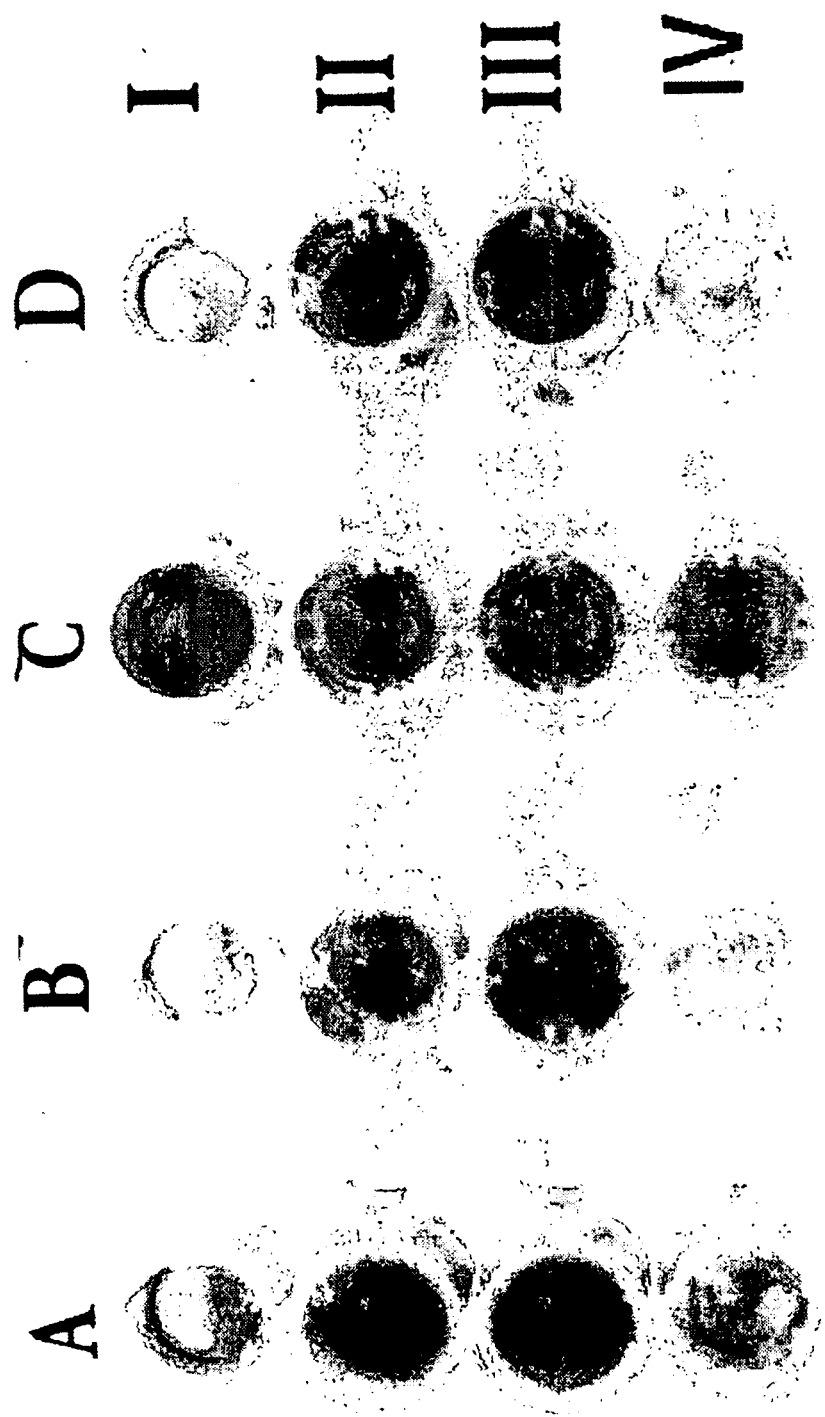
FIG. 31 depicts WBC counting on nylon and nitrocellulose membranes when the result of the enzyme reactions was soluble product/substrate.

WBC positive and WBC-negative samples developed different color intensities on the FTA-nylon, and FTA-nitrocellulose membranes, each having a pore size of 0.2 µm. The color intensity developed when the result of the enzyme reaction was soluble product/substrate (FIG. 31).

Figure 32:
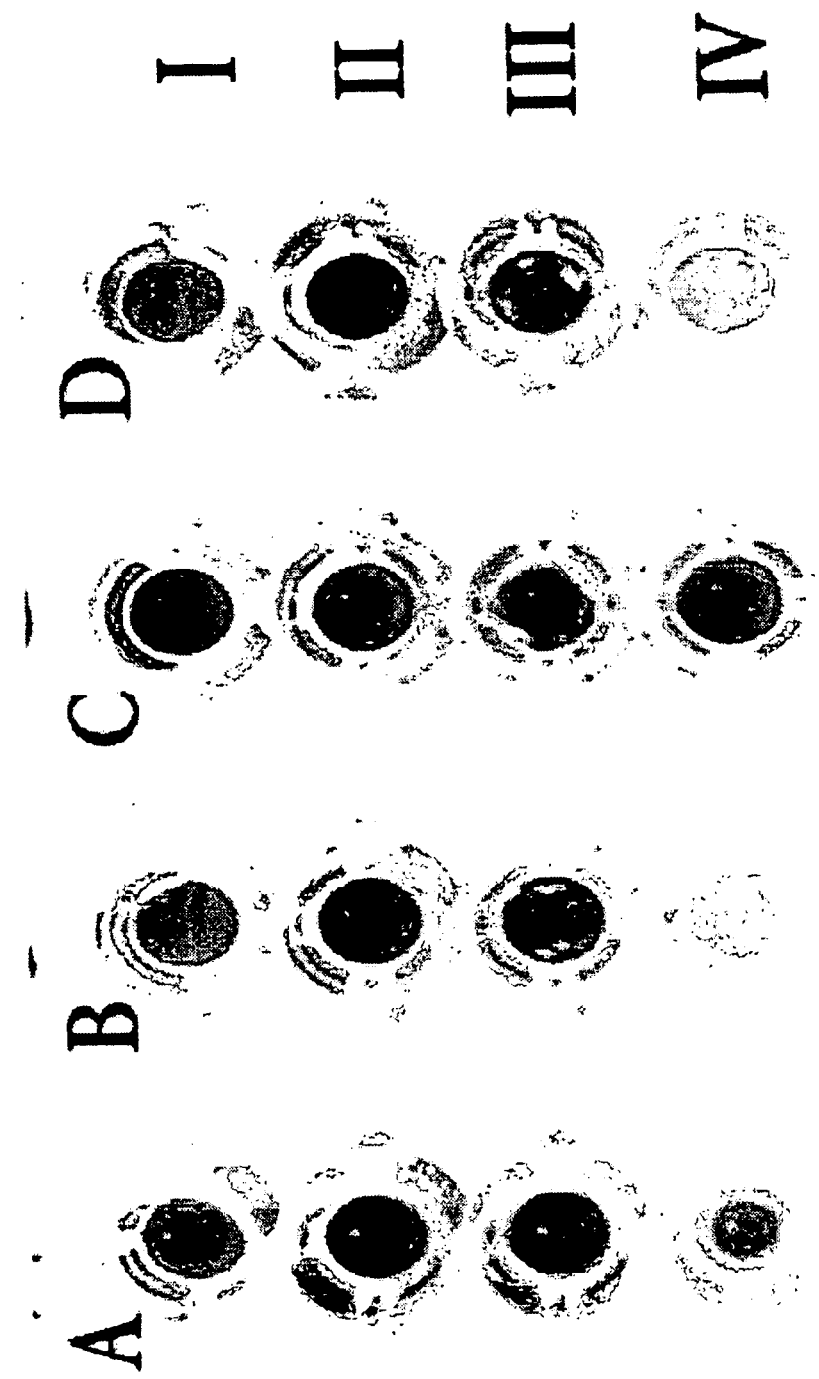
FIG. 32 depicts WBC counting on nylon and nitrocellulose membranes when the result of the enzyme reactions was insoluble product/substrate.

DNA positive and DNA-negative samples developed different color intensity on the FTA-nitrocellulose membrane, having a pore size of 0.2 µm. Again, the color intensity developed when the result of the enzyme reaction was insoluble product/substrate (FIG. 32).

Conclusions

The color intensity developed on the FTA membranes in 96 well plate as a result of the PEI-PO assay. This directly correlates with the amount of WBC. The DNA can be released from WBC on FTA-treated membranes for subsequent analytical determination.

Physical and chemical properties of the FTA-treated membrane such as pore size are important for DNA evaluation. On the basis of two experiments it has been shown that the membrane with a 0.8 µm pore size is the best for DNA determination, while 0.1 µm pore size membrane is more promising for WBC evaluation.

Results Presented in Tables 7 and 8 and FIGS. 32 and 33, Marked as Following (3 µl of the Sample was Loaded in the Well)

TABLE 7

Color intensity developed on the samples loaded on the FTA materials by PEI-PO assay with the soluble substrate for PO, reading at 490 nm.

| Rows: | Concentration: | A<br>$5 \times 10^3$<br>WBC/µl | B<br>5<br>WBC/µl | C<br>2 µg/µg<br>DNA | D<br>0-<br>control |
|---|---|---|---|---|---|
| I | 0.2 µm nylon | 1.131 | 0.58 | over reading | 0.511 |
| II | 1.2 µm nylon | 2.279 | 1.445 | 1.92 | 2.408 |
| III | FTA-glass | over reading | over reading | over reading | over reading |
| IV | 0.2 µm nitrocellulose | 1.034 | 0.506 | 2.208 | 0.327 |

TABLE 8

Visual estimation of the color development on the samples loaded on FTA-materials by PEI-PO assay with the insoluble substrate for PO (DB dark brown; LB = light brown; VLB = very light brown; ring = ring in the middle).

| Rows: | Concentration: | A<br>$5 \times 10^3$<br>WBC/µl | B<br>5<br>WBC/µl | C<br>2 µg/µg<br>DNA | D<br>0-<br>control |
|---|---|---|---|---|---|
| I | 0.2 µm nylon | DB ring | LB | DB | LB |
| II | 1.2 µm nylon | DB | DB | DB | DB |
| III | FTA-glass | DB | DB | DB | DB |
| IV | 0.2 µm nitrocellulose | DB ring | VLB ring | DB | VLB |

Advantages include alleviating the bottleneck of nucleic acid preparation. Also, GC adapters on gene specific primers enable immobilization so the solid phase (See Yang et al. (1998) PNAS. Vol.95, pp.5462–5467). Additionally, DNA, can be loaded on the FTA treated membrane for following ELISA determination and DNA can be released from WBC on FTA treated membrane (0.2 µm pore size) for following analytical determination.

Example 16

Detection Limits of FTA Cellulose Nitrate Membranes

The detection limit of the PEI-PO assay on FTA cellulose nitrate membrane for single- and double-stranded DNA was analyzed.

Objectives

Whatman Cellulose Nitrate membrane, pore size 0.8 µm was treated with FTA solution. Seven different variables were studied to find out the sensitive points of each step of the PEI-PO assay for DNA determination in 96 well plate and used to determine the detection limit of the method for purified DNA. DNA samples as single- and double-stranded DNA solutions were fixed on the FTA treated membranes in a 96 well plate, 40 pg–400 ng DNA/well. All steps and ingredients of the assay, plate pretreatment, baking step after loading DNA, blocking buffer, can contribute to the assay sensitivity. Preliminary results suggested that detection limit of this method on cellulose nitrate membrane pore size 0.8 is 40 pg/well for single-stranded DNA and 400 pg for double-stranded DNA.

Materials
Membranes

Cellulose Nitrate Membranes were obtained from the Arbor Technologies samples library. Membranes having a pore size of 0.8 µm were utilized for the following experiments. The membranes were soaked with the FTA for one hour at 80° C., dried completely at room temperature, and baked at 80° C. for one hour.

DNA Samples

Single-stranded human genomic DNA having the following concentrations were used: 20 ng/µl, 2 ng/µl, 200 pg/µl, 20 pg/µl. DEPC water was used as DNA-negative control. 2 µl of each DNA concentration sample was loaded onto the pieces of FTA cellulose nitrate membrane. The specimens were loaded in duplicate or triplicate.

Block solutions of PBS, 3% BSA, 0.1% Tween-20 (block solution #1), PBS, 3% BSA (block solution #2), and 10×Denhardt's solution (1% Ficoll 400, 1% polyvinylpyrolidone, 1% BSA), 4×SET (NaCl, EDTA, Tris-HCl, pH 8.0), 0.1% SDS (block solution #3) were used when conducting these experiments.

All of these variables were chosen to find out the sensitive points of each step of the PEI-PO assay for DNA determination in 96 well plate.

Two experiments were performed with FTA cellulose nitrate membrane for DNA determination. The goal of the first experiment was to find the detection limit of the method for double and single stranded DNA using following protocol. First, 2 µl of the different DNA solutions were fixed on the pieces of the membrane in 96 well plate in duplicate. The plate was baked for one hour at 80° C. Then, the plate was blocked with block solution 1 for one hour at 37° C. The plate was incubated with PEI-PO conjugate for one hour at 37° C., then washed three times with PBS, 0.1% Tween, for 10 minutes at 37° C. The DNA in one set or the wells was visualized directly on the membrane when insoluble product or PO was developed after incubation with 3,3'-dianisidine. A duplicate set of the wells was incubated with 1,2-ortophenylenediamine dihydrochloride (OPD) and color development in supernatant was estimated at 490 nm.

The goal of the second experiment was to repeat the determination of the detection limit and compare the results after incubating plates with different block solutions. In this experiment, untreated plates and plates treated with 0.1% Tween-20 were used. The membrane in each kind of plate, after DNA loading was either baked or not baked.

Results

The combination of washing the plate with Tween-20 and using block solution #1 gave the best result with a low nonspecific background. The background measurement at 490 nm was as low as 0.200 on DNA negative membranes. Block solutions #2 and #3 increased nonspecific sorption of PEI-PO. The background measurement at 490 nm was 0.6–0.8. The detection limit of the method was found 40 pg/well for single-stranded DNA and 400 pg/well for double-stranded DNA. Baking step was find necessary for pure DNA determination by PEI-PO assay on the cellulose nitrate membrane.

Conclusions

The plate should be pretreated with 0.1% Tween-20 solution before DNA determination on the FTA membrane to create low nonspecific background. Among the three buffers only block solution #1 (PBS, 3% BSA, 0.1% Tween-20) works as a block solution for PEI-PO nonspecific sorption on the FTA-membrane.

Results suggested that the detection limit of this method on cellulose nitrate membrane having a pore size of 0.8 is 40 pg/well for single-stranded DNA and 400 pg for double-stranded DNA.

Example 17

Quantitative DNA Measurements on FTA Membranes

Two ELISA modifications were used to confirm that DNA can be released from white blood calls (WBC) on an FTA treated cellulose nitrate membrane for subsequent quantitative determination.

Whatman Cellulose Nitrate and Nylon membranes, having a pore size of 0.2 µm, were treated with FTA solution. Two version of FTA treatment were used. First, membranes were treated with FTA in 96 well plate, and used for DNA determination in the same date. Second, membranes were treated with FTA solution, dried, cut into the pieces, loaded into the plate and then used for DNA determination.

Two ELISA modifications were used to confirm that DNA can be released from white blood cells (WBC) on FTA treated cellulose nitrate membrane for subsequent analytical determination.

Materials
Membranes

Whatman Cellulose Nitrate membranes, pore size 0.2, 0.8 µm and Whatman Nylon membranes, standard and SP, both with pore size of 0.2 µm were utilized.

FTA Treatment

Two treatments were applied: First—the pieces of the membranes, 5×10 cm, were soaked with the FTA solution (without uric acid) for 15 minutes, then baked at 80° C. for one hour. Second—membranes were stored between plain paper in plastic bags. Membranes were cut into circles of 0.5 mm diameter, and loaded into the 96 well plates. 10 µl of FTA solution was applied to each well on top of the membrane. The plate was completely dried at 80° C.

DNA Samples

Single-stranded human genomic DNA, of the following concentrations were used: 2 ng/µl, 200 pg/µl, 20 pg/µl; as well as DEPC water which was used as a DNA-negative control.

WBC Samples

WBC were isolated from fresh human blood after lysis of the red cells with ammonium chloride buffer and three washing steps with PBS, 1.5% BSA, WBC suspension was diluted to cell concentrations of $8\times10^3$, $4\times10^2$ and 2 cells per µl. 2 µl of each WBC concentration samples were loaded on the pieces of FTA membranes in duplicate or triplicate.

Study Design and Method

The goal or the experiments was to find the optimal FTA treatment of the membranes for DNA determination in a 96 well plate. The goal of the second experiment was to compare two different ELISA assays for WBC determination on the cellulose nitrate and nylon membranes.

ELISA was conducted on the basis of antibodies to human DNA and was designed after the optimization of all of the following steps: The experiment began with the loading of WBC and DNA samples ors the pieces of FTA membranes in a 96 well plate. Then the plate was baked for one hour at 80° C. Incubation occurred next with block solution, PBS, 3% BSA, 0.1% Tween-20. Then there was incubation with human monoclonal antibodies (Abs) specific to human DNA, including 1 µg of Abs/ml for one hour at 37° C. or overnight in refrigerator. Subsequently, washing occurred three times for five minutes at room temperature. Incubation with mouse antibodies specific to human IgG conjugated with biotin, at a dilution of 1:15,000 occurred for one hour at 37° C. Then it was washed three times for five minutes at room temperature. Next, incubation with avidin-poly-HRP, at a dilution 1:5,000 occurred for 45 minutes at 37° C. Then it was washed three times for five minutes at room temperature. The OPD substrate was incubated for 20 minutes at 37° C. Incubation was stopped with 3M sulfuric acid. The supernatant was transferred from the wells to the replica plates. Then the reading plate was analyzed at 490 nm.

Results

A very high positive background developed on all membranes treated with ETA in the plate. No statistical differences were observed between DNA-positive and DNA-negative wells with membranes, which were treated with FTA in the plate. When the membranes were treated with FTA before loading in the plate, very bright dark brown rings were formed on the cellulose nitrate membranes loaded with WBC, $8\times10^3$ cell per µl during PEI-PO assay. The same bright rings for this WBC concentration, as well as for the concentration of $40\times10^2$ cell/µl, were observed on the cellulose nitrate membrane with an assay based on antibodies to human DNA. No rings were seen on the membranes loaded with pure DNA, or 20 WBC for µl samples.

The color intensity measured in the plates after PEI-PO and antibodies to human DNA assays at 490 nm presented in the following table.

TABLE 9

Color Intensity Developed on the WBC Samples Loaded on the FTA-Cellulose Nitrate Membrane ELISA Assays, Reading at 490 nm

|  | PEI-PO Assay | | Abs to human DNA | |
| --- | --- | --- | --- | --- |
|  | Mean | SD | Mean | SD |
| $8 \times 10^3$ cell/µl | 1.491 | 0.152 | 2.013 | 0.771 |
| $4 \times 10^2$ cell/µl | 1.255 | 0.214 | 0.645 | 0.104 |
| 20 cell/µl | 1.079 | 0.204 | 0.303 | 0.041 |
| DNA-positive control | 1.120 | 0.290 | 0.405 | 0.026 |
| DNA-negative control | 0.830 | 0.117 | 0.324 | 0.042 |

The color intensity developed on WBC positive membranes directly depends on WBC concentration. Nonspecific background was lower after an assay based on antibodies to human DNA. Both assays gave similar intensity between DNA positive and DNA negative samples, 0.74 for PEI-PO assay and 0.8 for antibodies to human DNA assay. But in the case of using specific antibodies, a more pronounced difference was observed between samples with different WBC concentration.

Conclusions

DNA can be released from WBC on FTA treated cellulose nitrate membranes for subsequent determination. Color intensity developed on the WBC positive membranes depends on cell concentration.

Immunoassays based on the interaction between DNA and polyethyleneimine (nonspecific) or DNA and monoclonal antibodies to DNA (specific) can be applied to DNA determination on FTA cellulose nitrate membranes in a 96 well plate. Treatment of the membrane with FTA directly in the wells of the plate results in a very high non-specific sorption of PEI to the membrane.

Nylon membranes, both standard and SP, having pore sizes of 0.2, have a very high nonspecific background after incubation with PEI-PO and antibodies to human DNA assays. In the present setting, these membranes could not be recommended for DNA determination with ELISA assays.

Example 18

The following experiment demonstrates that DNA or genetic material isolated from low amounts of white blood cells, such as 33 cells per well or 0.33 cell/µl can be measured.

White blood cell concentration of 1 cell per ml represents the amount of cells allowed for a whole blood unit, having a volume of 500 ml, to be marked as leukoreduction (LR) according to the European Standard. This method is able to detect such low levels of concentrations that is can be recommended for QC of leukoreduced blood.

Materials and Protocol

White blood cell suspensions were obtained from whole blood samples after lysing red blood cells with ammonium chloride buffer. The concentration of white blood cells can be in the range of 1 to 1000 cells per µl. In this experiment, 100 ml of white blood cells from leukoreduced blood was loaded on FTA membrane and resulted in the collection of 600 pg DNA per well (note that there is 7 pg of DNA in a single human cell). Fluorescent stain of cell nucleus with Propidium Iodine detergent solution and fluorescent microscopy was used for validation of white blood cell lysis on the FTA membrane.

A 96 well plate with control nitrocellulose membrane and the FTA membrane were loaded with white blood cells. Two methods were used. At first, the white blood cell suspension was spotted on the membrane in a volume of 2.5 µl/well. According to a second protocol, different volumes of white blood cells in the range of 20–180 µl/well were applied to the membrane by vacuum filtration. Two different ELISA systems were used to measure DNA in each well. The first ELISA was based on polyethyleneimine-peroxidase conjugate. The second protocol used monoclonal antibodies specific to human genomic DNA.

The detection limit was achieved by conducting an experiment when the same plate was loaded with genomic DNA samples in concentration range of 0.2–20 ng per well and white blood cell samples in amount of 90–360 per well. DNA samples were spotted on the membrane in volume of 2 ml per well. White blood cell samples were loaded in volumes of 30–120 µl per well by vacuum filtration.

Results

The white blood cells stained with Propidium Iodine and spotted on nitrocellulose membrane can be observed with a fluorescent microscope which are seen as bright pink spots spread over the membrane surface. The amount of cells counted on the membrane depends on the amount of white blood cells loaded. Propidium Iodine staining indicated that no intact cells remained on the FTA membrane spotted with the same amount of white blood cells. The color intensity of the ELISA product developed on the FTA membrane has a linear correlation with the amount of white blood cells loaded per well. The detection limit for white blood cell was determined to be 100 cells per well. This represents the concentration of 1 cell/µl. The volume capacity was found as 100 µl of white blood cells suspension per well. When 3'3-diaminobenzidine was used as substrate for peroxidase, an insoluble product formed in the white blood cell positive wells as brown rings on the FTA membrane. The thickness and intensity of the rings depends on the amount of cells in the well.

The volume capacity for 0.8–1.2 FTA-NC membrane was shown to be ~100 µl of white blood cell suspension per well. So, it is possible to obtain 600 pg of DNA per well. This amount can be detected on FTA-NC membranes with ELISA using antibodies specific to human DNA above the background.

The sensitivity of the method, which causes the FTA membrane to lyse cells and capture of cell DNA and ELISA detection system on the basis of antibodies specific to human DNA is 0.2 ng of DNA per well in a 96 well plate format. In the initial experiments the sensitivity of the method was found as ~100 µl per well of white blood cell suspension with cell concentration of 3 cell per µl (as average count), or 5+/−4 cells/µl. Accuracy at this level is in the range of 5+/−4 cells per µl. However, in an additional experiment, using the same method, the sensitivity was determined to be 33 cells per well.

Figure 26:
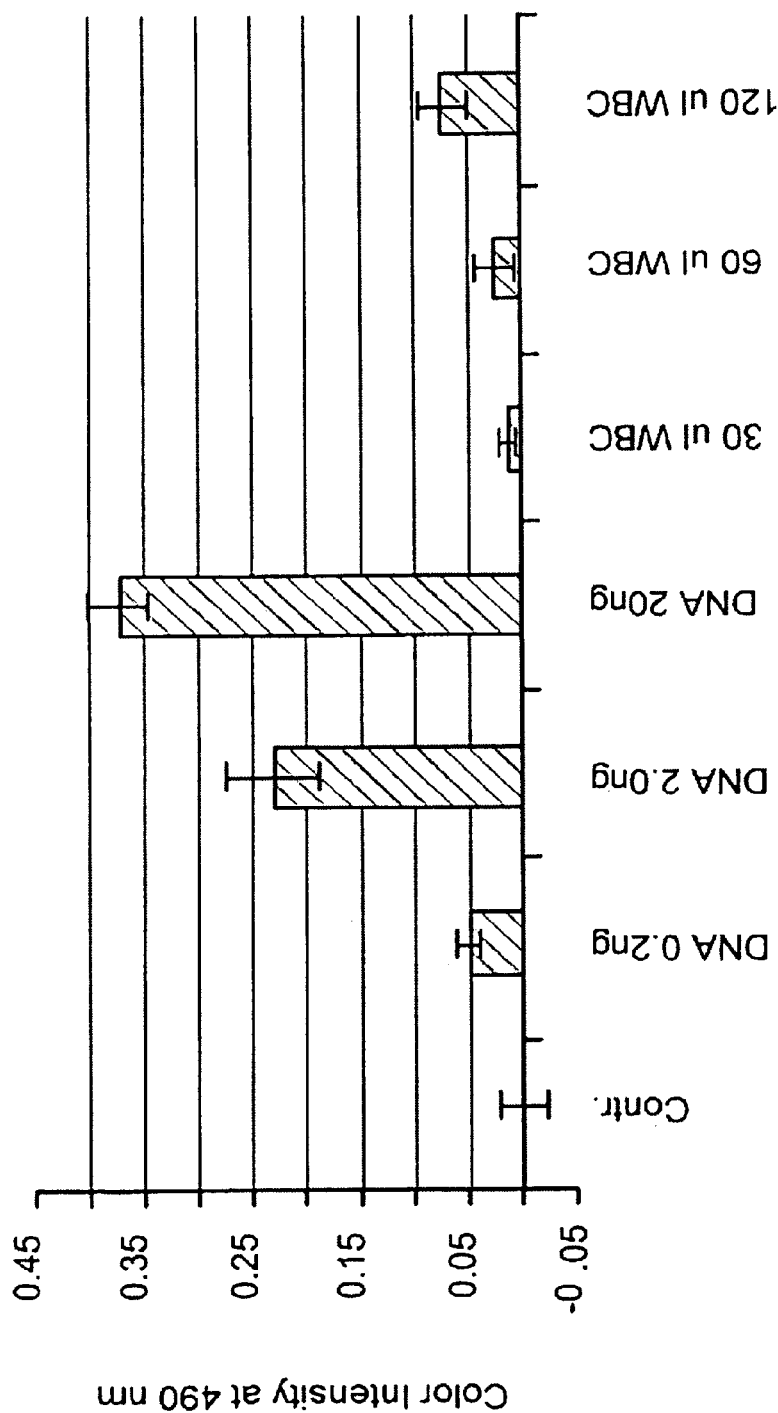
FIG. 26 is a graph showing the detection of DNA and white blood cells on FTA-NC membranes having a 1.2 μm pore size using ELISA on basis antibodies to human DNA.
Figure 27:
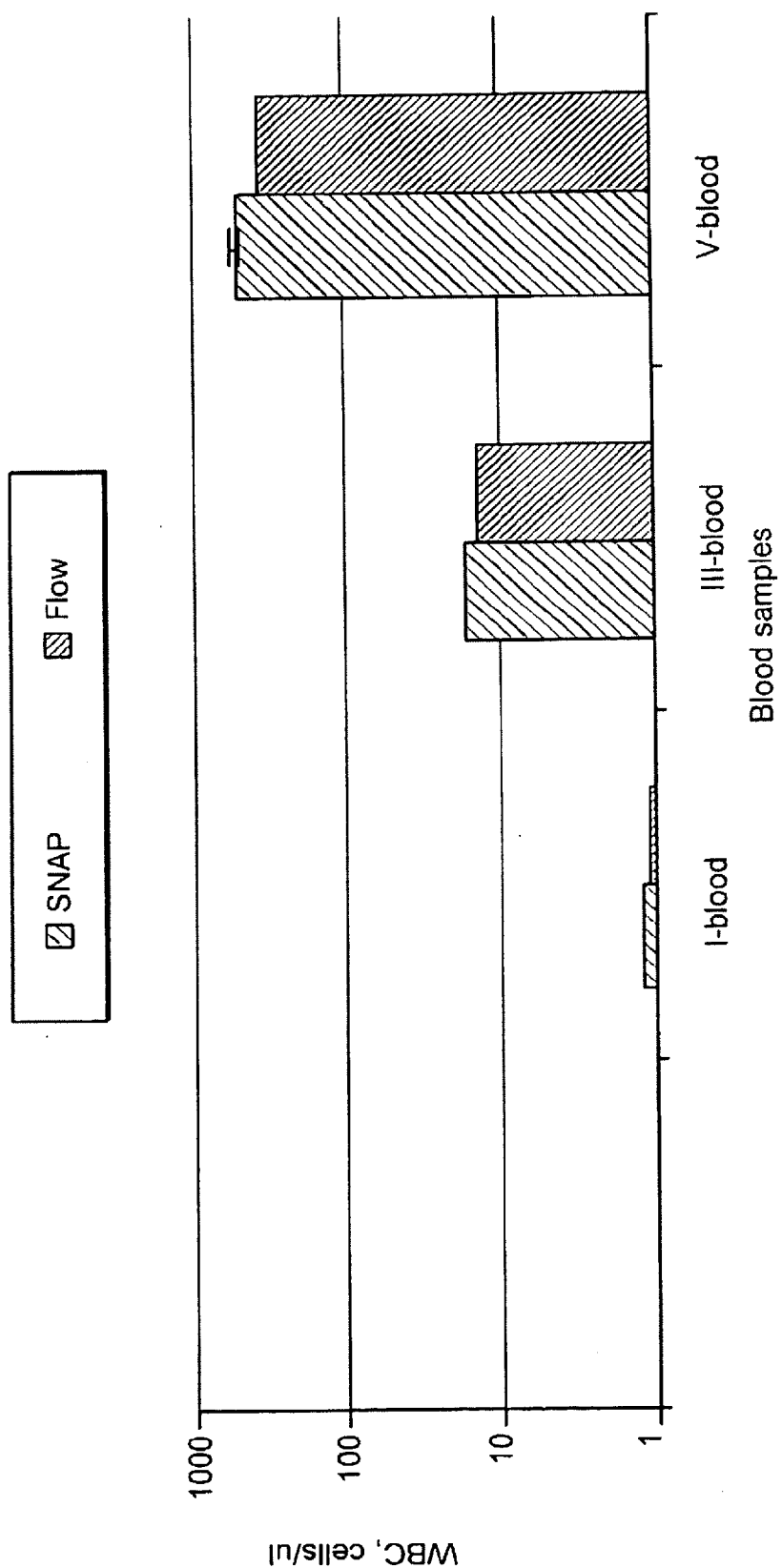
FIG. 27 depicts a comparison of results using WBPS DNA extraction method and flow cytometry for leukocyte enumeration in LR frozen CPDA whole blood samples.

With ELISA, on the basis of antibodies specific to human DNA, it was possible to see a difference between control wells loaded with PBS and DNA and white blood cell positive wells loaded with 0.2 ng DNA/well or 60 µl white blood cells/well. There is a linear dependency between color intensity of the assay and the amount of DNA. Additionally, there is a linear dependency between the assay and the white blood cells loaded per well. The data is presented in FIG. 26.

Example 19

Measurement of Level of Antibodies to Human DNA on FTA Membranes

FTA nitrocellulose membrane application for measurement of the level of antibodies to human DNA. Lupus disease diagnostics.

Study Design

Double stranded genomic DNA or suspension of WBC as sources of human DNA was loaded on the pieces of FTA-nitrocellulose membrane in 96 well plate. Plate was incubated with antibodies (Abs) specific to human DNA, which were obtained from the patient with Lupus disease. Concentration of Abs was 1 μg of Abs/ml. ELISA assay on the basis of mouse anti-human Abs conjugated with biotin and poly-avidin-HRP were performed on the plate. The color intensity developed the in the Abs to human DNA positive wells and controls wells measured at 490 nm.

Results

TABLE 10

Color Intensity Developed on the FTA-Cellulose Nitrate Membrane in Abs to Human DNA Positive Wells by ELISA Assays, Reading at 490 nm

|  | Abs to Human DNA | Control |
| --- | --- | --- |
| WBS as DNA source | 2.013 +/− 0.777 | 0.324 +/− 0.042 |
| Genomic DNA as DNA source | 0.405 +/− 0.026 | 0.324 +/− 0.042 |

Conclusion

FTA-treated membrane can be used to load DNA for following determination of antibodies specific to human DNA in the plasma of patients with Lupus disease.

FTA coated filter materials are known to the art as tools for the analysis of genetic materials (Finder Patents) particularly for genomic DNA form any number of sources. Nucleic acid from blood samples can be purified, retained, and readily utilized for PCR on FTA coated materials such as celluloid 3IET or glass microfiber. The genetic material bound to FTA filers can be stored in a useable state at room temperature for a great deal of time (up to 10 years to date).

There are many ways that FTA coated materials can be utilized to address the concerns listed previously. Such utilization would include:

1. FTA Tags Attached to Donated Blood Bags

A blood spot from the donor administered to an FTA card attached to a blood bag into which the donor is contributing would solve problems such as traceability, archiving and safety (pathogens are completely inactivated on FTA) of handling. One would not need to draw blood from the bag for NAT, thereby negating the need to elaborate QC measures to prevent cross-contamination of neighboring blood samples.

2. FTA Provides a Rapid Method for Nucleic Acid Purification

Currently in the blood transfusion community, nucleic acid from donated samples is prepared by traditional techniques which take up to 90+minutes. Preparation of usable nucleic acid when using FTA material takes ten minutes. Materials such as a 96 well microplate or tube containing FTA filters could be utilized by blood services for rapid preparation. There is also provision to include the technique of eluting nucleic acid from the FTA filter if a soluble fraction maybe more useful for some of the pathogen detection systems such as transcription mediated amplification (TMA).

3. 96 Pooled Samples

A 96 well microplate containing FTA filter material could be used to provide longer pool analysis than that which is currently undertaken (24 is normal). The advantage of a 96 well FTA tool is that all samples are processed as one, but yield singular results, completely negating the need for iterative analysis if the traditional pool is found as pathogen-positive. There would also be a reduced risk for "false-positive" results that occur by inadvertently following the wrong iterative pathway.

4. Blood Archive Cards

An extension of the blood bag tag idea where a portion of the original tag is archived for "look back" purposes as new pathogens are discovered and become of interest. FTA solid phase storage of nucleic acid has been shown to yield usable product after ten years of RT storage. Storage/archive could be carried out in a file cabinet instead of frozen aliquots.

5. NAT Prior to Blood Donation

Administer a drop of blood (donor) to a card provided (or brought in by donor). Test by NAT, and if clear, draw donated blood after this testing. The advantage being that only safe blood enters the community.

6. Multiple Pathogen Testing

Donor blood administered to an FTA device can be tested for many pathogens at once by PCR techniques. A 50 μl blood spot yields a large surface on a filter from which may one millimeter punches can be taken. Also, the provision exists to carry out different, specific PCR reactions on the same punch.

7. Transport of Blood Sample

Donations taken at institutions do not necessarily carry out NAT. Expensive measures are taken to draw blood into tubes and then ship them to NAT testing centers. An FTA device with a donor blood spot can be sent via US postal service at room temperature with no additional expense.

8. Ambulance FTA Cards

Accident victims, etc. can be NAT tested very rapidly if victim blood is archived to an FTA card that is carried by the ambulance crew.

Example 20

Testing of a Blood Sample without Elution

A unit of blood is drawn for transfusion at a blood center and is prepared for leukodepletion with a conventionally available filter. Attached to the filter and bag set is a sample spin tube and spin basket set which includes three tube sets, 12 ml of FTA buffer, 6 ml of TE buffer, and 3 ml of DNAse free water. After leukodepletion, 26 microliters of the leukodepleted blood is spotted onto each of the filters in the spin baskets. After two minutes, two samples are allowed to dry and serve as retention samples with barcodes connecting them to the original unit of blood, and hence the donor and drawing center. The third sample is dried, washed twice with FTA buffer and twice with TE buffer via addition and centrifugation, 50 microliters of DNAse free water is added, the unit heated for 10 minutes in boiling water and centrifuged to recover the DNA. A suitable fluorescent reader to measure the residual DNA. A standard curve can then be used to indicate the exact level of leukocytes remaining after leukodepletion or a reading of "non-detected at . . . " can be entered if the level is lower than the limit of detection.

Example 21

Whatman BioSciences Purification System (WBPS) DNA Extraction Method for Residual Leukocyte Counting in Leukoreduced Whole Blood Objectives: The white blood cell (WBC) concentration in serial diluted whole blood samples was evaluated with Whatman BioSciences Purification System (WBPS—Whatman, Inc.) and PicoGreen fluorescent dye (PicoGreen Quantitation Reagent—Molecular Probes, Inc.).

The goal of the study was to approve the WBPS technology for WBC counting in LR blood.

Study Design: Samples of CPDA whole blood with expected WBC concentrations of 0, 1, 20, and 500 cells/μl were prepared by serial dilutions of whole fresh blood with "WBC-free" diluent. Diluent was prepared by double filtration of the blood unit using a leukoreduction filter. Samples were frozen at −70° C. Leukocyte concentration was evaluated in thawed samples after three days of storage with both WBPS DNA extraction method using PicoGreen dye and Flow cytometry using a Leuco-COUNT™ kit (Becton Dickinson).

Solutions: Solutions were prepared as follows:
Solution 1:
    Ammonium chloride 0.83%
    Ammonium carbonate 0.16%
    EDTA 0.1 mM
Solution 2:
    0.5% SDS
Solution 3:
    Per 1 liter
    Measure 500 ml purified water
    Add 10.0 ml (9.9–1.1 ml) 1M Tris (Whatman WB420003)
    Add 0.596 g (0.595–0.597 g) KCl (Whatman WB410015)
    Add 0.29 g (0.28–0.30 g) $MgCl_2$ (Whatman WB410014)
    Mix to dissolve
    Add 10.0 ml NFB (alternatively, fetal calf serum may be
used) and mix
    Add 0.5 g (0.49–0.51 g) NaMetabisulfite (Whatman WB410055) and
    mix
    Add water to 1000 ml and mix well.
    Aseptically filter solution through an 0.2 μm filter in a Class
    II safety
    cabinet
    Store at room temperature
Solution 4: TE (10 mM Tris; 1 mM EDTA) (alternatively, substitute water)

The WBPS protocol for DNA extraction from LR blood samples was as follows:

PROTOCOL:
    Load blood into WBPS columns (800 μl per single column);
    Apply low vacuum so blood will be drawn through the filter matrix with flow rate of ~0.5–1 ml/min;
    Add 1 ml of sol. 1, apply vacuum;
    Repeat the previous step 1 time
    Add 1 ml of sol. 2, apply low vacuum, release vacuum when approximately half of the sol. 2 volume is drawn through the filter;
    Incubate the columns with sol. 2 for 2 min, apply vacuum;
    Add 1 ml of sol. 2, apply vacuum;
    Add 1 ml of sol. 3, apply low vacuum;
    Add 0.5 ml of sol. 3, apply vacuum;
    Remove the columns from the Vacuum Manifold lid, wipe columns' nozzles with tissue to remove any contamination from previous steps; place a black cap onto each column nozzle;
    Add 100 μl of sol. 4 (or water), place the columns into the Heating Station (heat block);
    Incubate at 80° C. for 5 min;
    Replace the Waste Tray in the Vacuum Manifold with the Sample Collection Rack. Mark the collection tubes correspondingly to the marks on the columns.
    Remove the columns from the Heating Station and remove the black caps while the columns are still hot; put the columns into the Sample Collection Rack, and add 100 μl of sol. 4 (or water) to each column;
    Apply vacuum to collect DNA solutions into the collection tubes;
    Remove the columns from the Vacuum Manifold lid, place the black cap back onto each column nozzle;
    Add 120 μl of sol. 4 (or water), place the column into the Heating Station;
    Incubate at 80° C. for 5 min;
    Remove the columns from the Heating Station, remove the black caps, put the columns into the Sample Collection Rack correspondingly to their collection tubes;
    Apply vacuum to add this portion of DNA solutions to the collection tubes;
    DNA solution is now ready for quantitative evaluation The process of DNA isolation takes approximately 60 minutes.

Measure DNA concentration with Pico-green dye applying calibration curve of DNA standard solutions (takes approximately 30 minutes).*
    Leukocyte concentration is calculated taking into account the amount of DNA equal to 0.007 ng per 1 white cell in human blood.

*—Alternatively, the PicoGreen detection system may be replaced with the ACES kit (Whatman) if it is modified for quantitative DNA measurement.

Result

Figure 28:
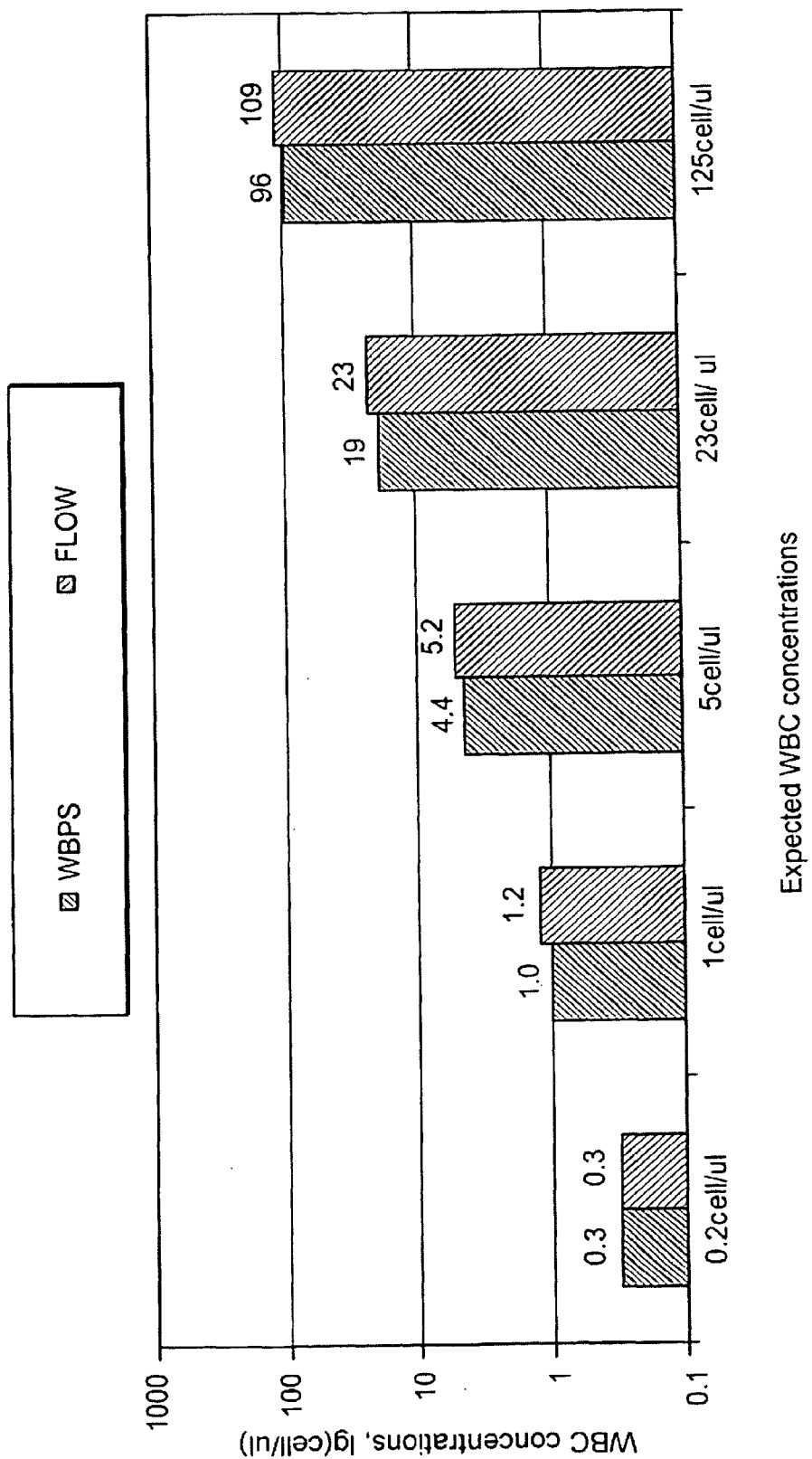
FIG. 28 depicts WBC counting in fresh red blood cell (RBC) samples with WBPS and flow cytometry.

Result of WBC concentration observed in the frozen samples of LR whole CPDA blood with WBPS DNA extraction method and flow cytometry presented on FIG. 28.

Conclusion: The WBC concentrations observed in frozen samples of LR whole blood with WBPS method were found in good agreement with the WBC concentrations observed with traditional flow cytometry method.

Example 22

WBPS for Residual Leukocyte Counting in Leukoreduced Whole Blood

Comparable Evaluation of the Method in Three-site Study

Objectives: The white blood cell (WBC) concentration in serial diluted blood samples was evaluated at three sites using three methods:
1. Whatman Bioscience, Newton, Mass., WBPS kit and Pico-green fluorescent dye.
2. Hemasure Inc., Marlborough, Mass., flow cytometry using a LeucoCOUNT™ kit and FACS Calibur (Becton Dickinson).
3. The Blood Centers of the Pacific, quantitative PCR of an HLA-DQ-A sequence using real-time GeneAmp 5700 (Applied Biosystems).

All sites used aliquots of the same samples of CPDA-1 whole blood.

The goal of the study was the comparison of the WBPS method with conventional flow cytometry and the Quantitative PCR for WBC enumeration in leukoreduced blood.

Study Design: Six sets of blood samples with expected WBC concentrations of 0, 0.2, 1, 5, 25, 125, 600 cells/μl were prepared by subsequent dilutions of whole fresh blood with "WBC-free" diluent. Diluent was prepared by double filtration of the blood unit using leukoreduction filter. The first set was used for WBC enumeration in fresh blood samples with flow cytometry on day one. Five sets of samples were frozen at −70° C. Three of them were used for WBC counting with flow cytometry and WBPS kit on day two. Analysis of the remaining frozen sets using flow cytometry and quantitative PCR was performed on day seven.

Results

WBC counts in the samples with expected cell concentrations of 0; 0.2; 1; 5; 25; 125; and 600 cells/$\mu$l observed at three different sites using three different methods presented as an average of three measurements +/−SD of fresh or frozen blood:

Results

Figure 29:
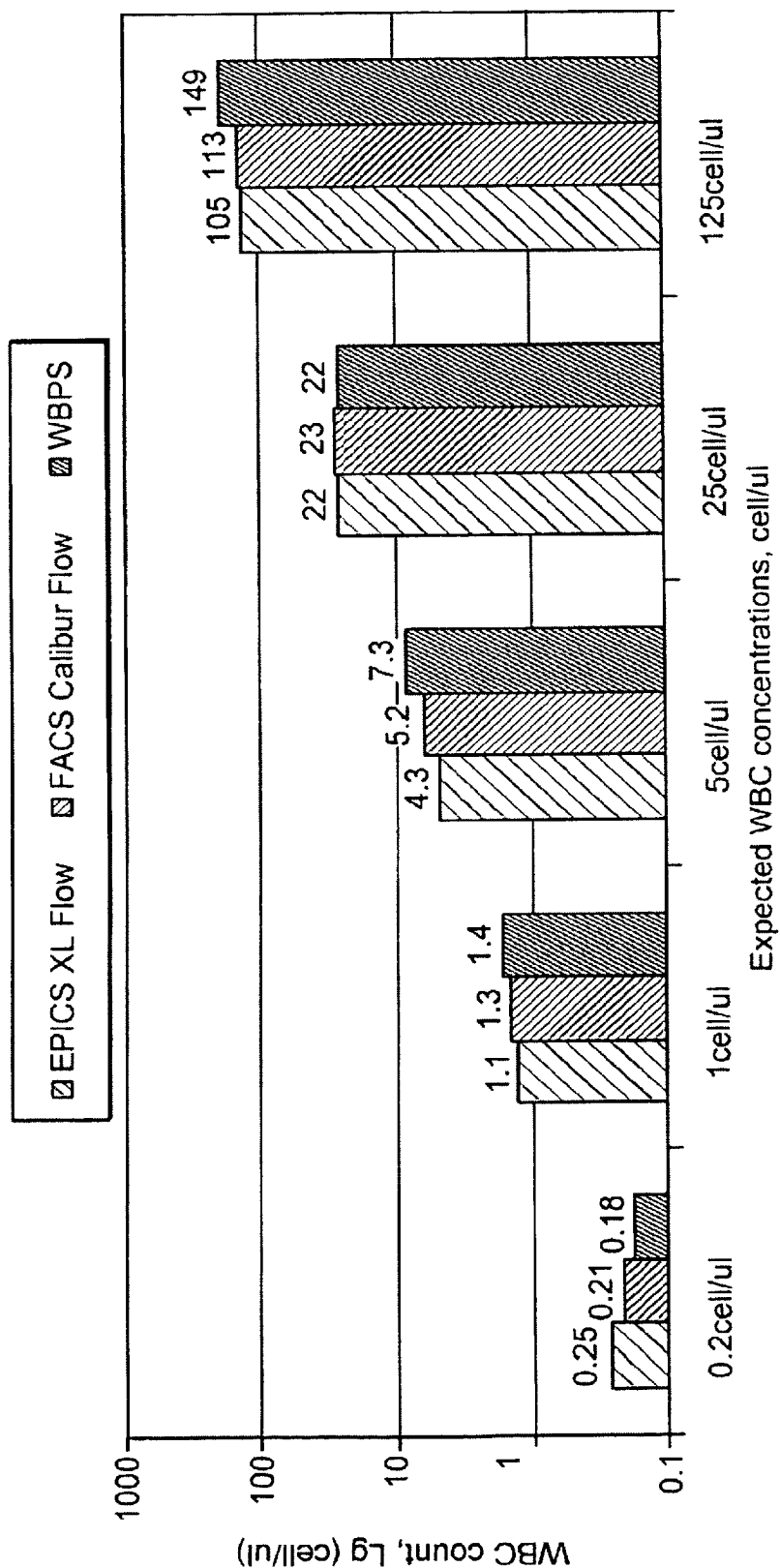
FIG. 29 depicts WBC counting in frozen RBC samples with WBPS and flow cytometry.

The WBPS DNA-extraction method is comparable with flow cytometry for leukocyte counting in RBC blood for the concentration in range of 0.2–125 cell/$\mu$l. The signal/noise ratio for DNA measurement in the sample with a concentration of 1 cell/$\mu$l was found to be no less then 3. Observed leukocyte counts in fresh and frozen RBC samples exhibit good correlation with expected cell concentrations (FIG. 28 and FIG. 29).

Conclusions

The WBPS DNA-extraction method meets the criteria of both the American Association of Blood Banks and the Council of Europe Standards for counting leukocytes in a leukoreduced RBC units. Freezing of RBC enables leukocyte recovery for subsequent quantitative analysis with both flow cytometry and the WBPS DNA-extraction method.

TABLE 11

| | 0 | 0.2 | 1 | 5 | 25 | 125 | 600 |
|---|---|---|---|---|---|---|---|
| Flowcyto. (Fresh) | 0.08 +/− 0.04 | 0.2 +/− 0.06 | 0.9 +/− 0.18 | 4.02 +/− 0.15 | 21.9 +/− 2.6 | 110.5 +/− 7.6 | 559.8 +/− 28.1 |
| Flowcyto. (Frozen) | 0.02 +/− 0.02 | 0.13 +/− 0.00 | 0.6 +/− 0.11 | 3.4 +/− 0.42 | 17.6 +/− 0.3 | 96.0 +/− 1.5 | 454.2 +/− 48.1 |
| WBPS (Frozen) | 0.28 +/− 0.09 | 0.44 +/− 0.11 | 1.1 +/− 0.15 | 3.3 +/− 0.76 | 21.8 +/− 4.3 | 127.9 +/− 4.2 | 605.0 +/− 80 |
| Quant. PCR (Frozen) | N/A | N/A | N/A | 2.0 | 12.2 | 108 | 696 |

Conclusion

WBPS DNA extraction method meets criterion of both the American Associations of Blood Banks and European Council Standards for counting leukocytes in a leukoreduced RBC unit. The sensitivity of the method is quite comparable with flow cytometry method. The quantitative PCR method has underestimation bias in range of concentration from 5 to 25 cells/$\mu$l.

Example 23

WBPS Method for Residual Leukocyte Evaluation in Leukoreduced Red Blood Cell Samples Comparison with Flow Cytometry Objectives Leukocyte concentration in serial diluted samples of Red Blood Cell (RBC) was evaluated with a WBPS and Pico-green fluorescent dye in parallel with flow cytometry using a LeucoCOUNT™ kit.

The goal of the study was the comparison of the flow cytometry and the WBPS DNA-extraction extraction methods for leukocyte enumeration in fresh and frozen leukoreduced RBC.

Study Design

Six sets of RBC samples with expected leukocyte concentrations of 0; 0.2; 1; 5; 25; 125; cells/$\mu$l were prepared by subsequent dilutions of fresh RBC with "leukocyte-free" diluent. Diluent was prepared by double filtration of the unit using r\LS filter (Hemasure). Three sets were evaluated as fresh blood samples on day one. Another three sets were frozen at −70° C. Leukocyte evaluation in these sets was performed after thawing on day two. Leukocytes were evaluated with flow cytometry using two devices, FACS Calibur (Becton Dickinson) and EPICS XL (Beckman Coulter). The WBPS DNA-extraction kit and Pico-green were used to evaluate WBC in the samples as alternative DNA extraction approach.

Example 24

Quantitative DNA Extraction and Detection Method for Residual Leukocyte Evaluation in Leukoreduced Blood Products Additional protocol for whole blood samples for leukoreduced blood samples.

The leukocyte concentration in whole blood samples varies from 4000 to 9000 cells per $\mu$l. The leukocyte concentration in leukoreduced blood samples is from 1 to 20 cells per $\mu$l.

Applicants have observed noticeable cell loss when a sample of leukoreduced blood was applied onto the original column.

Applicants suggested that media would hold leukocytes better if it is compressed in comparison with the original column.

The following experiment proved this hypothesis:

The original column contains filter media between two frits. The frit-filter media-frit sandwich configuration has several advantages. The upper frit in the column helps to maintain the flow of the blood product sample by enabling an even flow of sample to decrease clotting and by breaking up microclots. During the heat incubation step(s) prior to the elution step(s), the upper frit assists in retaining moisture and the lower frit assists in preventing dripping. Construction of the sandwich involves some compression of the material used to make the filter media in the ordinary course of the type used in the ordinary course of constructing filter media.

Samples of leukoreduced Red Blood Cell blood were applied into the original columns and the columns with further compressed media, in which the frit-filter media-frit sandwich was further compressed prior to addition of the sample. Columns with "compressed" media were further compressed so that the volume of the media was between 10 and 80% less than the original volume of the filter media, preferably between 25 and 75% less, and more preferably between 40 and 60% less than the original volume of the filter media. The samples of blood were as analyzed using standard flow cytometry methods, which are blood industry standards, and measured as containing 0.9, 4.9, 22.6, and 113 cells/µl.

Leukocyte counts were evaluated with flow cytometry using the LeucoCOUNT™ kit in all samples applied onto columns and in the same samples collected from the columns. The cell capturing was evaluated on basis of counts in "in" samples and "out" samples.

Figure 30:
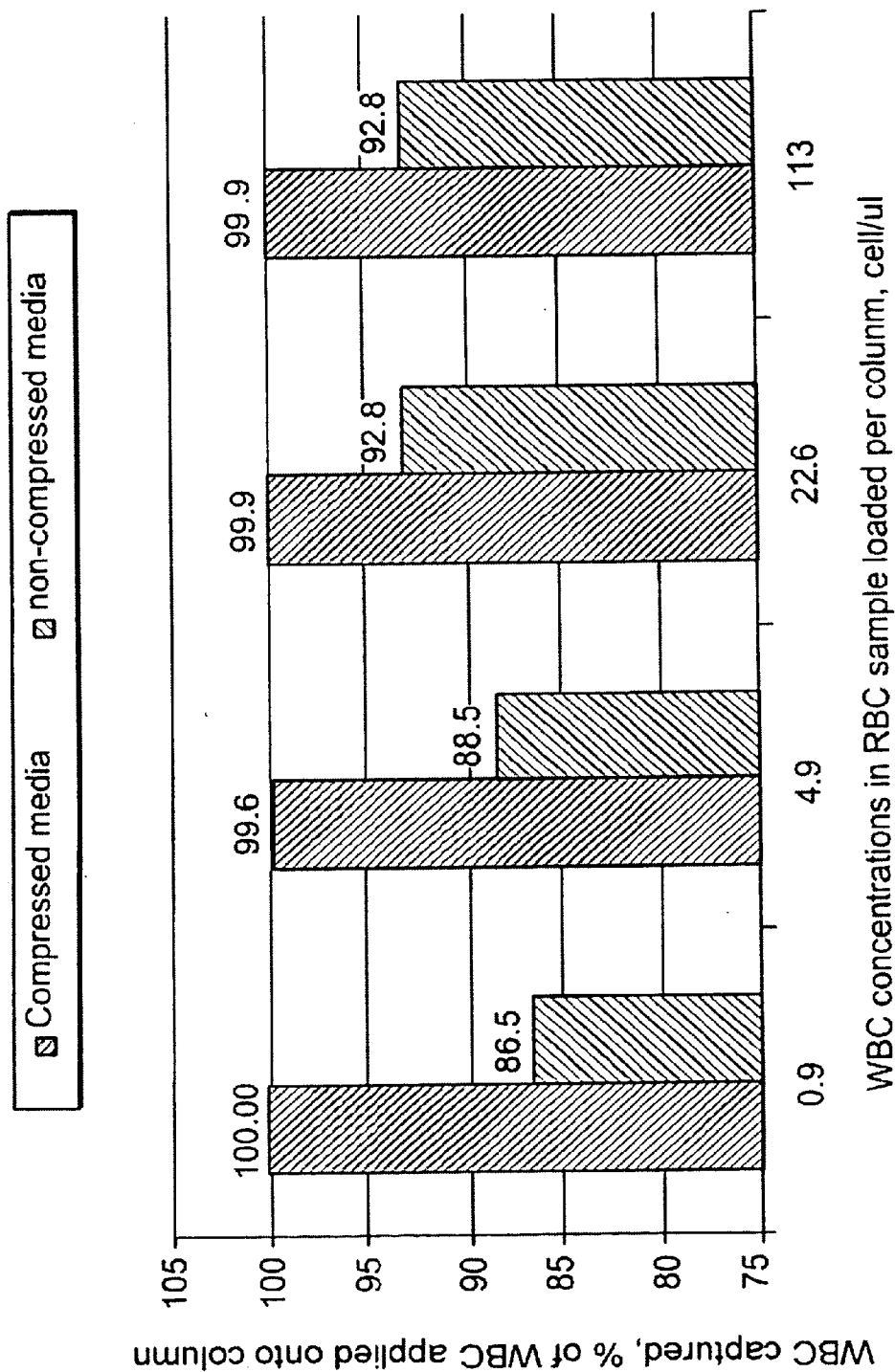
FIG. 30 depicts a comparison between compressed vs. non-compressed media of the WBPS columns for WBC capturing from leukoreduced RBC samples.

The data of this experiment is presented in FIG. 30 as a % of WBC captured from leukoreduced blood samples by the columns with compressed media vs. the columns with non-compressed media.

Conclusion

The WBC concentrations based on the data from the columns with compressed media are within 99.6%–100% of accuracy compared to flow cytometry results, while the columns with non-compressed media are within 86.5%–92.8% of accuracy.

Throughout this application, various publications including United States patents, are referenced by author and year and patents by number. Full citations for the publications are listed below. The disclosures of these publications and patents in their entireties are hereby incorporated by reference into this application in order to more fully described the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

REFERENCES

GC adapter immobilization to cellulose—Public domain; Yang et al. (1998) PNAS. vol. 95. pp. 5462–5467.
U.S. Pat. No. 5,496,562, Solid Medium and Method for DNA Storage, 1996 Renz, M., C. Kurz, "A colorimetric method for DNA hybridization," Nucleic Acids Research, 1984, vol. 12, No. 8, p.3435–3444
Matsuhisa A., Y. Kish, K. Shiba, "A Simple Staining Method for DNA and RNA blotted on a Membrane Using a Polyethyleneimine-Enzyme Conjugate," J. Biochem., 1994, vol. 116, p.478–481

We claim:

1. A method for determining the number of cells of interest in a sample, wherein the cells of interest comprise white blood cells comprising DNA, the method comprising:
  (a) applying a sample comprising cellular material to a filter, wherein the cellular material comprises cells of interest;
  (b) lysing the cells of interest to form a cell lysate;
  (c) immobilizing the released DNA on or within the filter;
  (d) removing the remaining cell lysate from the filter and retaining the DNA;
  (e) eluting the DNA from the filter;
  (f) quantifying the amount of the DNA eluted from the filter; and
  (g) determining the number of cells of interest in the sample based on the determined quantity of the DNA eluted.

2. A method for determining the number of cells of interest in a sample, wherein the cells of interest comprise white blood cells comprising DNA, the method comprising:
  (a) applying a sample comprising cellular material to a filter, wherein the cellular material comprises cells of interest;
  (b) lysing the cells of interest to form a cell lysate;
  (c) immobilizing the released DNA on or within the filter;
  (d) removing the remaining cell lysate from the filter and retaining the DNA;
  (e) quantifying the amount of the DNA retained on the filter; and
  (f) determining the number of cells of interest in the sample based on the determined quantity of the DNA retained.

3. A method for estimating the number of white blood cells in a blood sample from a source of interest, wherein the white blood cells comprise DNA, the method comprising:
  (a) isolating the DNA from the blood sample;
  (b) determining the amount of the DNA isolated from the blood sample; and
  (c) determining the number of white blood cells in the blood sample based on the determined amount of the isolated DNA.

4. The method according to claim 3, wherein the blood sample is a leukoreduced blood sample.

5. The method according to claim 4, wherein the DNA is genomic DNA, double-stranded DNA, or single-stranded DNA.

6. The method according to claim 4, wherein the estimated number of white blood cells is at least 85% of the number of white blood cells in a second blood sample as measured by flow cytometry, the method further comprising:
  (d) obtaining a second blood sample from the source of interest; and
  (e) measuring the number of white blood cells in the second blood sample using flow cytometry; and
  (f) comparing the number of white blood cells estimated for the blood sample in step (c) with the number measured in the second blood sample in step (e).

7. The method according to claim 6, wherein the estimated number of white blood cells is at least 90% of the number of white blood cells as measured by flow cytometry.

8. The method according to claim 6, wherein the estimated number of white blood cells is at least 95% of the number of white blood cells as measured by flow cytometry.

9. The method according to claim 6, wherein the estimated number of white blood cells is at least 98% of the number of white blood cells as measured by flow cytometry.

10. The method according to claim 6, wherein the estimated number of white blood cells is at least 99% of the number of white blood cells as measured by flow cytometry.

11. A method for determining the amount of white blood cells in a blood sample, wherein the white blood cells comprise DNA, the method comprising:
  (a) applying a blood sample comprising cells to a filter in the absence of a chaotrope;
  (b) retaining the cells with the filter as a cellular retentate and removing contaminants;
  (c) lysing the cellular retentate from step (b) to form a cell lysate while retaining the cell lysate in the filter, the cell lysate retentate containing the DNA;
  (d) removing the remaining cell lysate from the filter and retaining the DNA;

(e) eluting the DNA;

(f) measuring the amount of the DNA eluted from the filter; and (g) determining the amount of the DNA measured to estimate the number of white blood cells in the sample based on an amount of approximately 7 pg of nucleic acid contained in each white blood cell.

12. The method according to claim 11, wherein the DNA is genomic DNA, double-stranded DNA, or single-stranded DNA.

13. A method for isolating DNA from a blood sample comprising:

(a) applying a blood sample comprising cells to a filter in the absence of a chaotrope;

(b) retaining the cells with the filter as a cellular retentate and removing contaminants;

(c) lysing the cellular retentate from step (b) to form a cell lysate while retaining the cell lysate in the filter, the cell lysate retentate containing DNA;

(d) removing the remaining cell lysate from the filter and retaining the DNA;

(e) heating the DNA to an elevated temperature of 40° C. to 125° C. while retained by the filter;

(f) eluting the DNA;

(g) quantifying the amount of DNA eluted from the filter; and (h) determining the number of DNA-containing cells in the sample based on the determined quantity of the DNA eluted.

14. The method according to claim 13, wherein steps (e) and (f) together are repeated at least once.

15. The method according to claim 13, wherein the elevated temperature is in the range of 80° C. to 95° C.

16. The method according to claim 13, further comprising the method wherein, prior to step (a), the filter is compressed to between 10% and 80% less than its original volume.

17. The method according to claim 16, wherein the filter is compressed to between 25% and 75% less than its original volume.

18. The method according to claim 16, wherein the filter is compressed to between 40% and 60% less than its original volume.

19. The method according to claim 13, wherein the cellular retentate comprises intact whole blood cells.

20. The method according to claim 13, wherein the cell lysate retentate comprises condensed material from the nucleus and blood cell debris.

21. The method according to claim 13, wherein step (c) further comprises lysing the cellular retentate to form a cell lysate containing the nucleic acid by the addition of a low salt buffer capable of lysing the cells, followed by the removal of the low salt buffer.

22. The method according to claim 21, wherein step (b) comprises:

(a) rupturing the intact whole cells retained by the filter to leave condensed material from the nucleus retained by the filter; and (b) lysing the condensed material from the nucleus to form the cell lysate containing the DNA.

23. The method according to claim 22, wherein the intact whole cells are ruptured to form condensed material from the nucleus by addition of detergent.

24. The method according to claim 13, wherein the filter composition and dimensions are selected so that the DNA is retained by the filter in step (c) by non-ionic interaction.

25. The method according to claim 13, wherein the retaining step further comprises physically retarding the movement of the DNA through the filter.

26. The method according to claim 13, wherein the filter composition and dimensions are selected so that the DNA is retained by the filter in step (c) in the form of a web.

27. The method according to claim 13, wherein the filter comprises a plurality of fibers and has a disordered structure.

28. The method according to claim 27, wherein the fiber diameters are in the range of 1 $\mu$m to 10 $\mu$m.

29. The method according to claim 13, wherein the cells are white blood cells.

30. The method according to claim 29, which method further comprises applying blood to the solid phase, lysing the red blood cells therefrom, washing the solid phase to remove contaminants and obtaining the cell lysate from the white blood cells.

31. The method according to claim 30, wherein the blood is leukoreduced blood.

32. The method according to claim 31, wherein the estimated number of white blood cells is at least 85% of the number of white blood cells in a second blood sample as measured by flow cytometry, the method further comprising:

(i) obtaining a second blood sample from the source of interest; and (j) measuring the number of white blood cells in the second blood sample using flow cytometry; and (k) comparing the number of white blood cells determined for the blood sample in step (h) with the number measured in the second blood sample in step (j).

33. The method according to claim 32, wherein the estimated number of white blood cells is at least 90% of the number of white blood cells as measured by flow cytometry.

34. The method according to claim 32, wherein the estimated number of white blood cells is at least 95% of the number of white blood cells as measured by flow cytometry.

35. The method according to claim 32, wherein the estimated number of white blood cells is at least 98% of the number of white blood cells as measured by flow cytometry.

36. The method according to claim 32, wherein the estimated number of white blood cells is at least 99% of the number of white blood cells as measured by flow cytometry.

37. The method according to claim 13, wherein the DNA is genomic DNA, double-stranded DNA, or single-stranded DNA.

38. The method according to claim 13, which is carried out without any centrifugation steps.

39. The method according to claim 13, which is carried out in the absence of a chaotrope.

40. The method according to claim 13, wherein step (g) further comprises detecting the presence of the DNA using a fluorescent signal, color indicator, photometric indicator, enzymatic indicator, or radioactive indicator.

41. The method according to claim 13, wherein step (g) further comprises detecting the presence of the DNA using an indicator specific for double-stranded DNA.

42. The method according to claim 13, wherein step (g) further comprises detecting the presence of the DNA using an indicator from the group consisting of PicoGreen, a labeled nucleic acid probe specific for genomic DNA, ethidium bromide, or an indicator specific for double-stranded DNA.

43. A method for estimating the amount of white blood cells in a leukoreduced blood sample, wherein the white blood cells comprise DNA, the method comprising:

(a) compressing a filter to between 10% and 80% less than its original volume;

(b) applying a leukoreduced blood sample comprising cells to the filter in the absence of a chaotrope;

(c) retaining the cells with the filter as a cellular retentate comprising whole cells, condensed nuclear material, and cell debris;

(d) removing non-cellular contaminants from the retentate;

(e) lysing the cells in the cellular retentate from step (b) while the retentate is entrapped within the filter to form a cell lysate containing the DNA;

(f) retaining the DNA while removing remaining cell lysate;

(g) heating the DNA to an elevated temperature of 40° C. to 125° C. while retained by the filter, (h) eluting the DNA;

(i) measuring the amount of genomic DNA eluted from the filter;

(j) repeating steps (g) and (h); and (k) determining the amount of DNA measured to estimate the number of white blood cells in the sample based on an amount of approximately 7 pg of DNA contained in each white blood cell.

44. The method according to claim 43, wherein the estimated number of white blood cells is at least 85% of the number of white blood cells in a second leukoreduced blood sample as measured by flow cytometry, the method further comprising:

(l) obtaining a second blood sample from the source of interest; and (m) measuring the number of white blood cells in the second blood sample using flow cytometry; and (n) comparing the number of white blood cells estimated for the blood sample in step (k) with the number measured in the second blood sample in step (m).

45. The method according to claim 44, wherein the estimated number of white blood cells is at least 90% of the number of white blood cells as measured by flow cytometry.

46. The method according to claim 44, wherein the estimated number of white blood cells is at least 95% of the number of white blood cells as measured by flow cytometry.

47. The method according to claim 44, wherein the estimated number of white blood cells is at least 98% of the number of white blood cells as measured by flow cytometry.

48. The method according to claim 44, wherein the estimated number of white blood cells is at least 99% of the number of white blood cells as measured by flow cytometry.

49. A kit for quantifying the amount of genomic DNA in a blood sample comprising cells containing DNA comprising:

(a) a filter supported on a support, said filter comprising matrix means for physically retarding movement of DNA therethrough in the absence of a chaotrope;

(b) one or more solutions selected from the group consisting of a red cell lysis solution, a solution for rupturing intact whole cells to leave condensed nuclear material, a lysis solution for lysing nuclear material and an elution solution; and (c) an indicator capable of providing quantitative measurement of double-stranded or genomic DNA in a concentration as low as 1000 ng/ml.

50. The kit according to claim 49, wherein the indicator is capable of providing quantitative measurement of double-stranded or genomic DNA in a concentration as low as 200 pg/ml.

51. The kit according to claim 49, wherein the blood sample is a leukoreduced blood sample.

52. A method for estimating the amount of white blood cells in a blood sample, wherein the white blood cells comprise DNA, the method comprising:

(a) applying a blood sample to a substrate consisting of a coating enabling cellular lysis and release of the DNA, wherein the coating comprises a surfactant or detergent;

(b) immobilizing the released DNA to a matrix, the substrate physically capturing the DNA;

(c) bonding the DNA to the substrate;

(d) generating a signal when the DNA bonds to the substrate;

(e) analyzing the amount of DNA captured by quantifying the generated signal;

(f) estimating by calculation the number of white blood cells in the blood sample based on the amount of DNA isolated.

53. The method according to claim 54, wherein the generating step further comprises generating a fluorescent signal, color indicator, photometric indicator, enzymatic indicator, or radioactive indicator.

54. The method according to claim 52, wherein the blood sample is a leukoreduced blood sample.

55. The method according to claim 54, wherein the estimated number of white blood cells is at least 85% of the number of white blood cells in a second sample as measured by flow cytometry, the method further comprising:

(g) obtaining a second blood sample from the source of interest; and (h) measuring the number of white blood cells in the second blood sample using flow cytometry; and (i) comparing the number of white blood cells estimated for the blood sample in step (f) with the number measured in the second blood sample in step (h).

56. The method according to claim 55, wherein the estimated number of white blood cells is at least 90% of the number of white blood cells as measured by flow cytometry.

57. The method according to claim 55, wherein the estimated number of white blood cells is at least 95% of the number of white blood cells as measured by flow cytometry.

58. The method according to claim 55, wherein the estimated number of white blood cells is at least 98% of the number of white blood cells as measured by now cytometry.

59. The method according to claim 55, wherein the estimated number of white blood cells is at least 99% of the number of white blood cells as measured by flow cytometry.

60. The method according to claim 52, wherein the coating further comprises:

(i) a weak base; and (ii) a chelating agent.

61. The method according to claim 60, wherein the coating further comprises:

(iii) uric acid or a urate salt.

62. The method according to claim 52, wherein the surfactant or detergent comprises sodium dodecyl sulfate.

63. The method according to claim 60, wherein:

(i) the weak base comprises Tris; and (ii) the chelating agent comprises ethylenediaminetetraacetic acid.

* * * * *